(12) United States Patent
Sun et al.

(10) Patent No.: US 7,858,639 B2
(45) Date of Patent: Dec. 28, 2010

(54) BICYCLIC HETEROCYCLES AS CANNABINOID-1 RECEPTOR MODULATORS

(75) Inventors: Chongqing Sun, East Windsor, NJ (US);
Yanting Huang, Pennington, NJ (US);
Doree F. Sitkoff, Dresher, PA (US);
Taekyu Lee, Doylestown, PA (US);
William R. Ewing, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 12/609,436

(22) Filed: Oct. 30, 2009

(65) Prior Publication Data

US 2010/0048612 A1    Feb. 25, 2010

Related U.S. Application Data

(62) Division of application No. 11/455,039, filed on Jun. 16, 2006, now Pat. No. 7,632,837.

(60) Provisional application No. 60/692,045, filed on Jun. 17, 2005.

(51) Int. Cl.
*C07D 471/04* (2006.01)
*A61K 31/437* (2006.01)

(52) U.S. Cl. .................. 514/303; 546/119

(58) Field of Classification Search .............. 546/119; 514/303
See application file for complete search history.

(56) References Cited

U.S. PATENT DOCUMENTS

| | | |
|---|---|---|
| 3,674,836 A | 7/1972 | Creger |
| 3,983,140 A | 9/1976 | Endo et al. |
| 4,027,009 A | 5/1977 | Grier et al. |
| 4,231,938 A | 11/1980 | Monaghan et al. |
| 4,346,227 A | 8/1982 | Terahara et al. |
| 4,379,785 A | 4/1983 | Weyer et al. |
| 4,448,784 A | 5/1984 | Glamkowski et al. |
| 4,450,171 A | 5/1984 | Hoffman et al. |
| 4,499,289 A | 2/1985 | Baran et al. |
| 4,613,610 A | 9/1986 | Wareing |
| 4,639,436 A | 1/1987 | Junge et al. |
| 4,647,576 A | 3/1987 | Hoefle et al. |
| 4,681,893 A | 7/1987 | Roth |
| 4,686,237 A | 8/1987 | Anderson |
| 4,759,923 A | 7/1988 | Buntin et al. |
| 4,871,721 A | 10/1989 | Biller |
| 4,904,769 A | 2/1990 | Rauenbusch |
| 4,924,024 A | 5/1990 | Biller |
| 5,006,530 A | 4/1991 | Angerbauer et al. |
| 5,011,930 A | 4/1991 | Fujikawa et al. |
| 5,177,080 A | 1/1993 | Angerbauer et al. |
| 5,260,440 A | 11/1993 | Hirai et al. |
| 5,273,995 A | 12/1993 | Roth |
| 5,354,772 A | 10/1994 | Kathawala |
| 5,385,929 A | 1/1995 | Bjorge et al. |
| 5,447,954 A | 9/1995 | Gribble et al. |
| 5,488,064 A | 1/1996 | Sher |
| 5,491,134 A | 2/1996 | Sher et al. |
| 5,506,219 A | 4/1996 | Robl |
| 5,541,204 A | 7/1996 | Sher et al. |
| 5,594,016 A | 1/1997 | Ueno et al. |
| 5,612,359 A | 3/1997 | Murugesan |
| 5,686,104 A | 11/1997 | Mills et al. |
| 5,691,322 A | 11/1997 | Robl |
| 5,698,527 A | 12/1997 | Kim |
| 5,712,396 A | 1/1998 | Magnin et al. |
| 5,753,675 A | 5/1998 | Wattanasin |
| 5,770,615 A | 6/1998 | Cheng et al. |
| 5,776,983 A | 7/1998 | Washburn et al. |
| 5,990,109 A | 11/1999 | Chen et al. |
| 6,043,265 A | 3/2000 | Murugesan et al. |
| 6,184,231 B1 | 2/2001 | Hewawasam et al. |
| 6,414,002 B1 | 7/2002 | Cheng et al. |
| 6,635,626 B1 | 10/2003 | Barrish et al. |

FOREIGN PATENT DOCUMENTS

| | | |
|---|---|---|
| DE | 196 22 222 | 12/1997 |
| EP | 0 142 146 | 5/1985 |
| EP | 0 221 025 | 5/1987 |
| EP | 0675 714 | 10/1995 |

(Continued)

OTHER PUBLICATIONS

Vippagunta et al, "Crystalline Solids" Advanced Drug Delivery Reviews, vol. 48, pp. 3-26 (2001).*

(Continued)

*Primary Examiner*—Kahsay T Habte
(74) *Attorney, Agent, or Firm*—Anastasia P. Winslow; Maureen S. Gibbons; Burton Rodney

(57) ABSTRACT

The present application describes compounds according to Formula I, pharmaceutical compositions comprising at least one compound according to Formula I and optionally one or more additional therapeutic agents and methods of treatment using the compounds according to Formula I both alone and in combination with one or more additional therapeutic agents. The compounds have the following general formula:

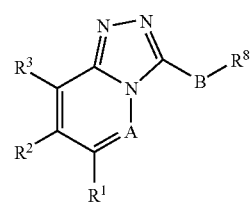

I including all prodrugs, solvates, pharmaceutically acceptable salts and stereoisomers, wherein A, B, $R^1$, $R^2$, $R^3$ and $R^8$ are described herein.

15 Claims, No Drawings

FOREIGN PATENT DOCUMENTS

| | | |
|---|---|---|
| EP | 0 818 448 | 1/1998 |
| EP | 0 992 496 | 4/2000 |
| EP | 1 022 272 | 7/2000 |
| FR | 2 596 393 | 10/1987 |
| GB | 2 205 837 | 12/1988 |
| GB | 2 304 106 | 3/1997 |
| WO | WO 86/03488 | 6/1986 |
| WO | WO 86/07054 | 12/1986 |
| WO | WO 94/15592 | 7/1994 |
| WO | WO 97/21993 | 6/1997 |
| WO | WO 97/35576 | 10/1997 |
| WO | WO 97/48701 | 12/1997 |
| WO | WO 99/00353 | 1/1999 |
| WO | WO 00/01389 | 1/2000 |
| WO | WO 00/15201 | 3/2000 |
| WO | WO 00/30665 | 6/2000 |
| WO | WO 00/38722 | 7/2000 |
| WO | WO 00/39077 | 7/2000 |
| WO | WO 00/50574 | 8/2000 |
| WO | WO 03/082833 | 10/2003 |
| WO | WO 03/084930 | 10/2003 |
| WO | WO 2004/026301 | 4/2004 |
| WO | WO 2005/063761 | 7/2005 |

OTHER PUBLICATIONS

Gavezzotti, "Are Crystal Structures Predictable?" Accounts of Chemical Research, vol. 27, pp. 309-314 (1994).*

Wolff Manfred E. "Burger's Medicinal Chemistry, 5ed, Part 1" John Wiley & Sons, 1995, pp. 975-977.*

Banker, G.S. et al, "Modern Paharmaceutices, 3ed." Marcel Dekker, New York, 1996, pp. 451 and 596.*

Biller, S. et al., "Squalene Synthase Inhibitors", Current Pharmaceutical Design, vol. 2, pp. 1-40 (1996).

Biller, S. et al., "Isoprenoid (Phosphinylmethyl) phosphonates as Inhibitors of Squalene Synthetase", J. of Medicinal Chemistry, vol. 31(10), pp. 1869-1871 (1988).

Capson, T., "Synthesis and Evaluation of Ammonium Analogs of Carbocationic Intermediates in Squalene Biosynthesis", Dissertation, Univ of Utah, Abstract, Table of contents, pp. 16, 17, 40-43, 48-51 (1987).

Colombo, G. et al., "Appetite suppression and weight loss after the cannabinoid antagonist SR 141716", Life Sciences, vol. 63(8), pp. PL 113-117 (1998).

Corey, E. et al., "Application of Unreactive analogs of terpenoid pyrophosphates to studies of multistep biosynthesis. Demonstration that "Presqualene Pyrophosphate" is an essential intermediate on the path to squalene", J. of the American Chem. Society, vol. 98(5), pp. 1291-1293 (1976).

Cottet, F. et al., "Logistic flexibility in the preparation of isomeric halopyridinecarboxylic acids", Tetrahedron, vol. 60, pp. 11869-11874 (2004).

Davidsen, S. et al., "N-(Acyloxyalkyl) pyridinium salts as soluble prodrugs of a Potent Platelet activating factor antagonist", J. of Medicinal Chemisry, vol. 37(26), pp. 4423-4429 (1994).

Di Marzo, V. et al., "Leptin-regulated endocannabinoids are involved in maintaining food intake", Nature, vol. 410, pp. 822-825 (2001).

Ettmayer, P. et al., "Lessons Learned from Marketed and Investigational Prodrugs", J. of Medicinal Chemistry, vol. 47(10), pp. 2393-2404 (2004).

Galiègue, S. et al., "Expression of central and peripheral cannabinoid receptors in human immune tissues and leukocyte subpopulations", Eur. J. Biochem., vol. 232, pp. 54-61 (1995).

Ghiselli, G., "The Pharmacological Profile of FCE 27677: A Novel ACAT Inhibitor with Potent Hypolipidemic Activity Mediated by Selective Suppression of the Hepatic Secretion of ApoB-100-Containing Lipoprotein", Cardiovascular Drug Reviews, vol. 16(1), pp. 16-30 (1998).

Glass, M. et al., "Cannabinoid receptors in the human brain: A detailed anatomical and quantitative autoradiographic study in the fetal, neonatal and adult human brain", Neuroscience, vol. 77(2), pp. 299-318 (1997).

Hara, S., "Ileal Na+/bile acid cotransporter inhibitors", Drugs of the Future, vol. 24(4), pp. 425-430 (1999).

Hildebrandt, A. et al., "Antiobesity effects of chronic cannabinoid $CB_1$ receptor antagonist treatment in diet-induced obese mice", Eur. J. of Pharmacology, vol. 462, pp. 125-132 (2003).

Hollenbaugh, D. et al., "The human T cell antigen gp39, a member of the TNF gene family, is a ligand for the CD40 receptor: expression of a soluble form of gp39 with B cell co-stimulatory activity", The EMBO Journal, vol. 11(12), pp. 4313-4321 (1992).

Hollenbaugh, D. et al., "Cleavable CD40Ig fusion proteins and the binding to sgp39", J. of Immunological Methods, vol. 188, pp. 1-7 (1995).

Krause, B et al., "ACAT Inhibitors: Physiologic Mechanisms for Hypolipidemic and Anti-Atherosclerotic Activities in Experimental Animals", Inflammation: Mediators and Pathways, pp. 173-198 (1995).

Ljung, B. et al., "AZ 242, a novel PPARα/γ agonist with beneficial effects on insulin resistance and carbohydrate and lipid metabolism in ob/ob mice and obese Zucker rats", J. of Lipid Research, vol. 43, pp. 1855-1863 (2002).

Matsuda, L. et al., "Structure of a cannabinoid receptor and functional expression of the cloned cDNA", Nature, vol. 346, pp. 561-564 (1990).

McClard, R. et al., "Novel Phosphonylphosphinyl (P-C-P-C-) Analogues of Biochemically interesting dephosphates, Syntheses and Properties of P-C-P-C- Analogues of Isopentenyl Diphosphate and Dimethylallyl Diphosphate", J. Am. Chem. Soc., vol. 109, pp. 5544-5545 (1987).

Moreland, L. et al., "Treatment of Rheumatoid Arthritis with a Recombinant Human tumor necrosis factor receptor (p75)-Fc Fusion Protein", The New England Journal of Medicine, vol. 337(3), pp. 141-147 (1997).

Munro, S. et al., "Molecular characterization of a peripheral receptor for cannabinoids", Nature, vol. 365, pp. 61-65 (1993).

Nicolosi, R. et al., "The ACAT inhibitor, CI-1011 is effective in the prevention and regression of aortic fatty streak area in hamsters", Atherosclerosis, vol. 137, pp. 77-85 (1998).

Ortiz de Montellano, P. et al., "Inhibition of Squalene Synthetase by Farnesyl Pyrophosphate Analogues", J. of Medicinal Chemistry, vol. 20(2), pp. 243-249 (1977).

Rosenblum, S. et al., "Discovery of 1-(4-Fluorophenyl)-(3R)-[3-(4-fluorophenyl)-(3S)-hydroxypropyl]-(4S)-(4-hydroxyphenyl)-2-azetidinone (SCH 58235) : A Designed, Potent, Orally Active Inhibitor of Cholesterol Absorption", J. Med. Chem., vol. 41, pp. 973-980 (1998).

Rowland, N. et al., "Effects of the cannabinoid receptor antagonist SR 141716, alone and in combination with dexfenfluramine or naloxone, on food intake in rats", Psychopharmacology, vol. 159, pp. 111-116 (2001).

Salisbury, B. et al., "Hypocholesterolemic activity of a novel inhibitor of cholesterol absorption, SCH 48461", Atherosclerosis, vol. 115, pp. 45-63 (1995).

Sliskovic, D. et al., "ACAT Inhibitors: Potential Anti-atherosclerotic Agents", Current Medicinal Chemistry, vol. 1, pp. 204-225 (1994).

Smith, C. et al., "RP 73163: A Bioavailable Alkylsulphinyl-Diphenylimidazole ACAT Inhibitor", Bioorganic & Medicinal Chemistry Letters, vol. 6(1), pp. 47-50 (1996).

Sorbera, L. et al., "Treatment of Lipoprotein Disorders, ACAT Inhibitor" Avasimibe, Drugs of the Future, vol. 24(1), pp. 9-15 (1999).

Stout, D., :Inhibitors of Acyl-CoA: Cholesterol O-Acyl Transferase (ACAT) as Hypocholesterolemic Agents. 6. The first Water-soluble ACAT Inhibitor with Lipid-regulating activity. Inhibitors of Acyl-CoA: Cholesterol Acyltransferase (ACAT). 7. Development of a Series of Substituted N-Phenyl-N-[1-phenylcyclopentyl)-methyl] ureas with Enhanced Hypocholestrolemic Activity, Chemtracts-Organic Chemistry, vol. 8, pp. 359-362 (1995).

Toma, L. et al., "Mono- and Di-Substituted 5,6-Diphenyl-3-Alkylamino-Pyridazines active as ACAT Inhibitors", Heterocycles, vol. 57(1), pp. 39-46 (2002).

Trillou, C. et al., "Anti-obesity effect of SR141716, a CB1 receptor antagonist, in diet-induced obese mice", Am. J. Physiol Regul Integr Comp Physiol., vol. 284, pp. R345-R353 (2003).

Yajima, K. et al., "Combination therapy with PPARγ and PPARα agonists increases glucose-stimulated insulin secretion in db/db mice", Am. J. Physiol. Endocrinol Metab., vol. 284, pp. E966-E971 (2003).

Hertzog, Donald L., "Recent advances in the cannabinoids", Expert Opinion on Therapeutic Patents, vol. 14(10), pp. 1435-1452 (2004).

Wiley, J. et al., "Novel Pyrazole Cannabinoids: Insights into $CB_1$ receptor Recognition and Activation", J. of Pharmacology and Experimental Therapeutics, vol. 296(3), pp. 1013-1022 (2001).

Vippagunta et al., "Crystalline Solids", Advanced Drug Delivery Review, vol. 48, pp. 3-26 (2001).

Gavezzotti, "Are Crystal Structures Predictable?", Accounts of Chemical Research, vol. 27, pp. 309-314 (1994).

Wolff, Manfred E., "Burger's Medicinal Chemistry, 5th Edition, Part 1", John Wiley & Sons, pp. 975-977, (1995).

Banker, G.S., et al., "Modern Pharmaceutics, 3rd Edition", Marcel Dekker, New York, pp. 451 and 596 (1996).

* cited by examiner

BICYCLIC HETEROCYCLES AS CANNABINOID-1 RECEPTOR MODULATORS

RELATED APPLICATION

This application is a divisional of Ser. No. 11/455,039, filed Jun. 16, 2006 (now U.S. Pat. No. 7,632,837) which claims priority benefit under Title 35 §119(e) of U.S. Provisional Application No. 60/692,045, filed Jun. 17, 2005, the contents of which are herein incorporated by reference.

BACKGROUND

Delta-9-tetrahydrocannabinol or Delta-9 THC, the principle active component of *Cannabis sativa* (marijuana), is a member of a large family of lipophilic compounds (i.e., cannabinoids) that mediate physiological and psychotropic effects including regulation of appetite, immunosuppression, analgesia, inflammation, emesis, anti-nocioception, sedation, and intraocular pressure. Other members of the cannabinoid family include the endogenous (arachidonic acid-derived) ligands, anandamide, 2-arachidonyl glycerol, and 2-arachidonyl glycerol ether. Cannabinoids work through selective binding to and activation of 6-protein coupled cannabinoid receptors. Two types of cannabinoid receptors have been cloned including CB-1 (L. A. Matsuda, et al., Nature, 346, 561-564 (1990)), and CB-2 (S. Munro, et al., Nature, 365, 61-65 (1993)). The CB-1 receptor is highly expressed in the central and peripheral nervous systems (M. Glass, et al., Neuroscience, 77, 299-318 (1997)), while the CB-2 receptor is highly expressed in immune tissue, particularly in spleen and tonsils. The CB-2 receptor is also expressed on other immune system cells, such as lymphoid cells (S. Galiegue, et al., Eur J Biochem, 232, 54-61 (1995)). Agonist activation of cannabinoid receptors results in inhibition of cAMP accumulation, stimulation of MAP kinase activity, and closure of calcium channels.

There exists substantial evidence that cannabinoids regulate appetitive behavior. Stimulation of CB-1 activity by anandamide or Delta-9 THC results in increased food intake and weight gain in multiple species including humans (Williams and Kirkham, Psychopharm., 143, 315-317 (1999)). Genetic knock-out of CB-1 result in mice that were hypophagic and lean relative to wild-type litter mates (DiMarzo, et al., Nature, 410, 822-825 (2001)). Published studies with CB-1 small molecule antagonists have demonstrated decreased food intake and body weight in rats (Trillou, et. al., Am. J. Physiol. Regul. Integr. Comp. Physiol., R345-R353, (2003)). Chronic administration of the CB-1 antagonist AM-251 for two weeks resulted in substantial body weight reduction and decreased adipose tissue mass (Hildebrandt, et. al., Eur. J. Pharm, 462, 125-132 (2003)). There are multiple studies that have assessed the anorexic effect of the Sanofi CB-1 antagonist, SR-141716 (Rowland, et. al., Psychopharm., 159, 111-116 (2001); Colombo, et. al., Life Sci., 63, 113-117 (1998)). There are at least two CB-1 antagonists in clinical trials for regulation of appetite, Sanofi's SR-141716 and Solvay's SLV-319. Published Phase IIb data reveal that SR-141716 dose-dependently reduced body weight in human subjects over a 16 week trial period. CB-1 antagonists have also been shown to promote cessation of smoking behavior Phase II clinical data on smoking cessation were presented in September of 2002 at Sanofi-Synthelabo's Information meeting. This data showed that 30.2% of patients treated with the highest dose of SR-141716 stayed abstinent from cigarette smoke relative to 14.8% for placebo.

DETAILED DESCRIPTION

The present application describes compounds according to Formula I, pharmaceutical compositions comprising at least one compound according to Formula I and optionally one or more additional therapeutic agents and methods of treatment using the compounds according to Formula I both alone and in combination with one or more additional therapeutic agents. The compounds have the general Formula I

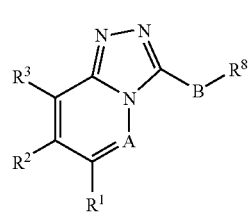

including all prodrugs, solvates, pharmaceutically acceptable salts and stereoisomers, wherein A, B, $R^1$, $R^2$, $R^3$ and $R^8$ are described herein.

DEFINITIONS

The following definitions apply to the terms as used throughout this specification, unless otherwise limited in specific instances.

As used herein, the term "alkyl" denotes branched or unbranched hydrocarbon chains containing 1 to 20 carbons, preferably 1 to 12 carbons, and more preferably 1 to 8 carbons, in the normal chain, such as, methyl, ethyl, propyl, isopropyl, butyl, isobutyl, tert-butyl, pentyl, hexyl, isohexyl, heptyl, 4,4-dimethylpentyl, octyl, 2,2,4-trimethylpentyl and the like. Further, alkyl groups, as defined herein, may optionally be substituted on any available carbon atom with one or more functional groups commonly attached to such chains, such as, but not limited to hydroxyl, halo, haloalkyl, mercapto or thio, cyano, alkylthio, cycloalkyl, heterocyclyl, aryl, heteroaryl, carboxyl, carbalkoyl, carbonyl, alkenyl, alkynyl, nitro, amino, alkoxy, aryloxy, arylalkyloxy, heteroaryloxy, amido, —OC(O)NRR, —OC(O)R, —OPO$_3$H, —OSO$_3$H, and the like to form alkyl groups such as trifluoromethyl, 3-hydroxyhexyl, 2-carboxypropyl, 2-fluoroethyl, carboxymethyl, cyanobutyl and the like.

Unless otherwise indicated, the term "alkenyl" as used herein by itself or as part of another group refers to straight or branched chains of 2 to 20 carbons, preferably 2 to 12 carbons, and more preferably 2 to 8 carbons with one or more double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like. Further, alkenyl groups, as defined herein, may optionally be substituted on any available carbon atom with one or more functional groups commonly attached to such chains, such as, but not limited to halo, haloalkyl, alkyl, alkoxy, alkynyl, aryl, arylalkyl, cycloalkyl, amino, hydroxyl, heteroaryl, cycloheteroalkyl, alkanoylamino, alkylamido, arylcarbonylamino, nitro, cyano, thiol, alkylthio and/or any of the alkyl substituents set out herein.

Unless otherwise indicated, the term "alkynyl" as used herein by itself or as part of another group refers to straight or branched chains of 2 to 20 carbons, preferably 2 to 12 carbons and more preferably 2 to 8 carbons with one or more triple bonds in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like. Further, alkynyl groups, as defined herein, may optionally be substituted on any available carbon atom with one or more functional groups commonly attached to such chains, such as, but not limited to halo, haloalkyl, alkyl, alkoxy, alkenyl, aryl, arylalkyl, cycloalkyl, amino, hydroxyl, heteroaryl, cycloheteroalkyl, alkanoylamino, alkylamido, arylcarbonylamino, nitro, cyano, thiol, alkylthio and/or any of the alkyl substituents set out herein.

Unless otherwise indicated, the term "cycloalkyl" as employed herein alone or as part of another group includes saturated or partially unsaturated (containing one or more double bonds) cyclic hydrocarbon groups containing 1 to 3 rings, appended or fused, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

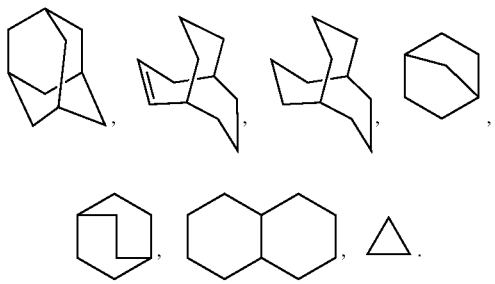

Further, any cycloalkyl may be optionally substituted through any available carbon atoms with one or more groups selected from hydrogen, halo, haloalkyl, alkyl, alkoxy, haloalkyloxy, hydroxyl, alkenyl, alkynyl, aryl, aryloxy, heteroaryl, heteroaryloxy, arylalkyl, heteroarylalkyl, alkylamido, alkanoylamino, oxo, acyl, arylcarbonylamino, amino, nitro, cyano, thiol and/or alkylthio and/or any of the alkyl substituents.

The term "cycloalkylalkyl" as used herein alone or as part of another group refers to alkyl groups as defined above having a cycloalkyl substituent, wherein said "cycloalkyl" and/or "alkyl" groups may optionally be substituted as defined above.

Unless otherwise indicated, the term "aryl" as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring, for example,

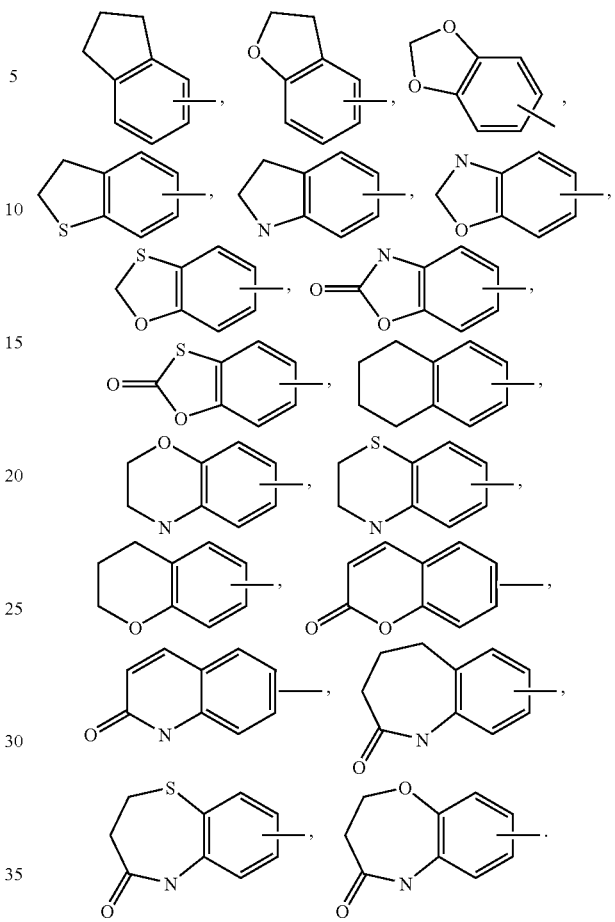

Further, "aryl", as defined herein, may optionally be substituted with one or more functional groups, such as halo, alkyl, haloalkyl, alkoxy, haloalkoxy, alkenyl, alkynyl, cycloalkyl, cycloalkylalkyl, heterocyclyl, heterocycloalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxyl, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl and/or any of the alkyl substituents set out herein.

Unless otherwise indicated, the term "heteroaryl" as used herein alone or as part of another group refers to a 5- or 6-membered aromatic ring which includes 1, 2, 3 or 4 hetero atoms such as nitrogen, oxygen or sulfur. Such rings may be fused to an aryl, cycloalkyl, heteroaryl or heterocyclyl and include possible N-oxides as described in Katritzky, A. R. and Rees, C. W., eds. Comprehensive Heterocyclic Chemistry: The Structure, Reactions, Synthesis and Uses of Heterocyclic Compounds 1984, Pergamon Press, New York, N.Y.; and Katritzky, A. R., Rees, C. W., Scriven, E. F., eds. Comprehensive Heterocyclic Chemistry II: A Review of the Literature 1982-1995 1996, Elsevier Science, Inc., Tarrytown, N.Y.; and references therein. Further, "heteroaryl", as defined herein, may optionally be substituted with one or more substituents such as the substituents included above in the definition of "substituted alkyl" and "substituted aryl". Examples of heteroaryl groups include the following:

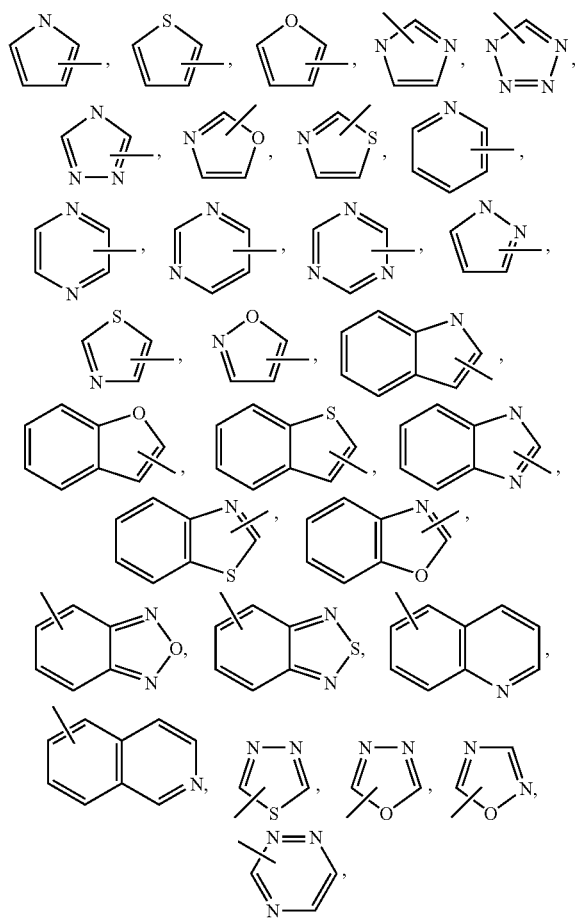

and the like.

The term "heteroarylalkyl" as used herein alone or as part of another group refers to alkyl groups as defined above having a heteroaryl substituent, wherein said heteroaryl and/or alkyl groups may optionally be substituted as defined above.

The term "heterocyclo", "heterocycle", "heterocyclyl" or "heterocyclic ring", as used herein, represents an unsubstituted or substituted stable 4 to 7-membered monocyclic ring system which may be saturated or unsaturated, and which consists of carbon atoms, with one to four heteroatoms selected from nitrogen, oxygen or sulfur, and wherein the nitrogen and sulfur heteroatoms may optionally be oxidized, and the nitrogen heteroatom may optionally be quaternized. The heterocyclic ring may be attached at any heteroatom or carbon atom which results in the creation of a stable structure. Examples of such heterocyclic groups include, but is not limited to, azetidinyl, pyrrolidinyl, piperidinyl, piperazinyl, oxopiperazinyl, oxopiperidinyl, oxopyrrolidinyl, oxoazepinyl, azepinyl, pyrrolyl, pyrrolidinyl, furanyl, thienyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isooxazolyl, isoxazolidinyl, morpholinyl, thiazolyl, thiazolidinyl, isothiazolyl, thiadiazolyl, tetrahydropyranyl, thiamorpholinyl, thiamorpholinyl sulfoxide, thiamorpholinyl sulfone, oxadiazolyl and other heterocycles described in Katritzky, A. R. and Rees, C. W., eds. *Comprehensive Heterocyclic Chemistry: The Structure, Reactions, Synthesis and Uses of heterocyclic Compounds* 1984, Pergamon Press, New York, N.Y.; and Katritzky, A. R., Rees, C. W., Scriven, E. F., eds. *Comprehensive Heterocyclic Chemistry II: A Review of the Literature* 1982-1995 1996, Elsevier Science, Inc., Tarrytown, N.Y.; and references therein.

The term "heterocycloalkyl" as used herein alone or as part of another group refers to alkyl groups as defined above having a heterocyclyl substituent, wherein said heterocyclyl and/or alkyl groups may optionally be substituted as defined above.

The terms "arylalkyl", "arylalkenyl" and "arylalkynyl" as used alone or as part of another group refer to alkyl, alkenyl and alkynyl groups as described above having an aryl substituent. Representative examples of arylalkyl include, but are not limited to, benzyl, 2-phenylethyl, 3-phenylpropyl, phenethyl, benzhydryl and naphthylmethyl and the like.

The term "alkoxy", "aryloxy", "heteroaryloxy" "arylalkyloxy", or "heteroarylalkyloxy" as employed herein alone or as part of another group includes an alkyl or aryl group as defined above linked through an oxygen atom.

The term "halogen" or "halo" as used herein alone or as part of another group refers to chlorine, bromine, fluorine, and iodine, with bromine, chlorine or fluorine being preferred.

The term "cyano," as used herein, refers to a —CN group.

The term "methylene," as used herein, refers to a —CH$_2$— group.

The term "nitro," as used herein, refers to a —NO$_2$ group.

The compounds of formula I can be present as salts, which are also within the scope of this invention. Pharmaceutically acceptable (i.e., non-toxic, physiologically acceptable) salts are preferred. If the compounds of formula I have, for example, at least one basic center, they can form acid addition salts. These are formed, for example, with strong inorganic acids, such as mineral acids, for example sulfuric acid, phosphoric acid or a hydrohalic acid, with organic carboxylic acids, such as alkanecarboxylic acids of 1 to 4 carbon atoms, for example acetic acid, which are unsubstituted or substituted, for example, by halogen as chloroacetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$-$C_4$) alkyl or arylsulfonic acids which are unsubstituted or substituted, for example by halogen, for example methyl- or p-toluene-sulfonic acid. Corresponding acid addition salts can also be formed having, if desired, an additionally present basic center. The compounds of formula I having at least one acid group (for example COON) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or trilower alkylamine, for example ethyl, tert-butyl, diethyl, diisopropyl, triethyl, tributyl or dimethyl-propylamine, or a mono, di or trihydroxy lower alkylamine, for example mono, di or triethanolamine. Corresponding internal salts may furthermore be formed. Salts which are unsuitable for pharmaceutical uses but which can be employed, for example, for the isolation or purification of free compounds of formula I or their pharmaceutically acceptable salts, are also included.

Preferred salts of the compounds of formula I which contain a basic group include monohydrochloride, hydrogensulfate, methanesulfonate, phosphate, nitrate or acetate.

Preferred salts of the compounds of formula I which contain an acid group include sodium, potassium and magnesium salts and pharmaceutically acceptable organic amines.

The term "modulator" refers to a chemical compound with capacity to either enhance (e.g., "agonist" activity) or partially enhance (e.g., "partial agonist" activity) or inhibit (e.g., "antagonist" activity or "inverse agonist" activity) a functional property of biological activity or process (e.g., enzyme activity or receptor binding); such enhancement or inhibition may be contingent on the occurrence of a specific event, such as activation of a signal transduction pathway, and/or may be manifest only in particular cell types.

The term "bioactive metabolite" as employed herein refers to any functional group contained in a compound of formula I with an open valence for further substitution wherein such substitution can, upon biotransformation, generate a compound of formula I. Examples of such functional groups of bioactive metabolites include, but are not limited to, —OH, —NH or functional groups wherein the hydrogen can be replaced with a functional group such as —$PO_3H_2$ for example, which, upon biotransformation generates an —OH or —NH functional group of a compound of formula I.

The term "prodrug esters" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates and the like. Prodrug esters may also include—but are not limited to groups such as phosphate esters, phosphonate esters, phosphonamidate esters, sulfate esters, sulfonate esters, and sulfonamidate esters wherein the ester may be further substituted with groups that confer a pharmaceutical advantage such as—but not limited to—favorable aqueous solubility or in vivo exposure to the bioactive component formula I.

The term "prodrug" as employed herein includes functionalization of bioactive amine- or hydroxy-containing compounds of formula I to form alkyl-, acyl-, sulfonyl-, phosphoryl-, or carbohydrate-substituted derivatives. Such derivatives are formed by reacting compounds of formula I with alkylating-, acylating-, sulfonylating-, or phosphorylating reagents employing procedures known to those skilled in the art. Alkylation of amines of formula I may result in—but are not limited to—derivatives that include spacer units to other prodrug moieties such as substituted alkoxymethyl-, acyloxymethyl-, phosphoryloxymethyl-, or sulfonyloxymethyl-groups. Alkylation of amines of formula I may result in the generation of quaternary amine salts that act in vivo to provide the bioactive agent (i.e., the compound of formula I).

Preferred prodrugs consist of a compound of formula I where a pendant hydroxyl is phosphorylated to generate a phosphate derivative. Such a prodrug may also include a spacer group between the compound of formula I and the phosphate group, such as a methyleneoxy-group. Methods to generate such a prodrug from a compound of formula I are known to those skilled in the art, and are listed in the references below.

Preferred prodrugs also consist of a compound of formula I where a pendant amine, such as a pyridine group, is alkylated with a group, such as methyl, to form a quaternary ammonium ion salt. Methods to generate such a prodrug from a compound of formula I are known to those skilled in the art, and are listed in the references below.

Any compound that can be converted in vivo to provide the bioactive agent (i.e., the compound of formula I) is a prodrug within the scope and spirit of the invention.

Various forms of prodrugs are well known in the art. A comprehensive description of prodrugs and prodrug derivatives are described in:
a) *The Practice of Medicinal Chemistry*, Camille G. Wermuth et al., Ch 31, (Academic Press, 1996);
b) *Design of prodrugs*, edited by H. Bundgaard, (Elsevier, 1985);
c) *A Textbook of Drug Design and Development*, P. Krogsgaard-Larson and H. Bundgaard, eds. Ch 5, pgs 113-191 (Harwood Academic Publishers, 1991);
d) *Hydrolysis in Drug and Prodrug Metabolism*, B. Testa and J. M. Mayer, (Verlag Helvetica Chimica Acta AG, Zurich, Switzerland; Wiley-VCH, Weinheim, Federal Republic of Germany, 2003);
e) Ettmayer, P.; Amidon, G. L.; Clement, B.; Testa, B. "Lessons Learned from Marketed and Investigational Prodrugs" *J. Med. Chem.* 2004, 47 (10), 2393-2404; and
f) Davidsen, S. K. et al. "N-(Acyloxyalkyl)pyridinium Salts as Soluble Prodrugs of a Potent Platelet Activating Factor Antagonist" *J. Med. Chem.* 1994, 37 (26), 4423-4429.

Said references are incorporated herein by reference.

An administration of a therapeutic agent of the invention includes administration of a therapeutically effective amount of the agent of the invention. The term "therapeutically effective amount" as used herein refers to an amount of a therapeutic agent to treat or prevent a condition treatable by administration of a composition of the invention. That amount is the amount sufficient to exhibit a detectable therapeutic or preventative or ameliorative effect. The effect may include, for example, treatment or prevention of the conditions listed herein. The precise effective amount for a subject will depend upon the subject's size and health, the nature and extent of the condition being treated, recommendations of the treating physician, and the therapeutics or combination of therapeutics selected for administration.

All stereoisomers of the compounds of the instant invention are contemplated, either in mixture or in pure or substantially pure form. The compounds of the present invention can have asymmetric centers at any of the carbon atoms including any one of the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic techniques, chiral HPLC or fractional crystallization.

The compounds of formula I of the invention can be prepared as shown in the following reaction schemes and description thereof, as well as relevant published literature procedures that may be used by one skilled in the art. Exemplary reagents and procedures for these reactions appear hereinafter and in the working Examples.

ABBREVIATIONS

The following abbreviations are employed in the Schemes, Examples and elsewhere herein:

AcOH=acetic acid $AlCl_3$=aluminum chloride

Boc=tert-butoxycarbonyl

DMF=N,N-dimethylformamide

DMSO=dimethyl sulfoxide

EDAC=N-(3-dimethylaminopropyl)-N'-ethylcarbodiimide hydrochloride

EtOAc=ethyl acetate $Et_3N$=triethylamine $Et_2O$=diethyl ether

HPLC or LC=high performance liquid chromatography

HfOBt=1-hydroxybenzotriazole $(i-Pr)_2EtN$=diisopropylethylamine $K_3PO_4$ potassium phosphate tribasic $K_2CO_3$=potassium carbonate MeOH=methanol MOM=methoxymethyl Ms=methanesulfonyl MS or Mass Spec=mass spectrometry NaCl=sodium chloride $NaHCO_3$=sodium bicarbonate $Na_2SO_4$=sodium sulfate $Na_2CO_3$=sodium carbonate NaOH=sodium hydroxide $Pd(Ph_3P)_4$=tetrakis(triphenylphosphine)palladium(0)

$Ph_3PCl_2$=triphenylphosphine dichloride

PG=protecting group $POCl_3$=phosphorus oxychloride $Pd(dppf)Cl_2$=[1,1'-bis(diphenylphosphino)-ferrocene]dichloropalladium(II)

TFA=trifluoroacetic acid

THF=tetrahydrofuran

Ts=p-toluenesulfonyl min=minute(s)

h=hour(s)

L=liter(s)

mL=milliliter(s)

μL=microliter(s)

g=gram(s)

mg=milligram(s)

mol=moles mmol=millimole(s)

M=molar nM=nanomolar $[M+H]^+$=parent plus a proton $[M+Na]^+$=parent plus a sodium ion $[M-H]^-$=parent minus a proton Compounds of the present invention may be prepared by procedures illustrated in the accompanying schemes.

METHODS OF PREPARATION

The compounds of the present invention may be prepared by methods such as those illustrated in the following Schemes. Solvents, temperatures, pressures, and other reaction conditions may readily be selected by one of ordinary skill in the art. Starting materials are commercially available or can be readily prepared by one of ordinary skill in the art using known methods. For all of the schemes and compounds described below, A, B, $R^1$, $R^2$, $R^3$ and $R^8$ are as described for a compound of formula I.

The following are the definitions of symbols used throughout Schemes 1 to 3:

PG suitable nitrogen or oxygen protecting group, exemplified by benzyl, methoxymethyl-[MOM], benzyloxymethyl-[BOM], 2-(trimethylsilyl)ethoxymethyl-[SEM], methoxyethoxymethyl-[MEM], or t-butyl groups;

EE leaving group exemplified by halogen (F, Cl, Br, I) and sulfonates ($—OSO_2$-aryl (e.g., $—OSO_2Ph$ or $—OSO_2PhCH_3$), or $—OSO_2$-alkyl (e.g., $—OSO_2CH_3$ or $—OSO_2CF_3$).

SCHEME 1

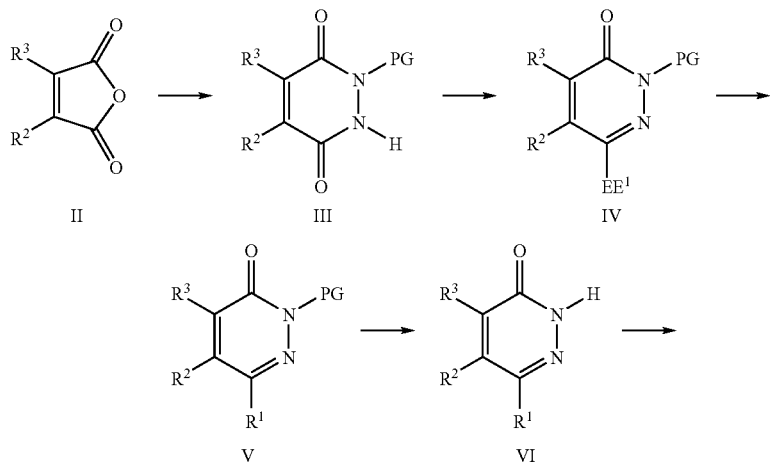

-continued

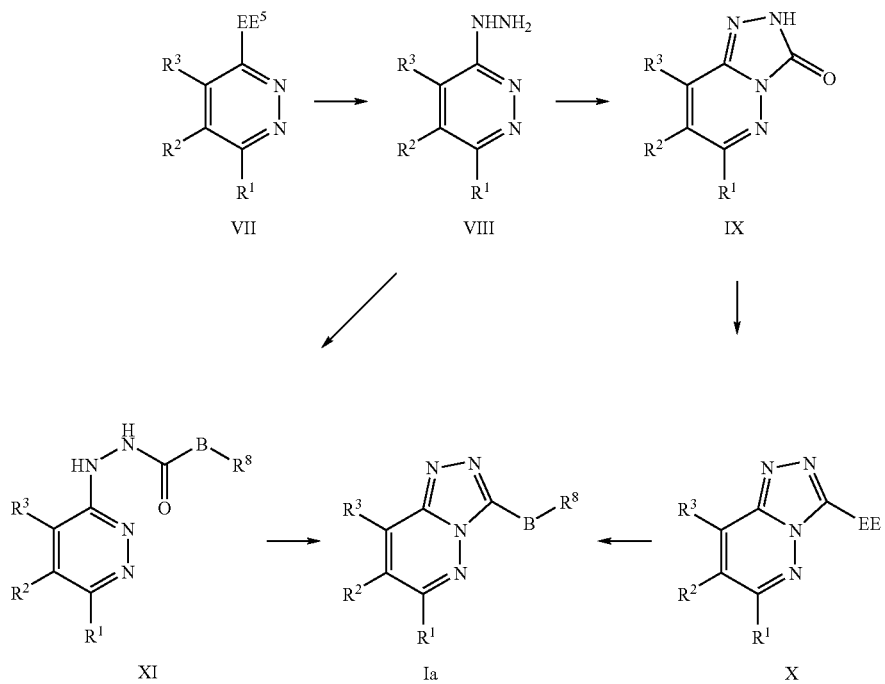

Compounds of formula II are either commercially available or available by means known to one skilled in the art. Compounds of formula III can be prepared by reacting compounds of formula II with an appropriately protected hydrazine such as benzylhydrazine. Exemplary nitrogen protecting groups and methods of protecting the nitrogen are similar to those for protecting amines, such as those described in T. W. Greene and P. G. M. Wuts, *Protecting Groups in Organic Synthesis*, John Wiley & Sons, Inc, New York, 1991. Preferred nitrogen protecting groups are benzyl, tert-butyl, methoxymethyl (MOM) groups.

Compounds of formula IV, where $EE^1$=Cl, can be prepared by reacting compounds of formula III with a chlorinating agent such as $POCl_3$, either neat or in an inert solvent such as toluene at elevated temperature.

Compounds of formula V can be prepared by reaction of compounds of formula IV with an activated $R^1$, such as an activated boronic acid, tin, Grignard reagents, Zinc, Cu, etc in the presence of an appropriate catalyst if needed such as Pd(dppf)$Cl_2$, complex with $CH_2Cl_2$.

Compounds of formula VI can be prepared by removing the protecting group (PG) in compound V under catalytic hydrogenation (for benzyl), or Lewis acid (e.g. $AlCl_3$ for benzyl or MOM), acidic (e.g. TFA for t-butyl or Boc-) conditions.

Compounds of formula VII, where $EE^5$=Cl, can be prepared by reacting compounds of formula VI with a chlorinating agent such as $POCl_3$, either neat or in an inert solvent such as toluene at elevated temperature. Compounds of formula VII, where $EE^5$=Cl, can also be prepared according to the procedures described in Toma, L.; et. al. *Heterocycles*, 57(1), pp. 39-46, (2002).

Compounds of formula VIII can be prepared by reacting compounds of formula VII with hydrazine in an inert solvent such as pyridine at elevated temperature.

Compounds of formula IX can be prepared by reacting compounds of formula VIII with a carbonylating agent such as carbonyldiimidazole, phosgene, triphosgene or urea in an inert solvent such as tetrahydrofuran.

Compounds of formula X, where be EE=Cl, can be prepared by reacting compounds of formula IX with a chlorinating agent such as $POCl_3$, either neat or in an inert solvent such as toluene at elevated temperature.

Compounds of formula XI can be prepared by reacting compounds of formula VIII with a carboxylic acid ($R^8$—B—$CO_2H$, where B is $CR^6R^7$) via amide bond formation which employs either a coupling reagent, such as 1(3-dimethylaminopropyl)-3-ethylcarbodiimide hydrochloride, or a mixed anhydride formed between the carboxylic acid and isobutyl chloroformate in the presence of a base, such as triethylamine.

Compounds of formula Ia can be prepared from a compound of formula X via displacement of the leaving group (HE) by the conjugate base of a compound $R^8$—B—H (where B is O or $NR^6$) in an inert solvent, such as THF in the presence of a base.

Exemplary bases include triethylamine, sodium carbonate, potassium carbonate, cesium carbonate, sodium hydride, sodium alkoxide, potassium tert-butoxide, or alkyl lithiums.

Compounds of formula Ia (where B is $CR^6R^7$) can be prepared from compounds of formula XI via intramolecular cyclization in the presence of an activating reagent, such as triphenylphosphine dichloride, or acetic acid in ethanol at elevated temperature.

SCHEME 2

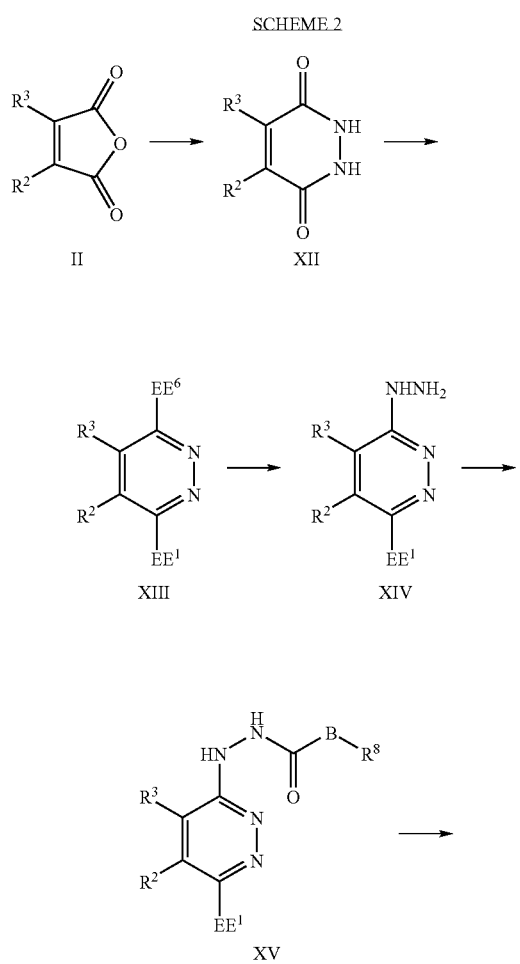

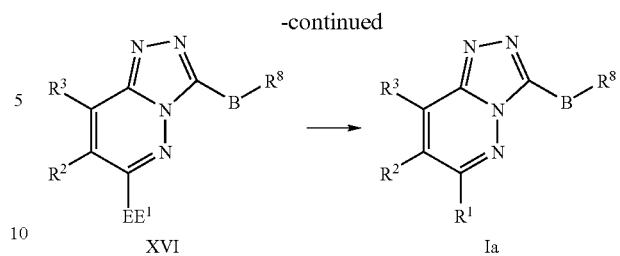

Compounds of formula XII can be prepared by reacting compounds of formula II with hydrazine dihydrochloride in an aqueous or alcoholic solvent at elevated temperature.

Compounds of formula XIII, where $EE^1=EE^5=Cl$, can be prepared by reacting compounds of formula XII with a chlorinating agent such as $POCl_3$, either neat or in an inert solvent such as toluene at elevated temperature.

Compounds of formula XIV can be prepared by reacting compounds of formula XIII with hydrazine in an inert solvent such as pyridine at elevated temperature.

Compounds of formula XV can be prepared by reacting compounds of formula XIV with a carboxylic acid ($R^8$—B—$CO_2H$, where B is $CR^6R^7$) via amide bond formation which employs either a coupling reagent, such as 1(3-dimethylaminopropyl)-3-ethylcarbodiimide hydrochloride, or a mixed anhydride formed between the carboxylic acid and isobutyl chloroformate in the presence of a base, such as triethylamine.

Compounds of formula XVI can be prepared from compounds of formula XV via intramolecular cyclization in the presence of an activating reagent, such as triphenylphosphine dichloride, or acetic acid in ethanol at elevated temperature.

Compounds of formula Ia can be prepared by reaction of compounds of formula XVI with an activated $R^1$, such as an activated boronic acid, tin, Grignard reagents, Zinc, Cu, etc in the presence of an appropriate catalyst if needed such as $Pd(dppf)Cl_2$, complex with $CH_2Cl_2$.

SCHEME 3

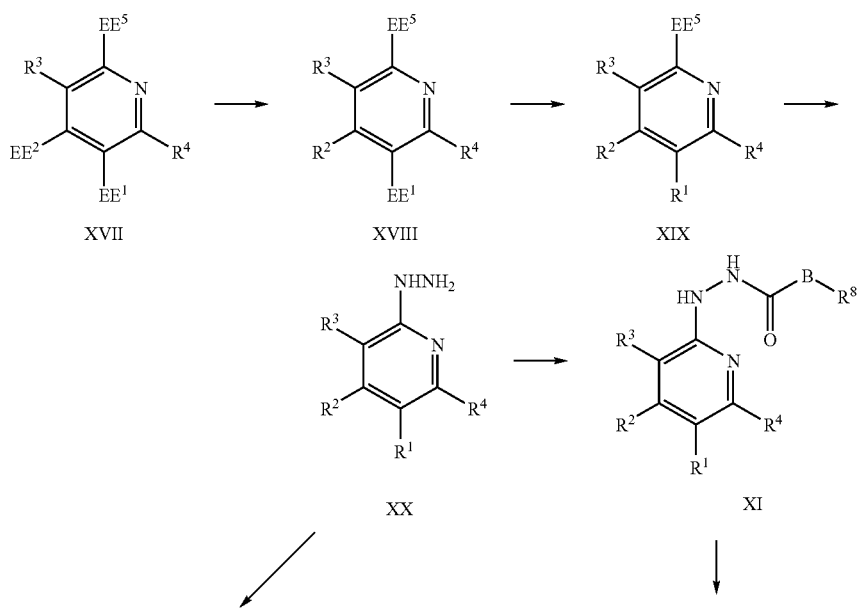

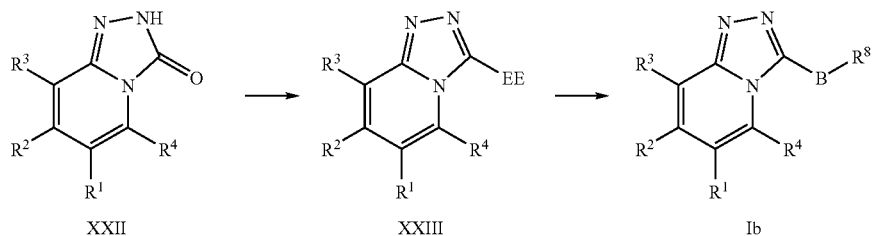

Compounds of formula XVII are either commercially available or can be prepared by procedures analogous to those described in Cottet, F. and Schlosser, M. *Tetrahedron*, 60, pp. 11896-11874 (2004).

Compounds of formula XVIII can be prepared by reaction of compounds of formula XVII with an activated $R^2$, such as an activated boronic acid, tin, Grignard reagents, Zinc, Cu, etc in the presence of an appropriate catalyst if needed such as $Pd(Ph_3P)_4$.

Compounds of formula XIX can be prepared by reaction of compounds of formula XVIII with an activated $R^1$, such as an activated boronic acid, tin, Grignard reagents, Zinc, Cu, etc in the presence of an appropriate catalyst if needed such as $Pd_2(dba)_3$.

Compounds of formula XX can be prepared by reacting compounds of formula XIX with hydrazine in an inert solvent, such as pyridine, at elevated temperature.

Compounds of formula XXI can be prepared by reacting compounds of formula XX with a carboxylic acid ($R^8$—B—$CO_2H$, where B is $CR^6R^7$) via amide bond formation reaction which employs either a coupling reagent, such as 1(3-dimethylaminopropyl)-3-ethylcarbodiimide hydrochloride, in the presence of a base, such as diisopropylethylamine.

Compounds of formula Ib can be prepared from compounds of formula XXI via intramolecular cyclization in the presence of an activating reagent, such as triphenylphosphine dichloride, or acetic acid in ethanol at elevated temperature.

Compounds of formula XXII can be prepared by reacting compounds of formula XX with a carbonylating agent such as carbonyldiimidazole, phosgene, triphosgene or urea in an inert solvent such as tetrahydrofuran.

Compounds of formula XXIII, where EE=Cl, can be prepared by reacting compounds of formula XXII with a chlorinating agent such as $POCl_3$, either neat or in an inert solvent such as toluene at elevated temperature.

Compounds of formula Ib can be prepared from a compound of formula XXIII via displacement of the leaving group (EE) by the conjugate base of a compound $R^8$—B—H (where B is O or $NR^6$) in an inert solvent, such as THF in the presence of a base. Exemplary bases include triethylamine, sodium carbonate, potassium carbonate, cesium carbonate, sodium hydride, sodium alkoxide, potassium tert-butoxide, or alkyl lithiums.

SCHEME 4

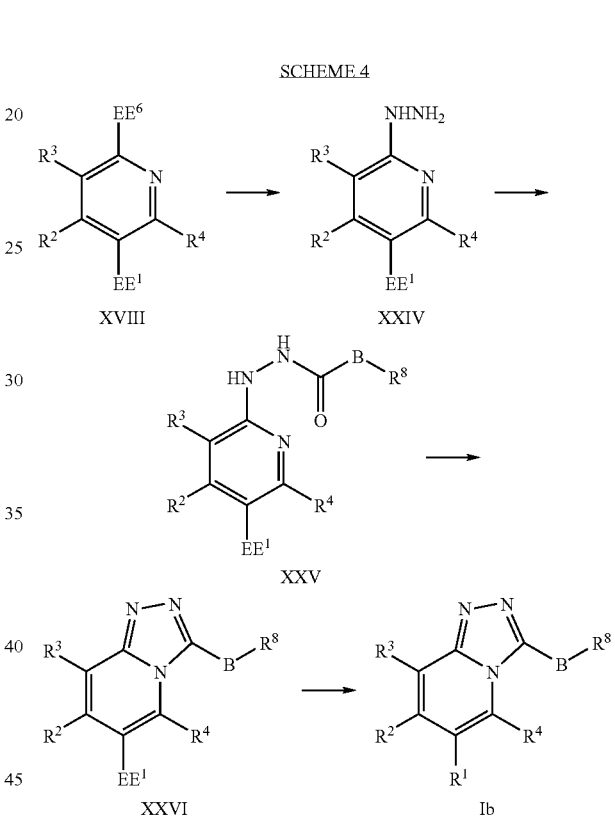

Compounds of formula XXIV can be prepared by reacting compounds of formula XVIII with hydrazine in an inert solvent, such as tetrahydrofuran, at elevated temperature.

Compounds of formula XXV can be prepared by reacting compounds of formula XXIV with a carboxylic acid ($R^8$—B—$CO_2H$, where B is $CR^6R^7$) via amide bond formation reaction which employs either a coupling reagent, such as 1(3-dimethylaminopropyl)-3-ethylcarbodiimide hydrochloride, or bromotripyrrolidinophosphonium hexafluorophosphate in the presence of a base, such as diisopropylethylamine.

Compounds of formula XXVI can be prepared from compounds of formula XXV via intramolecular cyclization in the presence of an activating reagent, such as triphenylphosphine dichloride, or acetic acid in an inert solvent at elevated temperature.

Compounds of formula Ib can be prepared by reaction of compounds of formula XXVI with an activated $R^1$, such as an activated boronic acid, tin, Grignard reagents, Zinc, Cu, etc in the presence of an appropriate catalyst if needed such as Pd(PPh$_3$)$_4$.

SCHEME 5

Compounds of formula XXVIII (where A=N or CR$^4$, R=alkyl) can be prepared by reacting compounds of formula XXVII with diethyl oxylate in an inert solvent, such as toluene, at elevated temperature, or reacting with ethyl glyoxylate in tetrahydrofuran first, then with bromine at elevated temperature.

Compounds of formula Ic (where A=N or CR$^4$) can be prepared by reaction of compounds of formula XXVIII with excess of an amine of formula R$^6$R$^9$NH either neat or in a polar solvent, such as methanol or ethanol at elevated temperature.

EXAMPLES

The following examples serve to better illustrate, but not limit, some of the preferred embodiments of the invention.

Analytical HPLC and HPLC/MS Methods Employed in Characterization of Examples

Analytical HPLC was performed on Shimadzu LC10AS liquid chromatographs.

Analytical HPLC/MS was performed on Shimadzu LC10AS liquid chromatographs and Waters ZMD Mass Spectrometers using the following methods:

Method A. Linear gradient of 0 to 100% solvent B over 4.0 min, with 1 min hold at 100% B;
UV visualization at 220 rn
Column: Phenomenex Lura C18, 4.6×50 mm
Flow rate: 4 ml/min Solvent A: 0.1% trifluoroacetic acid, 90% water, 10% methanol Solvent B: 0.1% trifluoroacetic acid, 10% water, 90% methanol.

Method B. Linear gradient of 0 to 100% solvent B over 2.0 min, with 1 min hold at 100% B;
UV visualization at 220 nm
Column: Phenomenex Lura C18, 4.6×30 mm
Flow rate: 5 ml/min Solvent A: 0.1% trifluoroacetic acid, 90% water, 10% methanol Solvent B: 0.1% trifluoroacetic acid, 10% water, 90% methanol.

NMR Employed in Characterization of Examples $^1$H NMR spectra were obtained with Bruker or JOEL fourier transform spectrometers operating at the following frequencies: $^1$H NMR: 400 Mhz (Bruker), 400 MHz (JOEL), or 500 MHz (JOEL); $^{13}$C NMR: 100 MHz (Bruker), 100 MHz (JOEL) or 125 MHz (JOEL). Spectra data are reported as Chemical shift (multiplicity, number of hydrogens, coupling constants in Hz) and are reported in ppm (δ units) relative to either an internal standard (tetramethylsilane=0 ppm) for $^1$H NMR spectra, or are referenced to the residual solvent peak (2.49 ppm for CD$_2$HSOCD$_3$, 3.30 ppm for CD$_2$HOD, 7.24 ppm for CHCl$_3$, 39.7 ppm for CD$_3$SOCD$_3$, 49.0 ppm for CD$_3$OD, 77.0 ppm for CDCl$_3$). All $^{13}$C NMR spectra were proton decoupled.

Example 1

Preparation of 6-(2-chlorophenyl)-7-(4-chlorophenyl)-N-cyclohexyl-[1,2,4]triazolo[4,3-b]pyridazin-3-amine 1A. Preparation of 2-benzyl-5-(4-chlorophenyl)-6-hydroxypyridazin-3(2H)-one To a suspension of 3-(4-chlorophenyl)-2,5-furandione (10.24 g, 66.9 mmol) in acetic acid (300 mL) was added benzylhydrazine dihydrochloride in one portion (19.6 g, 100 mmol). The reaction mixture was stirred at reflux for 14 h. Analysis by HPLC/MS indicated the reaction was complete. After cooling to room temperature, the resulting white suspension was filtered. The collected solid was washed with EtOAc (20 mL×2), and dried in a 50° C. vacuum oven for 16 h to yield 6.5 g of the desired product as a white solid. The filtrate was concentrated under reduced pressure, and the obtained residue was crystallized in EtOAc to afford additional 1.6 g of the title compound (8.1 g in total, 39% yield). HPLC/MS (method A): retention time=3.29 min, (M+H)$^+$=

313.1. $^1$H NMR (DMSO-d$_6$, 500 MHz): δ 11.62 (s, 1H), 7.65 (d, J=10 Hz, >2H), 7.51 (d, J=10 Hz, 2H), 7.23-7.38 (m, 5H), 7.04 (s, 1H), 5.11 (s, 2H).

1B. Preparation of 2-benzyl-6-chloro-5-(4-chlorophenyl)pyridazin-3(2H)-one

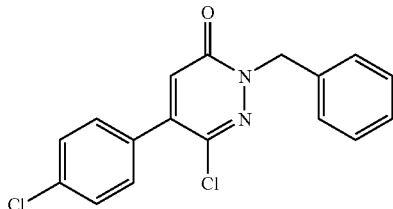

A suspension of 2-benzyl-5-(4-chlorophenyl)-6-hydroxypyridazin-3(2H)-one (8.5 g, 27.2 mmol) in phosphorus oxychloride (50 mL) was stirred at 95° C. for 1 h. Analysis by HPLC/MS indicated the starting material had been consumed. After cooling to room temperature, the reaction mixture was concentrated under reduced pressure. The obtained residue was diluted with EtOAc. The resulting EtOAc solution was washed with saturated aqueous NaHCO$_3$, saturated aqueous NaCl, dried (Na$_2$SO$_4$), filtered and concentrated under reduced pressure. The crude product was purified using a silica gel cartridge (330 g) eluting with a gradient of EtOAc (0-40%) in hexanes to afford 6.2 g (69%) of the title compound as a white solid. HPLC/MS (method A): retention time=3.80 min, (M+H)$^+$=331.0. $^1$H NMR (CDCl$_3$, 400 MHz): δ 7.27-7.80 (m, 9H), 6.88 (s, 1H), 5.36 (s, 2H).

1C. Preparation of 2-benzyl-6-(2-chlorophenyl)-5-(4-chlorophenyl)pyridazin-3(2H)-one

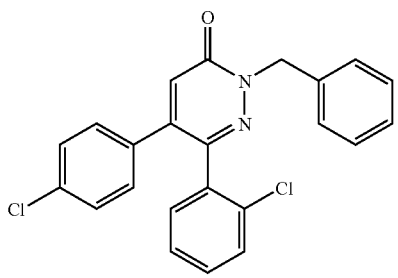

To a flame-dried round bottom flask was placed 2-benzyl-6-chloro-5-(4-chlorophenyl)pyridazin-3(2H)-one (6.0 g, 18.1 mmol), 2-chlorophenylboronic acid (5.7 g, 36.2 mmol), K$_3$PO$_4$ (7.7 g, 36.2 mmol), and [1,1'-bis(diphenylphosphino)-ferrocene]dichloropalladium(II), complex with CH$_2$Cl$_2$ (1:1) (2.96 g, 3.6 mmol). The flask was purged with argon for 15 min before degassed THF (120 mL) was added. The reaction mixture was stirred in a 70° C. oil bath under argon for 16 h. After cooling to room temperature, the reaction mixture was diluted with EtOAc (200 mL), washed with 1N aqueous NaOH (50 mL), H$_2$O, saturated aqueous NaCl, dried (Na$_2$SO$_4$), filtered and concentrated under reduced pressure. The crude product was purified using a silica gel cartridge (330 g) eluting with a gradient of EtOAc (0-40%) in hexanes to afford 6.5 g (88%) of the title compound as a white solid. HPLC/MS (method A): retention time=3.97 min, (M+H)$^+$= 407.0. $^1$H NMR (CDCl$_3$, 400 MHz): δ 7.51 (d, 2H, J=8.0 Hz), 7.24-7.40 (m, 9H), 6.95-7.03 (m, 3H), 5.33 (s, 2H).

1D. Preparation of 6-(2-chlorophenyl)-5-(4-chlorophenyl)pyridazin-3(2H)-one

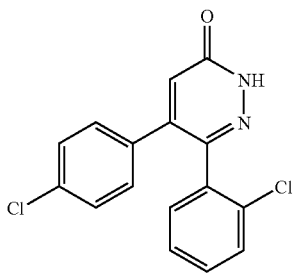

To a solution of 2-benzyl-6-(2-chlorophenyl)-5-(4-chlorophenyl)pyridazin-3(2H)-one (6.4 g, 15.7 mmol) in toluene (100 mL) at 90° C. was added aluminum chloride (5.23 g, 39.3 mmol) in one portion. After addition, the reaction mixture was stirred at 90° C. for 20 min. After cooling to room temperature, the reaction mixture was concentrated under reduced pressure to reduce the volume to about 50 mL, then water (150 mL) was added. The resulting mixture was sonicated for 5 min, then stirred at room temperature for 10 min. The resulting suspension was filtered, the collected solid was washed with water (20 mL×3), hexanes (20 mL×3) and dried in a 50° C. vacuum oven for 16 h to afford 4.2 g (76%) of the title compound as a white solid. HPLC/MS (method A): retention time=3.27 min, (M+H)$^+$=317.0. $^1$H NMR (CDCl$_3$, 400 MHz): δ 11.6 (S, 1H), 7.17-7.40 (m, 6H), 6.90-7.10 (m, 3H).

1E. Preparation of 6-chloro-3-(2-chlorophenyl)-4-(4-chlorophenyl)pyridazine

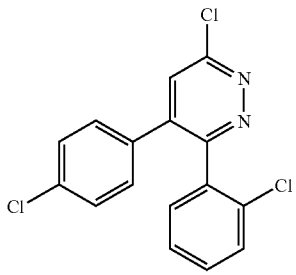

A suspension of 6-(2-chlorophenyl)-5-(4-chlorophenyl)pyridazin-3(2H)-one (4.1 g, 12.9 mmol) in phosphorus oxychloride (15 mL) was stirred at 95° C. for 1 h. After cooling to room temperature, the reaction mixture was concentrated under reduced pressure. The residue was partitioned between EtOAc and saturated aqueous NaHCO$_3$. The separated aqueous layer was extracted with EtOAc (40 mL×2). The combined organic was washed with saturated aqueous NaHCO$_3$, saturated aqueous NaCl, dried Na$_2$SO$_4$) and concentrated under reduced pressure to afford 4.2 g (97%) of the title compound as a pink foam. HPLC/MS (method A): retention time=3.50 min, (M+H)$^+$=335.0.

1F. Preparation of 1-(6-(2-chlorophenyl)-5-(4-chlorophenyl)pyridazin-3)hydrazine

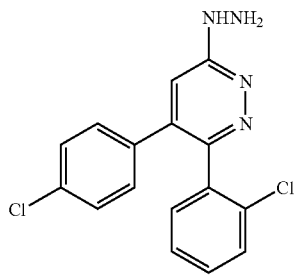

To a solution of 6-chloro-3-(2-chlorophenyl)-4-(4-chlorophenyl)pyridazine (2.1 g, 6.26 mmol) in pyridine (20 mL) at 90° C. was added anhydrous hydrazine (1 mL), and the resulting mixture was stirred at 90° C. for 1 h. Analysis by HPLC/MS indicated the reaction was not complete. Additional hydrazine (0.5 mL) was added, and the reaction continued at 90° C. for 1 h more. After cooling to room temperature, the reaction was concentrated under reduced pressure. The obtained residue was treated with water (50 mL), and the resulting suspension stirred at room temperature for 10 min, then filtered. The collected solid was washed with water (20 mL×3), dried in a 50° C. vacuum oven for 16 h to afford 2.1 g (100%) of the title compound as a pink solid. HPLC/MS (method A): retention time=2.67 min, (M+H)$^+$=331.0.

1G. Preparation of 6-(2-chlorophenyl)-7-(4-chlorophenyl)-[1,2,4]triazolo[4,3-b]pyridazin-3(2H)-one

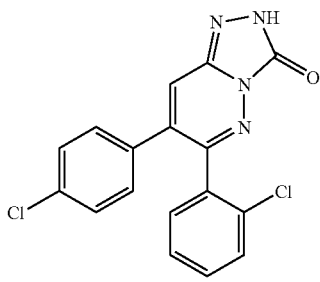

To a suspension of 1,1'-carbonyl diimidazole (2.84 g, 17.5 mmol) in anhydrous THF (15 mL) at 65° C. was added a suspension of 1-(6-(2-chlorophenyl)-5-(4-chlorophenyl)pyridazin-3)hydrazine (1.16 g, 3.5 mmol) in THF (20 mL). After addition, the reaction mixture was stirred at 65° C. for 20 min. Analysis by HPLC/MS indicated the starting material had been consumed. After cooling to room temperature, the reaction was concentrated under reduced pressure. The obtained residue was dissolved in EtOAc (20 mL), and the resulting solution was adjusted to pH 6-8 by slow addition of iced cooled 1N aqueous HCl. The resulting yellow suspension was filtered. The collected solid was washed with water (20 mL×2), EtOAc (10 mL×2), and dried in air to obtain 850 mg of the title compound as a yellow solid. The filtrate was extracted with EtOAc (20 mL×2). The combined EtOAc extracts were washed with saturated aqueous NaCl, dried (Na$_2$SO$_4$), filtered and concentrated under reduced pressure. The obtained residue was triturated with EtOAc (10 mL), and the resulting yellow precipitate was collected by filtration. The collected solid was washed with EtOAc/hexanes (1:2) (10 mL×2) and dried in air to afford additional 150 mg of the title compound (1.0 g in total, 80% yield). HPLC/MS (method A): retention time 3.24 min, (M+H)$^+$=357.0. $^1$H NMR (DMSO-d$_6$, 400 MHz): δ 12.92 (s, 1H), 7.92 (s, 1H), 7.62-7.70 (m, 1H), 7.35-7.50 (m, 3H), 7.33 (d, J=8.0 Hz, 2H), 7.20 (d, J=8.0 Hz, 2H).

1H. Preparation of 3-chloro-6-(2-chlorophenyl)-7-(4-chlorophenyl)-[1,2,4]triazolo[4,3-b]pyridazine

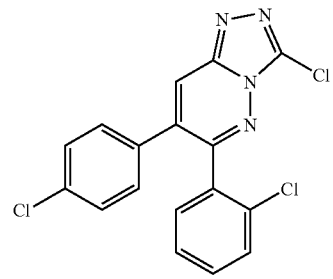

A suspension of 6-(2-chlorophenyl)-7-(4-chlorophenyl)-[1,2,4]triazolo[4,3-b]pyridazin-3(2H)-one (1.0 g, 2.8 mmol) in phosphorus oxychloride (10 mL) was stirred at 130° C. for 6 h. Analysis by HPLC/MS indicated the starting material had been consumed. After cooling to room temperature, the reaction mixture was concentrated under reduced pressure. The obtained residue was diluted with CH$_2$Cl$_2$, the resulting solution washed with saturated aqueous NaHCO$_3$, saturated aqueous NaCl, dried (Na$_2$SO$_4$) and concentrated under reduced pressure to afford 1.1 g (100%) of the title compound as an off-white solid. HPLC/MS (method A): retention time=3.52 min, (M+H)$^+$=375.0.

1I. Preparation of 6-(2-chlorophenyl)-7-(4-chlorophenyl)-N-cyclohexyl-[1,2,4]triazolo[4,3-b]pyridazin-3-amine

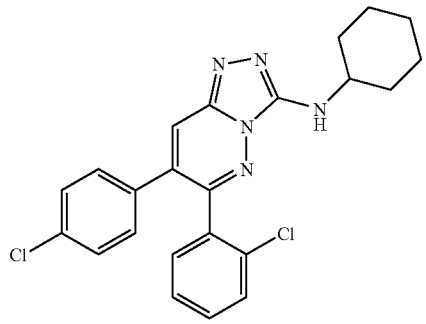

A suspension of 3-chloro-6-(2-chlorophenyl)-7-(4-chlorophenyl)-[1,2,4]triazolo[4,3-b]pyridazine (38 mg, 0.1 mmol) in cyclohexylamine (0.5 mL) was stirred at 100° C. for 16 h. After cooling to room temperature, the reaction mixture was concentrated under reduced pressure. The residue was diluted with EtOAc (30 mL), washed with H$_2$O, saturated aqueous NaCl, dried (Na$_2$SO$_4$), filtered and concentrated under reduced pressure. The crude product was purified using a silica gel cartridge (12 g) eluting with a gradient of EtOAc (40-100%) in hexanes to afford 18 mg (41%) of the title compound as a yellow powder. HPLC/MS (method A): retention time=3.58 min, (M+H)$^+$=438.1. $^1$H NMR (CDCl$_3$, 400 MHz): δ 7.87 (s, 1H), 7.35-7.43 (m, 3H), 7.30-7.33 (m, 1H), 7.20 (d, J=8.56 Hz, 2H), 7.04 (d, J=8.31 Hz, 2H), 4.83 (s, 1H), 3.98 (s, 1H), 2.22-2.25 (m, 2H), 1.79 (dd, J=9.78, 3.67 Hz, 2H), 1.63-1.72 (m, 1H), 1.41-1.52 (m, 2H), 1.27-1.39 (m, 2H), 1.21-1.26 (m, 1H).

Example 2

Preparation of 6-(2-chlorophenyl)-7-(4-chlorophenyl)-3-piperidin-1-yl)-[1,2,4]triazolo[4,3-b]pyridazine

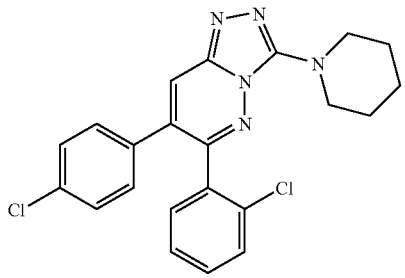

A suspension of 3-chloro-6-(2-chlorophenyl)-7-(4-chlorophenyl)-[1,2,4]triazolo[4,3-b]pyridazine (22 mg, 0.06 mmol) in piperidine (0.5 mL) was stirred at 100° C. for 16 h. After cooling to room temperature, the reaction mixture was concentrated under reduced pressure. The crude product was purified using reverse phase preparative HPLC (Conditions; Phenomenex Luna 5μ C18 21.2×100 mm; Eluted with 60% to 100% B, 8 min gradient, 100% B hold for 7 min, (A=90% H$_2$O, 10% MeOH, 0.1% trifluoroacetic acid and B=10% H$_2$O, 90% MeOH, 0.1% trifluoroacetic acid); Flow rate at 20 mL/min, UV detection at 220 nm). The desired fractions were concentrated under reduced pressure. The residue was dissolved in EtOAc, washed with saturated aqueous NaHCO$_3$, water, saturated aqueous NaCl, dried (Na$_2$SO$_4$), filtered and concentrated under reduced pressure. The residue was lyophilized in acetonitrile to afford 12 mg (48%) of the title compound as a yellow powder. HPLC/MS (method A): retention time=3.82 min, (M+H)$^+$=424.1. $^1$H NMR (CDCl$_3$, 400 MHz): δ7.92 (s, 1H), 7.29-7.39 (m, 4H), 7.21 (d, J=8.56 Hz, 2H), 7.04 (d, J=8.56 Hz, 2H), 3.66 (s, 4H), 1.72-1.81 (m, 4H), 1.69 (d, J=4.89 Hz, 2H).

Example 3

Preparation of 1-(6-(2-chlorophenyl)-7-(4-chlorophenyl)-[1,2,4]triazolo[4,3-b]pyridazin-3-yl)-3-(ethylamino)pyrrolidine-3-carboxamide

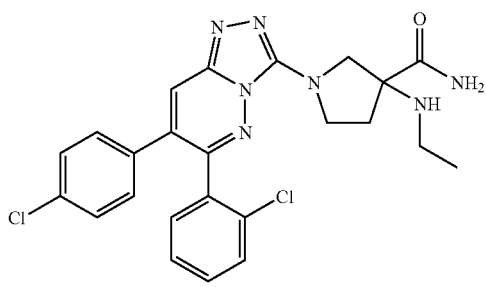

A suspension of 3-chloro-6-(2-chlorophenyl)-7-(4-chlorophenyl)-[1,2,4]triazolo[4,3-b]pyridazine (113 mg, 0.3 mmol) and 3-(ethylamino)pyrrolidine-3-carboxamide (94 mg, 0.6 mmol) in ethylene glycol (2 mL) was stirred at 110° C. for 2 h. Analysis by HPLC/MS indicated the reaction was not complete. Additional 3-(ethylamino)pyrrolidine-3-carboxamide (47 mg, 0.3 mmol) was added. The reaction continued at 110° C. for 1 h more. After cooling to room temperature, the reaction mixture was loaded onto a silica gel cartridge (12 g), eluted with a gradient of MeOH (0-6%) in CH$_2$Cl$_2$ to obtain 40 mg of desired product with 90% purity. The product was further purified using reverse phase preparative HPLC (Conditions: Phenomenex Luna 5μ C18 21.2×100 mm; Eluted with 40% to 90% B, 8 min gradient, 90% B hold for 3 min, (A=90% H$_2$O, 10% MeOH, 0.1% trifluoroacetic acid and B=10% H$_2$O, 90% MeOH, 0.1% trifluoroacetic acid); Flow rate at 20 mL/min, UV detection at 220 nm) to yield the product as a TFA salt. The product was dissolved in EtOAc, washed with saturated aqueous NaHCO$_3$, water, saturated aqueous NaCl, dried (Na$_2$SO$_4$), filtered and concentrated under reduced pressure. The residue was lyophilized in acetonitrile to afford 30 mg (20%) of the title compound as a yellow powder. HPLC/MS (method A): retention time=2.75 min, (M+H)$^+$=496.2. $^1$H NMR (CDCl$_3$, 400 MHz): δ 7.81 (s, 1H), 7.28-7.38 (m, 4H), 7.19-7.26 (m, 2H), 7.01-7.07 (m, 2H), 5.39 (s, 1H), 4.00-4.15 (m, 5H), 2.54-2.65 (m, 3H), 2.12 (m, 1H), 1.40-1.55 (m, 1H), 1.10 (t, J=7.09 Hz, 3H).

Example 4

Preparation of 1-(6-(2-chlorophenyl)-7-(4-chlorophenyl)-[1,2,4]triazolo[4,3-b]pyridazin-3-yl)-3-(ethylamino)azetidine-3-carboxamide

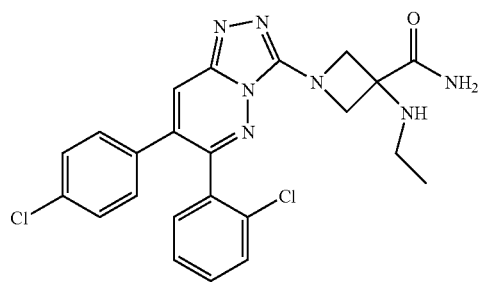

The title compound (70 mg, 32%) as a yellow powder was prepared from 3-chloro-6-(2-chlorophenyl)-7-(4-chlorophenyl)-[1,2,4]triazolo[4,3-b]pyridazine (168 mg, 0.45 mmol) and 3-(ethylamino)azetidine-3-carboxamide (291 mg, 1.35 mmol) in a manner analogous to that in which 1-(6-(2-chlorophenyl)-7-(4-chlorophenyl)-[1,2,4]triazolo[4,3-b]pyridazin-3-yl)-3-(ethylamino)pyrrolidine-3-carboxamide was prepared. HPLC/MS (method A): retention time=2.76 min, (M+H)$^+$=482.2. $^1$H NMR (DMSO-d$_6$, 400 MHz): δ 8.19 (s, 1H), 7.59-7.64 (m, 1H), 7.39-7.48 (m, 3H), 7.28-7.37 (m, 3H), 7.17-7.25 (m, 3H), 4.44 (d, J=8.07 Hz, 2H), 4.08 (d, J=8.07 Hz, 2H), 2.84 (bs, 1H), 2.41 (m, 2H), 1.02 (t, J=7.09 Hz, 3H).

Example 5

Preparation of 6-(2-chlorophenyl)-7-(4-chlorophenyl)-3-(cyclohexyloxy)-[1,2,4]triazolo[4,3-b]pyridazine

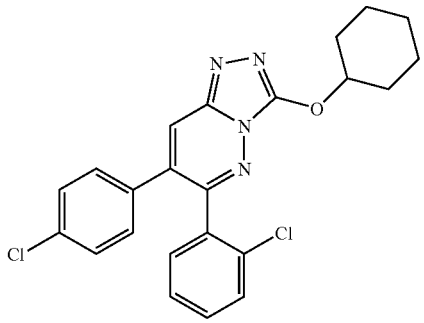

To a solution of cyclohexanol (0.5 g, 5 mmol) in anhydrous THF (1 mL) at room temperature was added freshly cut sodium metal (35 mg, 1.5 mmol). The reaction mixture was stirred at room temperature for 20 min, then at 60° C. for 30 min, and then allowed to cool to room temperature. Into this mixture was added 3-chloro-6-(2-chlorophenyl)-7-(4-chlorophenyl)-[1,2,4]thiazolo[4,3-b]pyridazine (115 mg, 0.3 mmol), the resulting mixture was stirred at room temperature under argon for 16 h. The reaction was carefully quenched by addition of methanol, then diluted with EtOAc. The solution was washed with $H_2O$, saturated aqueous NaCl, dried $Na_2S_4$), filtered and concentrated. The obtained residue was purified using a silica gel cartridge (12 g) eluting with a gradient of EtOAc (0-40%) in hexanes to afford 10 mg (7.6%) of the title compound as a pale-yellow solid. HPLC/MS (method A): retention time=4.06 min, $(M+H)^+$=439.1. $^1$H NMR ($CDCl_3$, 400 MHz): δ 7.84 (s, 1H), 7.46 (dd, J=5.62, 3.67 Hz, 1H), 7.32-7.37 (m, 2H), 7.25-7.30 (m, 1H), 7.20 (d, J=8.56 Hz, 2H), 7.03-7.08 (m, 2H), 5.21-5.29 (m, 1H), 2.28 (d, J=12.96 Hz, 2H), 1.88 (d, J=4.40 Hz, 2H), 1.60-1.80 (m, 3H), 1.45-1.52 (m, 2H), 1.20-1.40 (m, 1H).

Example 6

Preparation of 6-(2-chlorophenyl)-7-(4-chlorophenyl-3-(2,2,2-trifluoroethoxy)-[1,2,4]triazolo[4,3-b]pyridazine

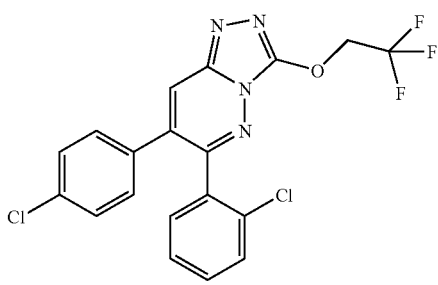

A mixture 3-chloro-6-(2-chlorophenyl)-7-(4-chlorophenyl)-[1,2,4]triazolo[4,3-b]pyridazine (38 mg, 0.1 mmol), 2,2,2-trifluoroethanol (22 μL, 0.2 mmol), 2-tert-butylimino-2-diethylamino-1,3-dimethyl-perhydro-1,3,2-diazaphosphorine (60 μL, 0.3 mmol) and anhydrous THF (0.5 mL) in a sealed tube was stirred at 70° C. for 3 days. After cooling to room temperature, the reaction mixture was concentrated under reduced pressure. The obtained residue was purified using reverse phase preparative HPLC (Conditions: Phenomenex Luna 5μ C18 21.2×100 mm; Eluted with 60% to 100% B, 10 min gradient, 100% B hold for 5 min, (A=90% $H_2O$, 10% MeOH and B=10% $H_2O$, 90% MeOH); Flow rate at 20 mL/min, UV detection at 220 nm) to yield 30 mg of the desired product with 90% purity. The impure product was further purified using a silica gel cartridge (4 g) eluting with a gradient of EtOAc (30-100%) in hexanes to afford 24 mg (55%) of the title compound as a white solid. HPLC/MS (method A): retention time=3.81 min, $(M+H)^+$=439.1. $^1$H NMR ($CDCl_3$, 400 MHz): δ 7.92 (s, 1H), 7.40-7.49 (m, 1H), 7.29-7.33 (m, 2H), 7.14-7.30 (m, 3H), 7.09 (d, J=8.56 Hz, 2H), 5.05-5.07 (m, 2H).

Example 7

Preparation of 6-(2-chlorophenyl)-7-(4-chlorophenyl)-3-(cyclohexylmethyl)-[1,2,4]triazolo[4,3-b]pyridazine

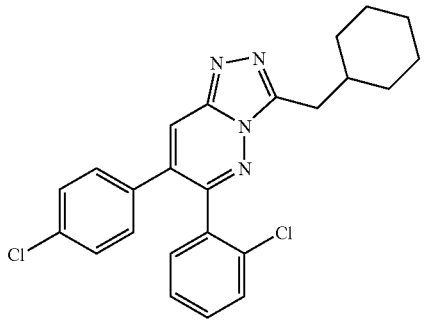

7A. Preparation of N'-(6-(2-chlorophenyl)-5-(4-chlorophenyl)pyridazin-3-yl)-2-cyclohexylacetohydrazide

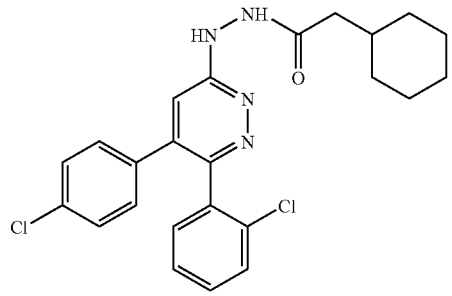

To a solution of cyclohexylacetic acid (85 mg, 0.6 mmol) in THF (3 mL) at 0° C. was added 4-methylmorpholine (86 μL, 0.78 mmol), followed by iso-butyl chloroformate (78 μL, 0.6 mmol) dropwise. The reaction mixture was stirred at 0° C. for 30 min, then a suspension of 1-(6-(2-chlorophenyl)-5-(4-chlorophenyl)pyridazin-3)hydrazine (99 mg, 0.3 mmol) in THF (2 mL) was added to the above mixture. After addition, the reaction mixture was stirred at 0° C. for 1 h, then filtered. The collected solid was washed with EtOAc (20 mL×2). The combined organic was washed with $H_2O$, saturated aqueous NaCl, and concentrated under reduced pressure. The obtained residue was triturated with EtOAc (2 mL×2) to afford 47 mg (34%) of the title compound as an off-white solid. HPLC/MS (method A): retention time=3.53 min, $(M+H)^+$=455.2.

7B. Preparation of 6-(2-chlorophenyl)-7-(4-chlorophenyl)-3-(cyclohexylmethyl)-[1,2,4]triazolo[4,3-b]pyridazine

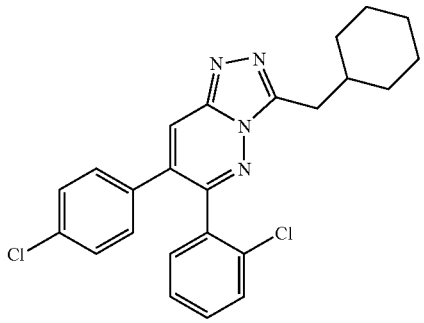

To a suspension of N'-(6-(2-chlorophenyl)-5-(4-chlorophenyl)pyridazin-3-yl)-2-cyclohexylacetohydrazide (46 mg, 0.1 mmol) in THF (2 mL) at room temperature was added diisopropylethylamine (0.14 mL, 0.8 mmol). After 5 min, triphenylphosphine dichloride (110 mg, 0.33 mmol) was added, and the reaction mixture stirred at room temperature for 16 h. Analysis by HPLC/MS indicated the reaction was complete. The reaction was diluted with EtOAc (40 mL), washed with H$_2$O, saturated aqueous NaCl, dried (Na$_2$SO$_4$), filtered and concentrated. The obtained residue was purified using a silica gel cartridge (12 g) eluting with a gradient of EtOAc (0-30%) in hexanes to yield 45 mg of the desired product with 80% purity (contaminated with triphenylphosphine oxide). The product was further purified using reverse phase preparative HPLC (Conditions: Phenomenex Luna 5μ C18 21.2×100 mm; Eluted with 70% to 100% B, 8 min gradient, 100% B hold for 7 min, (A 90% H$_2$O, 10% MeOH and B=10% H$_2$O, 90% MeOH); Flow rate at 20 mL/min, UV detection at 220 nm) to afford 30 mg (68%) of the title compound as a white powder. HPLC/S (method A): retention time=4.22 min, (M+H)$^+$=437.1. $^1$H NMR (CDCl$_3$, 400 MHz): δ 8.03 (s, 1H), 7.33-7741 (m, 4H), 7.21-7.28 (m, 2H), 7.07 (d, J=8.31 Hz, 2H), 3.14 (d, J=7.09 Hz, 2H), 2.01-2.12 (m, 1H), 1.69-1.80 (m, 4H), 1.21-1.29 (m, 3H), 1.10-1.17 (m, 3H).

Example 8

Preparation of 3-benzyl-6-(2-chlorophenyl)-7-(4-chlorophenyl)-[1,2,4]triazolo[4,3]-pyridazine

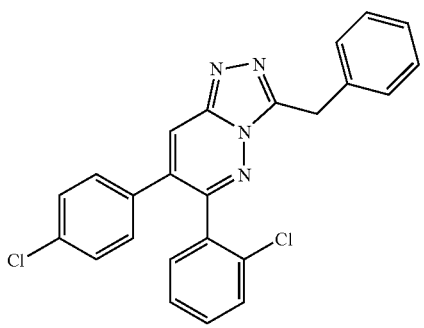

8A. Preparation of N-(6-(2-chlorophenyl)-5-(4-chlorophenyl)pyridazin-3-yl)-2-phenylacetohydrazide

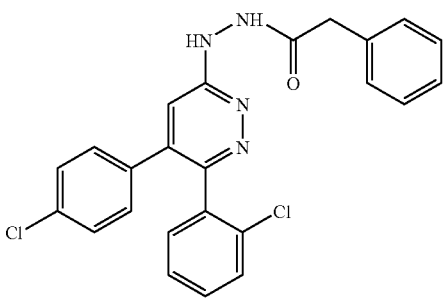

The title compound (42 mg, 47%) as a white foam was prepared from 2-phenylacetic acid (41 mg, 0.3 mmol) and 1-(6-(2-chlorophenyl)-5-(4-chlorophenyl)pyridazin-3)hydrazine (66 mg, 0.2 mmol) according to the procedures described for N'-(6-(2-chlorophenyl)-5-(4-chlorophenyl)pyridazin-3-yl)-2-cyclohexylacetohydrazide (Example 7A). HPLC/MS (method A): retention time=3.30 min, (M+H)$^+$= 449.2.

8B. Preparation of 3-benzyl-6-(2-chlorophenyl)-7-(4-chlorophenyl)-[1,2,4]triazolo[4,3-b]pyridazine

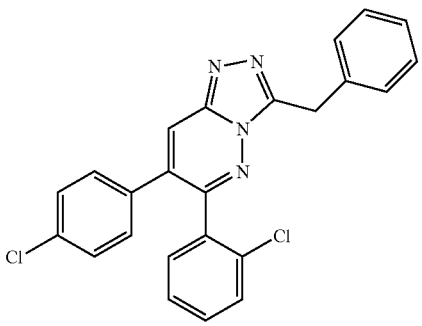

The title compound (20 mg, 54%) as a white powder was prepared from N'-(6-(2-chlorophenyl)-5-(4-chlorophenyl)pyridazin-3-yl)-2-phenylacetohydrazide (38 mg, 0.085 mmol) and triphenylphosphine dichloride (85 mg, 0.26 mmol) according to the procedures described for 6-(2-chlorophenyl)-7-(4-chlorophenyl)-3-(cyclohexylmethyl)-[1,2,4]triazolo[4,3-b]pyridazine (Example 7B). HPLC/MS (method A): retention time=3.92 min. (M+H)$^+$=431.2.

Example 9

Preparation of 6-(2-chlorophenyl)-7-(4-chlorophenyl)-3-(tetrahydro-2H-pyran-4-yl)methyl)-[1,2,4]triazolo[4,3-b]pyridazine

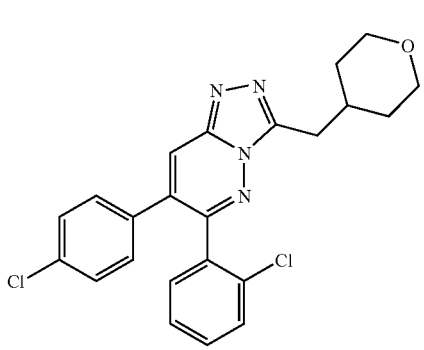

9A. Preparation of N-(6-(2-chlorophenyl)-5-(4-chlorophenyl)pyridazin-3-yl)-2-(tetrahydro-2H-pyran-4-yl)acetohydrazide

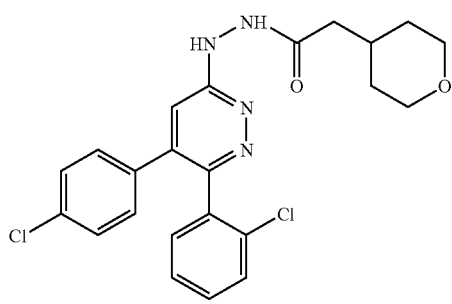

To a solution of 2-(tetrahydro-2H-pyran-4-yl)acetic acid (86.5 mg, 0.6 mmol) in anhydrous DMF (1 mL) was added HOBt (162 mg, 1.2 mmol), followed by EDAC (230 mg, 1.2 mmol). After addition, the reaction mixture was stirred at room temperature for 1.5 h, then a solution of 1-(6-(2-chlorophenyl)-5-(4-chlorophenyl)pyridazin-3-)hydrazine (99 mg, 0.3 mmol) in DMF (2 mL) was added. The mixture was stirred at room temperature for 16 h, then diluted with water, extracted with EtOAc (20 mL×3). The combined organic was washed with saturated aqueous NaCl, dried $Na_2SO_4$) and concentrated under reduced pressure. The crude product was purified using a silica gel cartridge (12 g) eluting with a gradient of EtOAc (20-100%) in hexanes to afford 21 mg (15%) of the title compound as a white foam. HPLC/MS (method A); retention time=2.95 min, $(M+H)^+$=457.2.

9B. Preparation of 6-(2-chlorophenyl)-7-(4-chlorophenyl)-3-(tetrahydro-2H-pyran-4-yl)methyl)-[1,2,4]triazolo[4,3-b]pyridazine

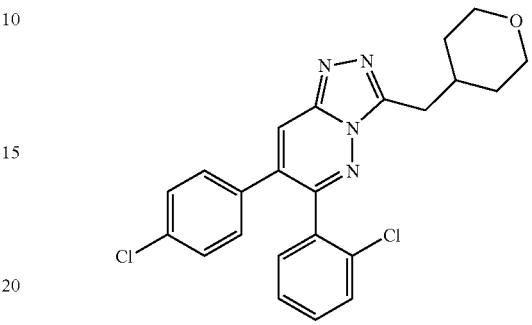

The title compound (8 mg, 40%) as a white powder was prepared from N'-(6-(2-chlorophenyl)-5-(4-chlorophenyl)pyridazin-3-yl)-2-(tetrahydro-2H-pyran-4-yl)acetohydrazide (21 mg, 0.046 mmol) according to the procedures described for 6-(2-chlorophenyl)-7-(4-chlorophenyl)-3-(cyclohexylmethyl)-[1,2,4]triazolo[4,3-b]pyridazine (Example 7B). HPLC/MS (method A): retention time 3.57 min, $(M+H)^+$= 439.2. $^1$H NMR ($CDCl_3$, 400 MHz): δ 8.05 (s, 1H), 7.30-7.42 (m, 4H), 7.23 (d, J=8.31 Hz, 2H), 7.06-7.10 (m, 2H), 3.97 (dd, J=11.62, 2.81 Hz, 2H), 3.41 (td, J=11.74, 1.96 Hz, 2H), 3.21 (d, J=7.09 Hz, 2H), 2.25-2.42 (m, 1H), 1.71 (dd, J=12.84, 1.59 Hz, 2H), 1.43-1.55 (m, 2H).

Example 10

Preparation of 3-(4-chlorobenzyl)-6-(2-chlorophenyl)-7-(4-chlorophenyl)-[1,2,4]triazolo[4,3-b]pyridazine

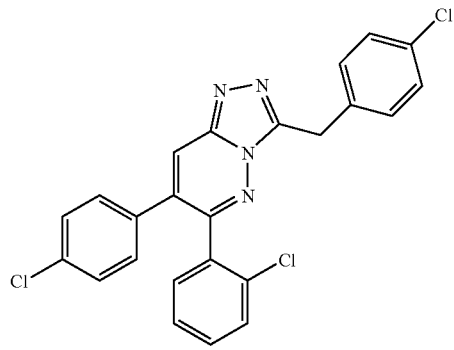

10A. Preparation of 2-(4-chlorophenyl)-N'-(6-(2-chlorophenyl)-5-(4-chlorophenyl)pyridazin-3-yl)acetohydrazide

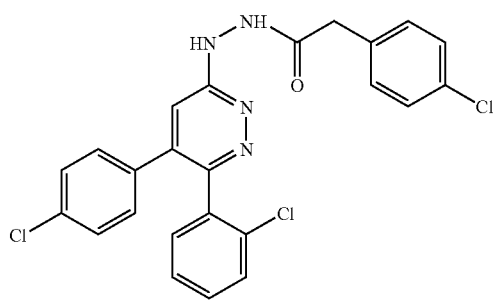

The title compound (90 mg, 62%) as a white solid was prepared from 2-(4-chlorophenyl)acetic acid (62 mg, 0.36 mmol) and 1-(6-(2-chlorophenyl)-5-(4-chlorophenyl)pyridazin-3-yl)hydrazine (99 mg, 0.3 mmol) according to the procedures described for N'-(6-(2-chlorophenyl)-5-(4-chlorophenyl)pyridazin-3-yl)-2-(tetrahydro-2H-pyran-4-yl)acetohydrazide (Example 9A). HPLC/MS (method A): retention time 3.57 min, $(M+H)^+$ 483.2.

10B. Preparation of 3-(4-chlorobenzyl)-6-(2-chlorophenyl)-7-(4-chlorophenyl)-[1,2,4]triazolo[4,3-b]pyridazine

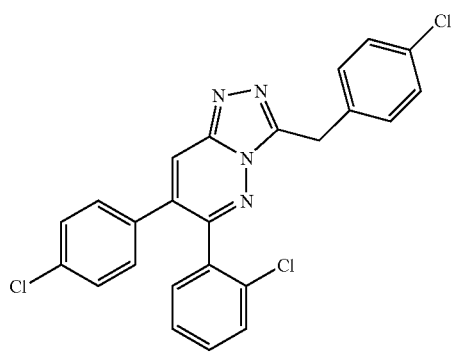

The title compound (50 mg, 54%) as a white powder was prepared from 2-(4-chlorophenyl)-N'-(6-(2-chlorophenyl)-5-(4-chlorophenyl)pyridazin-3-yl)acetohydrazide (96 mg, 0.2 mmol) and triphenylphosphine dichloride (220 mg, 0.66 mmol) according to the procedures described for 6-(2-chlorophenyl)-7-(4-chlorophenyl)-3-(cyclohexylmethyl)-[1,2,4]triazolo[4,3-b]pyridazine (Example 7B), HPLC/MS (method A): retention time=4.12 min, $(M+H)^+$=465.2.

Example 11

Preparation of 6-(2-chlorophenyl)-7-(4-chlorophenyl)-3-(4-(trifluoromethyl)benzyl)-[1,2,4]triazolo[4,3-b]pyridazine

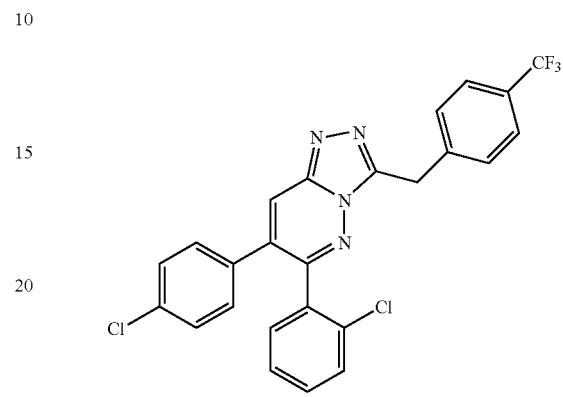

11A. Preparation of N'-(6-(2-chlorophenyl)-5-(4-chlorophenyl)pyridazin-3-yl)-2-(4-(trifluoromethyl)phenyl)acetohydrazide

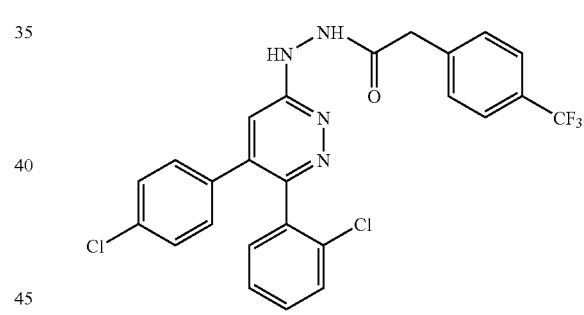

To a solution of 2-(4-(trifluoromethyl)phenyl)acetic acid (98 mg, 0.48 mmol), HOBt (150 mg, 0.78 mmol), diisopropylethylamine (0.18 mL, 1.0 mmol) in anhydrous DMF (2 mL) was added EDAC (105 mg, 0.78 mmol), followed by 1-(6-(2-chlorophenyl)-5-(4-chlorophenyl)pyridazin-3)hydrazine (132 mg, 0.4 mmol). After addition, the reaction mixture was stirred at room temperature for 16 h, then quenched by addition of water. The aqueous mixture was extracted with EtOAc (30 mL×2). The combined organic was washed with saturated aqueous NaCl, dried $(Na_2SO_4)$ and concentrated under reduced pressure. The crude product was purified using a silica gel cartridge (12 g) eluting with a gradient of EtOAc (20-100%) in hexanes to afford 130 mg (63%) of the title compound as a white solid, HPLC/MS (method A): retention time 3.70 min, $(M+H)^+$=571.1.

11B. Preparation of 6-(2-chlorophenyl)-7-(4-chlorophenyl)-3-(4-(trifluoromethyl)benzyl)-[1,2,4]triazolo[4,3-b]pyridazine

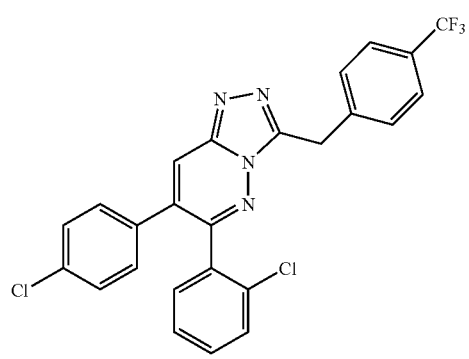

A solution of N'-(6-(2-chlorophenyl)-5-(4-chlorophenyl)pyridazin-3-yl)-2-(4-(trifluoromethyl)phenyl)acetohydrazide (124 mg, 0.24 mmol) and acetic acid (69 µL, 1.2 mmol) in ethanol (2.5 mL) in a vial was heated in a microwave oven at 180° C. for 30 min. After cooling to room temperature, the reaction mixture was diluted with EtOAc, washed with saturated aqueous $NaHCO_3$, saturated aqueous NaCl, dried ($Na_2SO_4$), filtered and concentrated under reduced pressure. The crude product was purified using a silica gel cartridge (12 g) eluting with a gradient of EtOAc (0-70%) in hexanes to obtain 100 mg of the desired product with 96% purity. The product was crystallized from methanol (2 mL) to yield 42 mg of the pure product as a white solid. The mother liquid was concentrated. The obtained residue was purified using reverse phase preparative HPLC (Conditions: Phenomenex Luna 5µ C18 21.2×100 mm; Eluted with 70% to 100% B, 10 min gradient, 100% B hold for 4 min, (A=90% $H_2O$, 10% MeOH and B=10% $H_2O$, 90% MeOH); Flow rate at 20 mL/min, UV detection at 220 nm) to afford additional 48 mg of the title compound as a white powder (90 mg in total, 75% yield). HPLC/MS (method A): retention time=4.08 min, $(M+H)^+$=499.3.

Examples 12 to 26

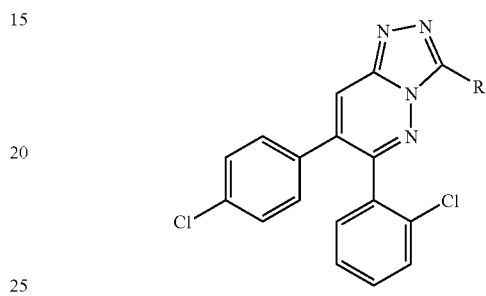

The examples shown below in Table 1 were prepared from 1-(6-(2-chlorophenyl)-5-(4-chlorophenyl)pyridazin-3)hydrazine and the corresponding carboxylic acids (R—$CO_2H$ in Table 1) in a manner analogous to that in which 6-(2-chlorophenyl)-7-(4-chlorophenyl)-3-(4-(trifluoromethyl)benzyl)-[1,2,4]triazolo[4,3-b]pyridazine (Example 11) was prepared.

TABLE 1

| Example | R | R—$CO_2H$ | HPLC/MS (method A) retention time | HPLC/MS $[M + H]^+$ |
|---|---|---|---|---|
| 12 | CF(F)(F)CH₂— | 3,3,3-trifluoro-propanoic acid | 3.63 | 423.1 |
| 13 | —CH₂CH₂CF₃ | 4,4,4-trifluoro-butanoic acid | 3.76 | 437.2 |
| 14 | —CH₂CH(CH₃)CF₃ | 4,4,4-trifluoro-3-methylbutanoic acid | 3.99 | 451.1 |
| 15 | —CH₂N(CH₃)₂ | 2-(dimethylamino)-acetic acid | 2.79 | 398.2 |
| 16 | cyclohexyl | cyclohexane-carboxylic acid | 4.18 | 423.2 |

TABLE 1-continued

| Example | R | R—CO₂H | HPLC/MS (method A) retention time | HPLC/MS [M + H]⁺ |
|---|---|---|---|---|
| 17 | (4-methoxybicyclo[2.2.1]heptyl, OCH₃) | 4-methoxybicyclo[2.2.1]heptane-1-carboxylic acid | 3.88 | 465.2 |
| 18 | (4-methoxybicyclo[2.2.2]octyl, OCH₃) | 4-methoxybicyclo[2.2.2]octane-1-carboxylic acid | 3.91 | 479.3 |
| 19 | (4-(NBoc-piperidinyl)methyl) | 2-(1-(tert-butoxycarbonyl)piperidin-4-yl)acetic acid | 3.93 | 538.1 |
| 20 | (6-chloropyridin-3-yl)methyl | 2-(6-chloropyridin-3-yl)acetic acid | 3.70 | 466.2 |
| 21 | (4-(trifluoromethyl)phenyl)(hydroxy)methyl | 2-hydroxy-2-(4-(trifluoromethyl)phenyl)acetic acid | 3.91 | 515.2 |
| 22 | (S)-phenyl(NHBoc)methyl | (S)-2-(tert-butoxycarbonylamino)-2-phenylacetic acid | 3.67 | 504.3 |
| 23 | (4-(trifluoromethyl)phenyl)(NHBoc)methyl | 2-(tert-butoxycarbonylamino)-2-(4-(trifluoromethyl)phenyl)acetic acid | 4.11 | 614.4 |
| 24 | (6-(trifluoromethyl)pyridin-3-yl)methyl | 2-(6-(trifluoromethyl)pyridin-3-yl)acetic acid | 3.61 | 500.1 |
| 25 | (2-methyl-6-(trifluoromethyl)pyridin-3-yl)methyl | 2-(2-methyl-6-(trifluoromethyl)pyridin-3-yl)acetic acid | 3.70 | 514.2 |
| 26 | (2-methoxy-6-(trifluoromethyl)pyridin-3-yl)methyl | 2-(2-methoxy-6-(trifluoromethyl)pyridin-3-yl)acetic acid | 4.11 | 530.1 |

Example 27

Preparation of (1S)-(6-(2-chlorophenyl)-7-(4-chlorophenyl)-[1,2,4]triazolo[4,3-b]pyridazin-3-yl)(phenyl)methanamine

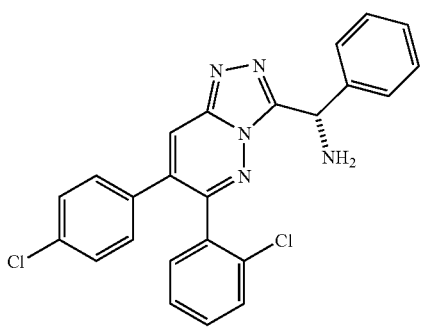

A solution of tert-butyl (1S)-(6-(2-chlorophenyl)-7-(4-chlorophenyl)-[1,2,4]triazolo[4,3-b]pyridazin-3-yl)(phenyl)methylcarbamate (Example 22) (37 mg, 0.068 mmol) in TFA (0.5 mL) and $CH_2CH_2$ (0.5 mL) was stirred at room temperature for 2 h. Analysis by HPLC/MS indicated the reaction was complete. The reaction mixture was concentrated under reduced pressure, and the obtained residue was dissolved in EtOAc. The resulting solution was washed with saturated aqueous $NaHCO_3$, saturated aqueous NaCl, dried ($Na_2SO_4$), filtered and concentrated under reduced pressure to afford 30 mg (100%) of the title compound as an off-white solid. HPLC/MS (method A): retention time=3.11 min, $(M+H)^+$=429.2.

Example 28

Preparation of methyl (1S)-(6-(2-chlorophenyl)-7-(4-chlorophenyl)-[1,2,4]triazolo[4,3-b]pyridazin-3-yl)(phenyl)methylcarbamate

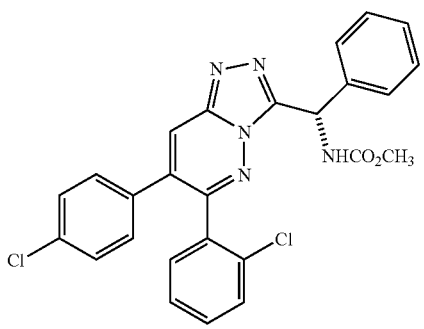

To a solution of (1S)-(6-(2-chlorophenyl)-7-(4-chlorophenyl)-[1,2,4]triazolo[4,3-b]pyridazin-3-yl)(phenyl)methanamine (30 mg, 0.067 mmol) in anhydrous THF (1 mL) at room temperature was added saturated aqueous $NaHCO_3$ solution (1 mL), followed by methyl chloroformate (2 drops). After addition, the reaction mixture was stirred at room temperature for 15 min. Analysis by HPLC/MS indicated the reaction was complete. The reaction mixture was extracted with EtOAc (15 mL×2). The combined organic was washed with saturated aqueous NaCl, dried ($Na_2SO_4$), filtered and concentrated under reduced pressure. The crude product was purified using a silica gel cartridge (12 g) eluting with a gradient of EtOAc (20-100%) in hexanes to afford 25 mg (74%) of the title compound as a white foam. HPLC/MS (method A): retention time=3.67 min, $(M+H)^+$=504.3.

Example 29

Preparation of 6-(2-chlorophenyl)-7-(4-chlorophenyl)-3-(piperidin-4-yl)methyl)-[1,2,4]triazolo[4,3-b]pyridazine, hydrochloride salt

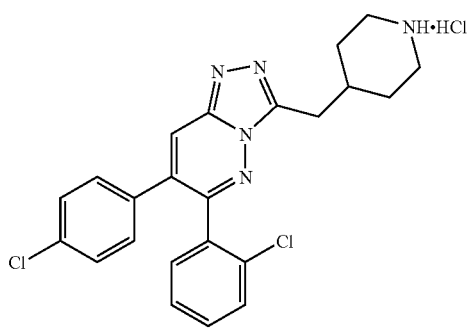

To a solution of tertbutyl 4-((6-(2-chlorophenyl)-7-(4-chlorophenyl)-[1,2,4]triazolo[4,3-b]pyridazin-3-yl)methylpiperidine 1-carboxylate (Example 19) (0.6 g, 1.11 mmol) in $CH_2Cl_2$ (15 mL) was added 2 M HCl in diethyl ether (5 mL. The resulting mixture was stirred at room temperature for 2 h, then concentrated under reduced pressure. The obtained residue was evaporated with $CH_2CH_2$ three times, dried in high vacuum overnight to afford 450 mg (85%) of the title compound as an off-white powder. HPLC/MS (method A): retention time=3.01 min, $(M+H)^+$=438.2.

Example 30

Preparation of 4-(6-(2-chlorophenyl)-7-(4-chlorophenyl)-[1,2,4]triazolo[4,3-b]pyridazin-3-yl)bicyclo[2.2.2]octan-1-ol

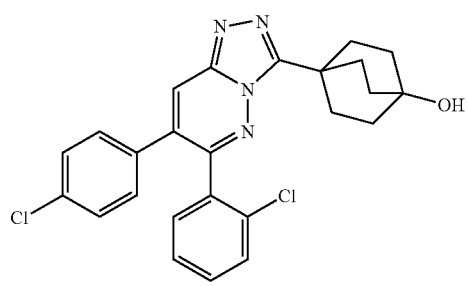

To a suspension of 6-(2-chlorophenyl)-7-(4-chlorophenyl)-3-(4-methoxybicyclo[2.2.2]octan-1-yl)-[1,2,4]triazolo[4,3-b]pyridazine (Example 18) (48 mg, 0.1 mmol) in aqueous (48%) hydrobromic acid solution (0.37 mL) was added dropwise acetic anhydride (0.33 mL). After addition, the reaction tube was sealed, and heated at 120° C. for 16 h. After cooling to room temperature, the reaction mixture was adjusted to pH 7-8 by careful addition of saturated aqueous NaHCO₃, then extracted with EtOAc (10 mL×2). The combined organic was washed with water, saturated aqueous NaCl, dried (Na₂SO₄), filtered and concentrated under reduced pressure. The crude product was purified using reverse phase preparative HPLC (Conditions: Phenomenex Luna 5μ C18 21.2×100 mm; Eluted with 70% to 100% B, 18 min gradient, 100% B hold for 3 min, (A=90% H₂O, 10% MeOH and B=10% H₂O, 90% MeOH); Flow rate at 20 mL/min, UV detection at 220 nm) to afford 35 mg (75%) of the title compound as a white solid. HPLC/MS (method A): retention time 3.61 min, (M+H)⁺=465.2.

Example 31

Preparation of 4-(6-(2-chlorophenyl)-7-(4-chlorophenyl)-[1,2,4]triazolo[4,3-b]pyridazin-3-yl)bicyclo[2.2.1]heptan-1-ol

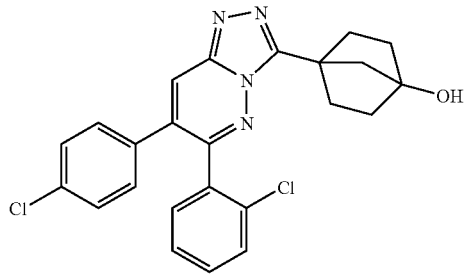

The title compound (36 mg, 79%) as a light yellow foam was prepared from 6-(2-chlorophenyl)-7-(4-chlorophenyl)-3-(4-methoxybicyclo[2.2.1]heptan-1-yl)-[1,2,4]triazolo[4,3-b]pyridazine (Example 17) (47 mg, 0.1 mmol) according to the procedures described for 4-(6-(2-chlorophenyl)-7-(4-chlorophenyl)-[1,2,4]triazolo[4,3-b]pyridazin-3-yl)bicyclo[2.2.2]octan-1-ol (Example 30). HPLC/MS (method A): retention time=3.60 min, (M+H)⁺=451.2.

Example 32

Preparation of 3-((6-(2-chlorophenyl)-7-(4-chlorophenyl)-[1,2,4]triazolo[4,3-b]pyridazin-3-yl)methyl)-6-(trifluoromethyl)pyridin-2-ol

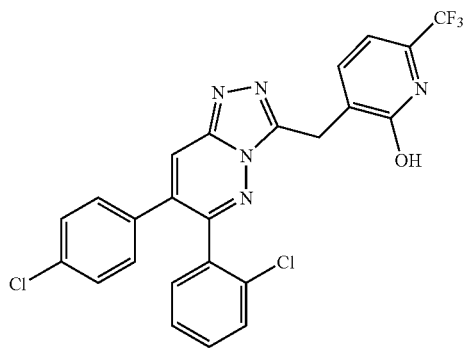

A suspension of 6-(2-chlorophenyl)-7-(4-chlorophenyl)-3-((2-methoxy-6-(trifluoromethyl)pyridin-3-yl)methyl)-[1,2,4]triazolo[4,3-b]pyridazine (Example 26) (100 mg, 0.19 mmol) in aqueous (48%) hydrobromic acid (2 mL) was refluxed for 1 h. After cooling to room temperature, the reaction mixture was adjusted to pH 7-8 by careful addition of saturated aqueous NaHCO₃. The resulting suspension was filtered, and the collected solid was washed with water (10 mL×2), diethyl ether (5 mL), dried in a 50° C. vacuum oven overnight to afford 60 mg (62%) of the title compound as an off-white solid. HPLC/MS (method A): retention time=3.53 min, (M+H)⁺=516.0.

Example 33

Preparation of ethyl 6-(2-chlorophenyl)-7-(4-chlorophenyl)-[1,2,4]triazolo[4,3-b]pyridazine-3-carboxylate

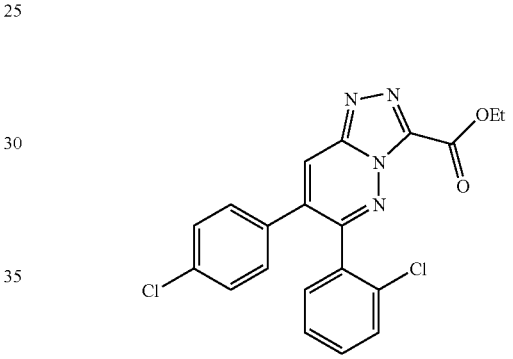

To a solution of 5-(2-chlorophenyl)-4-(4-chlorophenyl)-2-hydrazinylpyridine (258 mg, 0.78 mmol) in THF at room temperature was added acetic acid (0.18 mL, 3.12 mmol), followed by ethyl glyoxylate (0.16 mL, 0.78 mmol). After addition, the reaction mixture was stirred at room temperature for 16 h. Analysis by HPLC/MS indicated the reaction was complete. The reaction was concentrated under reduced pressure. The obtained residue was dissolved in acetic acid (4 mL). To this solution was added sodium acetate (256 mg, 3.12 mmol), followed by dropwise addition of a solution of bromine (36 μL, 0.7 mmol) in acetic acid (0.5 mL). After addition, the reaction mixture was stirred at room temperature for 16 h, then heated in a microwave oven at 150° C. for 15 min. After cooling to room temperature, the reaction mixture was concentrated under reduced pressure. The residue was taken into EtOAc (30 mL), washed with saturated aqueous NaHCO₃, saturated aqueous NaCl, dried (Na₂SO₄) and concentrated. The crude product was purified using a silica gel cartridge (40 g) eluting with a gradient of EtOAc (20-100%) in hexanes to afford 210 mg (65%) of the title compound as an off-white solid. HPLC/MS (method A): retention time=3.53 min, (M+H)⁺=413.2.

Example 34

Preparation of 6-(2-chlorophenyl)-7-(4-chlorophenyl)-N-(4-(trifluoromethyl)benzyl)-[1,2,4]triazolo[4,3-b]pyridazine-3-carboxamide

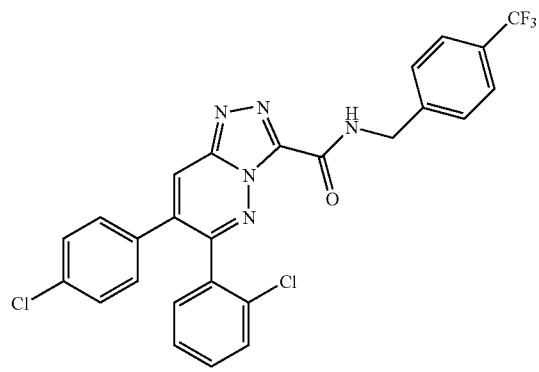

A solution of ethyl 6-(2-chlorophenyl)-7-(4-chlorophenyl)-[1,2,4]triazolo[4,3-b]pyridazine-3-carboxylate (41 mg, 0.10 mmol) and (4-(trifluoromethyl)phenyl)methanamine (29 μL, 0.2 mmol) in methanol (0.5 mL) was stirred at room temperature for 16 h. Analysis by HPLC/MS indicated the staring material had been consumed. The resulting suspension was filtered, the collected solid was washed with hexanes (5 mL×2), dried in air to afford 22 mg (41%) of the title compound as a white solid. HPLC/MS (method A): retention time=3.93 min, (M+H)$^+$=542.2.

Examples 35 to 41

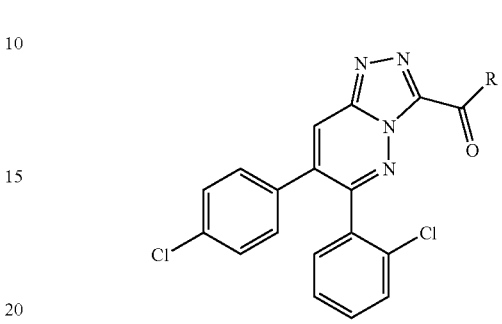

The examples shown below in Table 2 were prepared from ethyl 6-(2-chlorophenyl)-7-(4-chlorophenyl)-[1,2,4]triazolo[4,3-b]pyridazine-3-carboxylate (Example 33) and the corresponding amines in a manner analogous to that in which 6-(2-chlorophenyl)-7-(4-chlorophenyl)-N-(4-(trifluoromethyl)benzyl)-[1,2,4]triazolo[4,3-b]pyridazine-3-carboxamide (Example 34) was prepared.

TABLE 2

| Example | R | Amine | HPLC/MS (method A) retention time | HPLC/MS [M + H]$^+$ |
|---|---|---|---|---|
| 35 | piperidine | piperidine | 3.49 | 452.2 |
| 36 | morpholine | morpholine | 3.17 | 454.2 |
| 37 | piperidin-4-ol | piperidin-4-ol | 3.06 | 468.2 |
| 38 | cyclohexylamine | cyclohexylamine | 3.84 | 466.2 |
| 39 | cyclohexyl-methanamine | cyclohexyl-methanamine | 4.00 | 480.3 |

TABLE 2-continued

| Example | R | Amine | HPLC/MS (method A) retention time | HPLC/MS [M + H]+ |
|---|---|---|---|---|
| 40 | ![structure] | benzylamine | 3.90 | 474.3 |
| 41 | ![structure] | 2-phenylethanamine | 4.05 | 488.3 |

Example 42

Preparation of (4-benzylpiperidin-1-yl)(6-(2-chlorophenyl)-7-(4-chlorophenyl)-[1,2,4]triazolo[4,3-b]pyridazin-3-yl)methanone

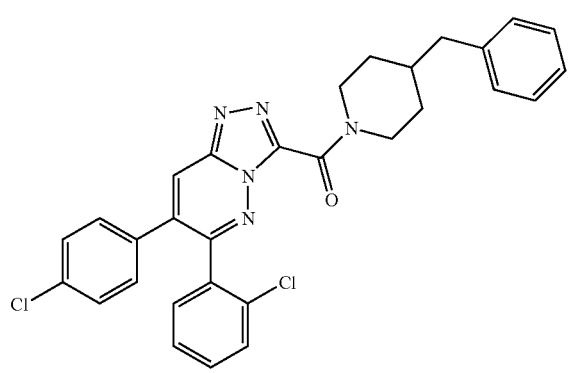

A solution of ethyl 6-(2-chlorophenyl)-7-(4-chlorophenyl)-[1,2,4]triazolo[4,3-b]pyridazine-3-carboxylate (21 mg, 0.05 mmol) and 4-benzylpiperidine (0.175 mL, 1.0 mmol) in methanol (0.5 mL) was heated in a microwave oven at 160° C. for 30 min. After cooling to room temperature, the reaction mixture was concentrated under reduced pressure, then the crude product was purified using reverse phase preparative HPLC (Conditions: Water SunFire Prep C18, OBD 19×100 m, 5 μm; Fluted with 0% to 100% B, 10 min gradient, 100% B hold for 5 min, (A 90% H$_2$O, 10% MeOH, 0.1% of TEA and B 10% H$_2$O, 90% MeOH, 0.1% of TFA); Flow rate at 20 mL/min, UV detection at 220 nm) to afford 18 mg (66%) of the title compound as a white powder. HPLC/MS (method A): retention time=4.12 min, (M+H)+=542.1.

Examples 43 to 52

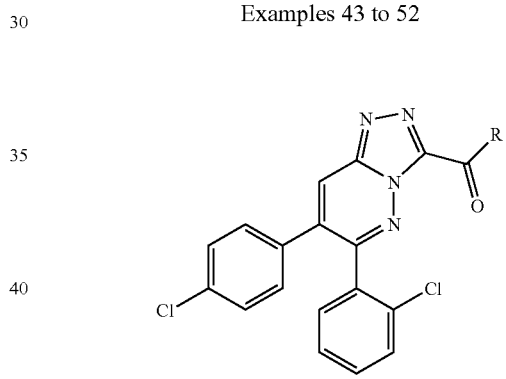

The examples shown below in Table 3 were prepared from ethyl 6-(2-chlorophenyl)-7-(4-chlorophenyl)[1,2,4]triazolo[4,3-b]pyridazine-3-carboxylate (Example 33) and the corresponding amines in a manner analogous to that in which (4-benzylpiperidin-1-yl)(6-(2-chlorophenyl)-7-(4-chlorophenyl)-[1,2,4]triazolo[4,3-b]pyridazin-3-yl)methanone (Example 42) was prepared.

TABLE 3

| Example | R | Amine | HPLC/MS (method A) retention time | HPLC/MS [M + H]+ |
|---|---|---|---|---|
| 43 | ![structure] | pentan-3-amine | 3.78 | 454.2 |

TABLE 3-continued
| Example | R | Amine | HPLC/MS (method A) retention time | HPLC/MS [M + H]+ |
|---|---|---|---|---|
| 44 | 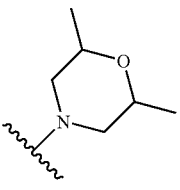 | 2,6-dimethyl morpholine | 3.55 | 482.1 |
| 45 | 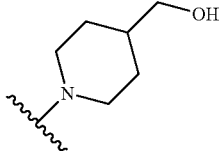 | piperidin-4-ylmethanol | 3.26 | 482.2 |
| 46 | 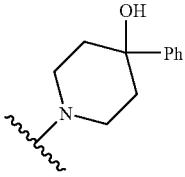 | 4-phenyl-piperidin-4-ol | 3.64 | 544.1 |
| 47 | 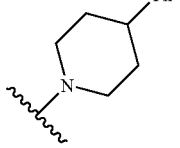 | 4-phenylpiperidine | 3.87 | 528.2 |
| 48 | 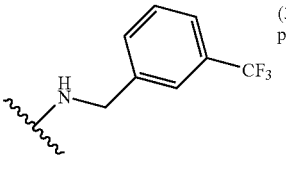 | (3-(trifluoromethyl)phenyl)methanamine | 3.92 | 542.1 |
| 49 | 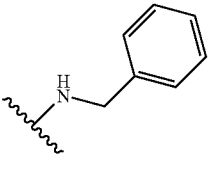 | benzylamine | 3.73 | 474.1 |
| 50 | 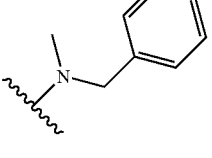 | N-methyl-benzylamine | 3.70 | 488.1 |
| 51 |  | 2-phenylethanamine | 3.80 | 488.1 |
| 52 | 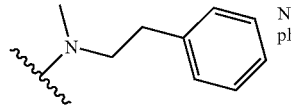 | N-methyl-2-phenylethanamine | 3.75 | 502.1 |

Example 53

Preparation of 6-(2-chlorophenyl)-7-(4-chlorophenyl)-N-methyl-N-(4-(trifluoromethyl)benzyl)-[1,2,4]triazolo[4,3-b]pyridazine-3-carboxamide

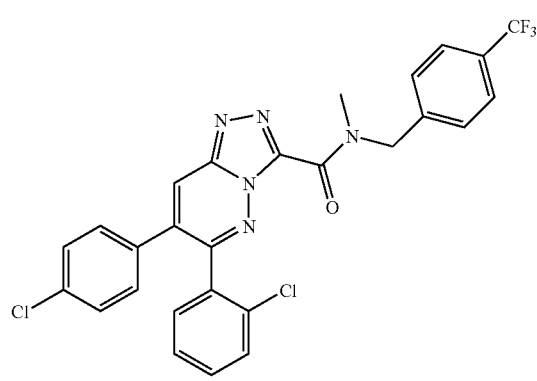

To a solution of 6-(2-chlorophenyl)-7-(4-chlorophenyl)-N-(4-(trifluoromethyl)benzyl)-[1,2,4]triazolo[4,3-b]pyridazine-3-carboxamide (Example 34) (22 mg, 0.041 mmol) in anhydrous DMF at room temperature was added sodium hydride (6.5 mg, 0.164 mmol). The resulting suspension was stirred at room temperature for 5 min, then iodomethane (25 μL, 0.4 mmol) was added. The reaction mixture was stirred at room temperature for 1 h. The mixture was diluted with EtOAc (30 mL), washed with water, saturated aqueous NaCl, dried (Na$_2$SO$_4$) and concentrated under reduced pressure. The crude product was purified using a silica gel cartridge (4 g) eluting with a gradient of EtOAc (0-60%) in hexanes to afford 15 mg (66%) of the title compound as a white powder. HPLC/MS (method A): retention time=3.85 min, (M+H)$^+$=556.3

Example 54

Preparation of 6-(2-chlorophenyl)-7-(4-chlorophenyl)-3-((2-methyl-6-(trifluoromethylpyridin-3-yl)methyl)-[1,2,4]triazolo[4,3-a]pyridine

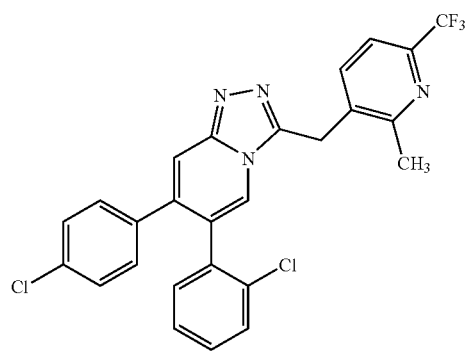

54A. Preparation of 5-chloro-4-(4-chlorophenyl)-2-fluoropyridine

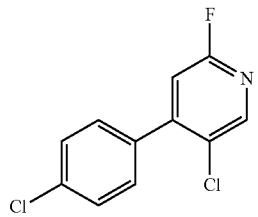

A suspension of 5-chloro-2-fluoro-4-iodopyridine (2.57 g, 10 mmol), 4-chlorophenylboronic acid (1.72 g, 11 mmol) and Pd(Ph$_3$P)$_4$ (462 mg, 0.4 mmol) in a mixture of 2.0 M aqueous sodium carbonate (6 mL) and toluene (10 mL) was heated at 140° C. in a microwave oven for 30 min. Analysis by HPLC/MS indicated that the reaction was not complete. Additional 4-chlorophenylboronic acid (0.156 g, 1 mmol) was added, followed by Pd(Ph$_3$P)$_4$ (116 mg, 0.1 mmol). The reaction mixture was again heated at 140° C. in a microwave oven for 30 min. After cooling to room temperature, the reaction mixture was diluted with water and extracted with EtOAc (50 mL×3). The combined EtOAc extracts were washed with saturated aqueous NaCl, dried over Na$_2$SO$_4$, filtered and concentrated under reduced pressure. The crude product was purified using a silica gel cartridge (120 g) eluted with a gradient of EtOAc (0-50%) in hexanes to afford 2.6 g of the product (60% pure) as an off-white solid. This was crystallized in EtOAc-hexanes to obtain the pure title compound (0.9 g) as a white solid. HPLC/MS: retention time=3.80 min, [M+H]$^+$=242.0.

54B. Preparation of 5-(2-chlorophenyl)-4-(4-chlorophenyl)-2-fluoropyridine

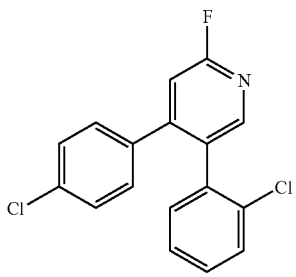

To a flame-dried tube was placed 5-chloro-4-(4-chlorophenyl)-2-fluoropyridine (0.71 g, 2.93 mmol), 2-chlorophenylboronic acid (0.55 g, 3.52 mmol), K$_3$PO$_4$ (1.24 g, 5.86 mmol), Pd$_2$(dba)$_3$ (0.134 g, 0.147 mmol), and S-Phos (0.12 g, 0.29 mmol). The reaction vessel was then purged with argon three times before degassed toluene (15 mL) was added in, and sealed. The reaction mixture was stirred at 95° C. for 16 h. Analysis by HPLC/MS indicated the reaction was complete. After cooling to room temperature, the reaction mixture was partitioned between EtOAc and water. The aqueous layer was extracted with EtOAc (30 mL×3). The combined organic was washed with saturated aqueous NaCl, dried over Na$_2$SO$_4$, filtered and concentrated under reduced pressure. The crude product was purified using a silica gel cartridge (80 g) eluting with a gradient of EtOAc (0-10%) in hexanes to afford 0.33 g (35%) of the title compound as a white foam. HPLC/MS: retention time=4.03 min, [M+H]⁺=318.1.

54C. Preparation of 5-(2-chlorophenyl)-4-(4-chlorophenyl)-2-hydrazinylpyridine

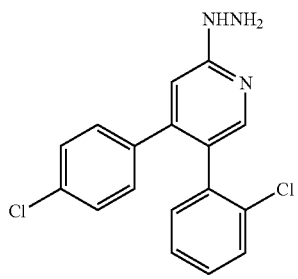

To a suspension of 5-(2-chlorophenyl)-4-(4-chlorophenyl)-2-fluoropyridine (0.32 g, 1 mmol) in pyridine (4 mL) at room temperature was added anhydrous hydrazine (1 mL). The resulting mixture was stirred at 90° C. for 1 h. Analysis by HPLC/MS indicated the reaction was complete. After cooling to room temperature, the reaction mixture was concentrated under reduced pressure. To the residue was added water, and the resulting suspension was extracted with EtOAc (50 mL×3). The combined EtOAc extracts were washed with saturated aqueous NaCl, dried over Na₂SO₄, filtered and concentrated under reduced pressure to afford 0.28 g (85%) of the title compound as a white foam. HPLC/MS: retention time=3.03 min, [M+H]⁺=330.1.

54D. Preparation of N'-(5-(2-chlorophenyl)-4-(4-chlorophenyl)pyridin-2-yl)-2-(2-methyl-6-(trifluoromethyl)pyridin-3-yl)acetohydrazide

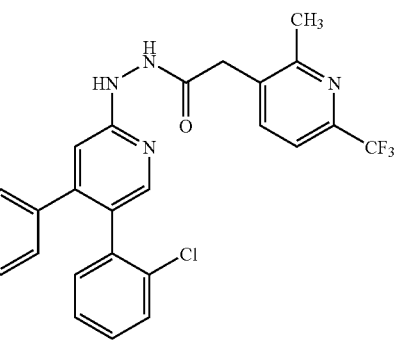

The title compound (80 mg, 99%) as a white solid was prepared from 5-(2-chlorophenyl)-4-(4-chlorophenyl)-2-hydrazinylpyridine (50 mg, 0.15 mmol) and 2-(2-methyl-6-(trifluoromethyl)pyridin-3-yl)acetic acid (49.3 mg, 0.225 mmol) in a manner analogous to that in which N'-(6-(2-chlorophenyl)-5-(4-chlorophenyl)pyridazin-3-yl)-2-(4-(trifluoromethyl)phenyl)acetohydrazide (Example 11A) was prepared. HPLC/MS: retention time=3.63 min, [M+H]⁺=531.1.

54E. Preparation of 6-(2-chlorophenyl)-7-(4-chlorophenyl)-3-((2-methyl-6-(trifluoromethylpyridin-3-yl)methyl)-[1,2,4]triazolo[4,3-a]pyridine

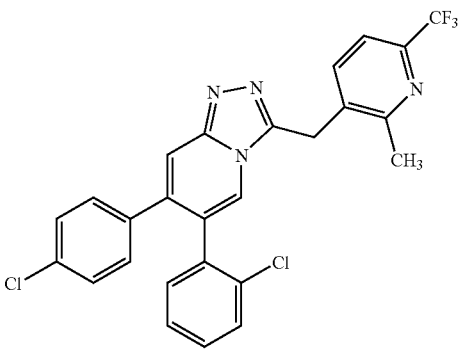

A solution of N-(5-(2-chlorophenyl)-4-(4-chlorophenyl)pyridin-2-yl)-2-(2-methyl-6-(trifluoromethyl)pyridin-3-yl)acetohydrazide (80 mg, 0.15 mmol) and acetic acid (0.5 mL) in ethanol (1 mL) was heated in a microwave oven at 180° C. for 30 min. Analysis by HPLC/MS indicated about 40% of starting material remained. The reaction mixture was heated again in a microwave oven at 180° C. for additional 30 min. After cooling to room temperature, the reaction mixture was concentrated under reduced pressure. The obtained residue was taken into EtOAc, and the solution was washed with saturated aqueous NaHCO₃, saturated aqueous NaCl, dried (Na₂SO₄), filtered and concentrated under reduced pressure. The crude product was purified using reverse phase preparative HPLC (Conditions: Phenomenex Luna 5μ C18 21.2×100 mm; Eluted with 70% to 100% B, 10 min gradient, 100% B hold for 4 min, (A=90% H₂O, 10% MeOH and B=10% H₂O, 90% MeOH); Flow rate at 20 mL/min, UV detection at 220 nm) to yield the desired product with about 64% purity. The product was further purified using a silica gel cartridge (12 g) eluting with a gradient of EtOAc (0-70%) in hexanes to afford 18 mg (23%) of the title compound. HPLC/MS (method A): retention time=3.91 min, (M+H)⁺=513.1.

Example 55

Preparation of 6-(2-chlorophenyl)-7-(4-chlorophenyl)-3-((6-(trifluoromethylpyridin-3-yl)methyl)-[1,2,4]triazolo[4,3-a]pyridine

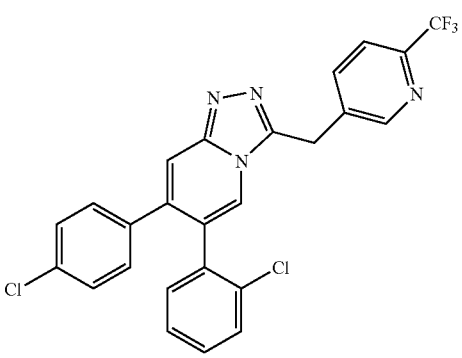

55A. Preparation of N'-(5-(2-chlorophenyl)-4-(4-chlorophenyl)pyridin-2-yl)-2-(6-(trifluoromethyl)pyridin-3-yl)acetohydrazide

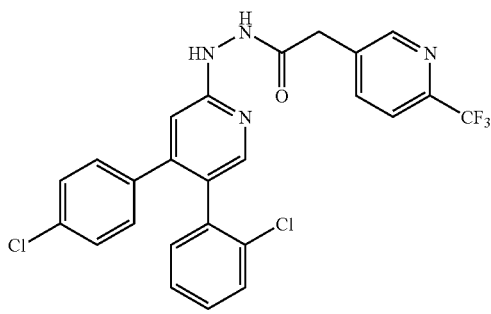

The title compound (40 mg, 100%) as a white solid was prepared from 5-(2-chlorophenyl)-4-(4-chlorophenyl)-2-hydrazinylpyridine (25 mg, 0.075 mmol) and 2-(6-(trifluoromethyl)pyridin-3-yl)acetic acid (23 mg, 0.113 mmol) in a manner analogous to that in which N'-(6-(2-chlorophenyl)-5-(4-chlorophenyl)pyridazin-3-yl)-2-(4-(trifluoromethyl)phenyl) acetohydrazide (Example 11A) was prepared. HPLC/MS: retention time=3.53 min, [M+H]$^+$=517.1.

55B. Preparation of 6-(2-chlorophenyl)-7-(4-chlorophenyl)-3-((6-(trifluoromethylpyridin-3-yl)methyl)-[1,2,4]triazolo[4,3-a]pyridine

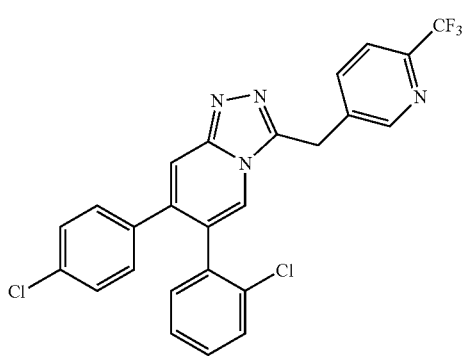

A solution of N-(5-(2-chlorophenyl)-4-(4-chlorophenyl)pyridin-2-yl)-2-(6-(trifluoromethyl)pyridin-3-ylacetohydrazide (40 mg, 0.075 mmol) and acetic acid (0.25 mL) in ethanol (0.5 mL) was heated in a microwave oven at 180° C. for 45 min. After cooling to room temperature, the reaction mixture was concentrated under reduced pressure. The obtained residue was taken into EtOAc, and the solution was washed with saturated aqueous NaHCO$_3$, saturated aqueous NaCl, dried (Na$_2$SO$_4$), filtered and concentrated under reduced pressure. The crude product was purified using a silica gel cartridge (12 g) eluting with a gradient of EtOAc (0-70%) in hexanes to obtain the product with about 85% purity as an oil. The product was further purified using reverse phase preparative HPLC (Conditions: Phenomenex Luna 5µ C18 21.2×100 mm; Eluted with 50% to 100% B, 10 min gradient, 100% B hold for 4 min, (A=90% H$_2$O, 10% MeOH, 0.1% TFA and B=10% H$_2$O, 90% MeOH, 0.1% TFA); Flow rate at 20 mL/min, UV detection at 220 nm) to yield the desired product, which was taken into EtOAc, washed with saturated aqueous NaHCO$_3$, saturated aqueous NaCl, dried over Na$_2$SO$_4$, filtered and concentrated. The residue was lyophilized in acetonitrile to afford 9 mg (24% yield, 99% pure) of the title compound as a white powder. HPLC/MS (method A): retention time=3.88 min, [M+H]$^+$=499.0.

Example 56

Preparation of 7-(4-chlorophenyl)-6-(2,4-dichlorophenyl)-3-((6-(trifluoromethylpyridin-3-yl)methyl)-[1,2,4]triazolo[4,3-a]pyridine

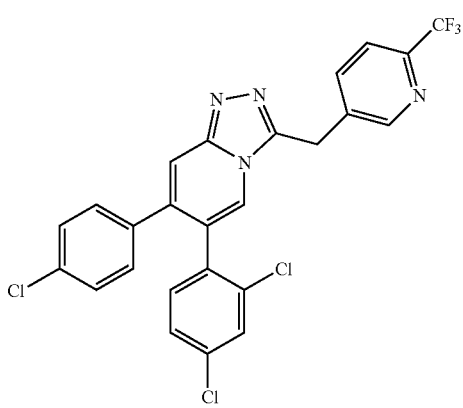

56A. Preparation of 5-bromo-2-chloro-4-(4-chlorophenyl)pyridine

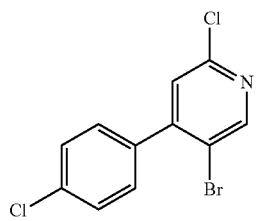

To a degassed solution of 5-bromo-2-chloro-4-iodopyridine (Ref. Cottet, F. and Schlosser, M. *Tetrahedron* 60, 11896-11874 (2004)) (2.0 g, 6.3 mmol), 4-chlorophenylboronic acid (1.1 g, 6.9 mmol) and K$_2$CO$_3$ (1.7 g, 12.6 mmol) in 1,2-dimethoxyethane (24 mL) and H$_2$O (8.0 mL) was added Pd(PPh$_3$)$_4$ (0.727 g, 0.63 mmol) under argon at 20° C. The reaction mixture was refluxed for 15 h under argon, then allowed to cool to 20° C. The reaction was quenched by addition of H$_2$O (30 mL) and extracted with EtOAc (50 mL×3). The combined organic was washed with saturated aqueous NaHCO$_3$ (50 mL) and saturated aqueous NaCl (50 mL), dried over MgSO$_4$, filtered and concentrated in vacuo. The residue was crystallized in EtOH to afford 1.35 g of the title compound as a light beige solid as the first crop. The second crop of the title product (0.44 g) was also isolated by concentrating the mother liquid followed by recrystallization in EtOH. LC/MS (method B): retention time=2.03 min, [M+H]$^+$=301.9.

56B. Preparation of 5-bromo-4-(4-chlorophenyl)-2-hydrazinylpyridine

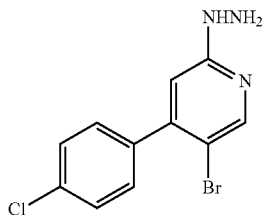

To a solution of 5-bromo-2-chloro-4-(4-chlorophenyl)pyridine (1.3 g, 4.3 mmol) in THF (10 mL) was added hydrazine (1.4 g, 43 mmol). The reaction mixture was refluxed under argon for 4 days, then allowed to cool to 20° C. and concentrated in vacuo. The residue was purified by using reverse phase preparative HPLC (Conditions: Phenomenex Luna 5μ C18 30×100 mm; Eluted with 0% to 100% B, 10 min gradient, 100% B hold for 5 min, (A=90% H$_2$O, 10% CH$_3$CN, 0.1% trifluoroacetic acid and B=10% H$_2$O, 90% CH$_3$CN, 0.1% trifluoroacetic acid); Flow rate at 40 mL/min, UV detection at 220 nm), followed by basification with 1N aqueous NaOH to pH 12 and extraction with CHCl$_3$ to afford 0.82 g (63%) of the title compound as an off-white solid. LC/MS (method B): retention time=1.47 min, [M+H]$^+$=298.0.

56C. Preparation of N'-(5-bromo-4-(4-chlorophenyl)pyridin-2-yl)-2-(6-(trifluoromethyl)pyridin-3-yl)acetohydrazide

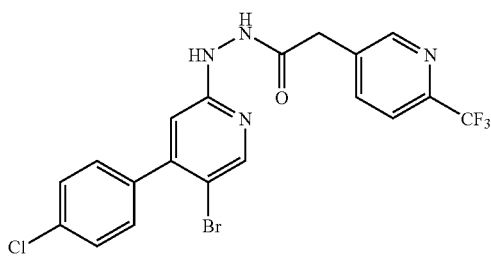

To a suspension of 5-bromo-4-(4-chlorophenyl)-2-hydrazinylpyridine (37 mg, 0.12 mmol), 2-(6-(trifluoromethyl)pyridin-3-yl)acetic acid (26 mg, 0.12 mmol) and bromotripyrrolidinophosphonium hexafluorophosphate (PyBop, 70 mg, 0.13 mmol) in CH$_3$CN (1.0 mL) was added (i-Pr)$_2$EtN (32 mg, 0.25 mmol) at 20° C. The reaction mixture was stirred at 20° C. under argon for 15 h, then concentrated in vacuo. The residue was dissolved in EtOAc (15 mL). The organic solution was successively washed with saturated aqueous NaHCO$_3$ (5 mL) and saturated aqueous NaCl (5 mL), dried over MgSO$_4$, filtered and concentrated in vacuo. The residue was purified using reverse phase preparative HPLC (Conditions: Phemomenex Luna 5μ C18 30×75 mm; Eluted with 0% to 100% B, 10 min gradient, 100% B hold for 2 min, (A=90% H$_2$O, 10% CH$_3$CN, 0.1% trifluoroacetic acid and B=10% H$_2$O, 90% CH$_3$CN, 0.1% trifluoroacetic acid); Flow rate at 40 mL/min, UV detection at 220 nm), followed by basification with 1N aqueous NaOH to pH 12 and extraction with EtOAc to afford 54 mg (92%) of the title compound as a white solid. LC/MS (method B): retention time 1.91 min, [M+H]$^+$=487.0.

56D. Preparation of 6-bromo-7-(4-chlorophenyl)-3-((6-(trifluoromethylpyridin-3-yl)methyl)-[1,2,4]triazolo[4,3-a]pyridine

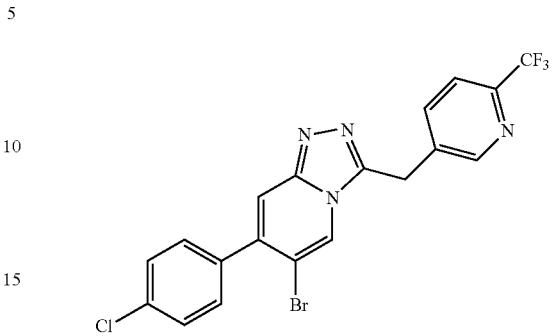

To a suspension of N-(5-bromo-4-(4-chlorophenyl)pyridin-2-yl)-2-(6-(trifluoromethyl)pyridin-3-yl)acetohydrazide (24 mg, 0.05 mmol) in (trifluoromethyl)benzene (0.45 mL) was added glacial acidic acid (0.15 mL). The reaction mixture was sealed and heated in a microwave reactor at 200° C. for 30 min. The reaction mixture was allowed to cool to 20° C. and concentrated in vacuo. The residue was purified using reverse phase preparative HPLC (Conditions: Phemomenex Luna 5μ C18 30×75 mm; Eluted with 0% to 100% B, 10 min gradient, 100% B hold for 2 min, (A=90% H$_2$O, 10% CH$_3$CN, 0.1% trifluoroacetic acid and B=10% H$_2$O, 90% CH$_3$CN, 0.1% trifluoroacetic acid); Flow rate at 40 mL/min, UV detection at 220 nm) to afford 21 mg (90%) of the title compound as a white solid. LC/MS (method B): retention time=1.86 min, [M+H]$^+$=467.0.

56E. Preparation of 7-(4-chlorophenyl)-6-(2,4-dichlorophenyl)-3-((6-(trifluoromethylpyridin-3-yl)methyl)-[1,2,4]triazolo[4,3-a]pyridine

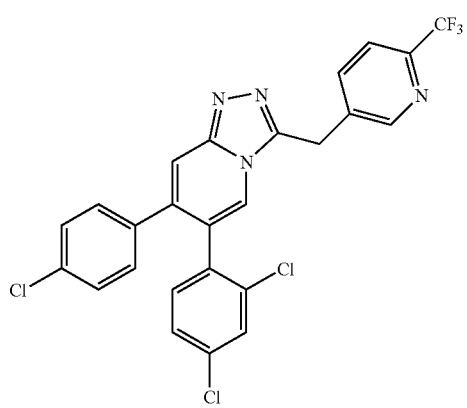

To a degassed solution of 6-bromo-7-(4-chlorophenyl)-3-((6-(trifluoromethyl)pyridin-3-yl)methyl)-[1,2,4]triazolo[4,3-a]pyridine (9.5 mg, 0.02 mmol), 2,4-dichlorophenylboronic acid (8.0 mg, 0.041 mmol) and K$_2$CO$_3$ (8.5 mg, 0.061 mmol) in 1,4-dioxane (0.3 mL) and H$_2$O (0.1 mL) was added Pd(PPh$_3$)$_4$ (2.3 mg, 0.002 mmol) under argon at 20° C. The reaction mixture was heated at 100° C. for 2 h under argon, then allowed to cool to 20° C. The reaction was concentrated in vacuo, and the residue was purified using reverse phase preparative HPLC (Conditions: Phemomenex Luna 5μ C18 30×75 mm; Fluted with 0% to 100% B, 10 min gradient, 100% B hold for 2 min, (A=90% $H_2O$, 10% $CH_3CN$, 0.1% trifluoroacetic acid and B=10% $H_2O$, 90% $CH_3CN$, 0.1% trifluoroacetic acid); Flow rate at 40 mL/min, UV detection at 220 nm) to afford 5.5 mg (55%) of the title compound as a white solid. LC/MS (method B): retention time 2.03 min, $[M+H]^+=533.2$.

Example 57

Preparation of 7-(4-chlorophenyl)-6-(2,4-dichlorophenyl)-3-((2-methyl-6-(trifluoromethyl)pyridin-3-yl)methyl)-[1,2,4]triazolo[4,3-a]pyridine

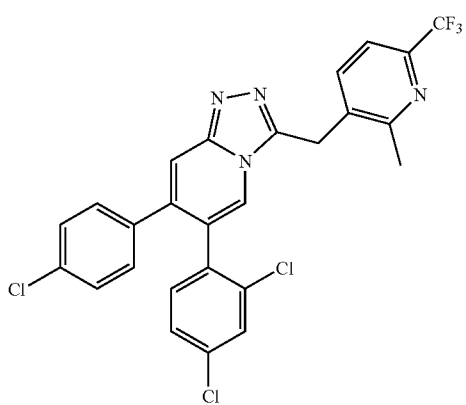

57A. Preparation of N'-(5-bromo-4-(4-chlorophenyl)pyridin-2-yl)-2-(2-methyl-6-(trifluoromethyl)pyridin-3-yl)acetohydrazide

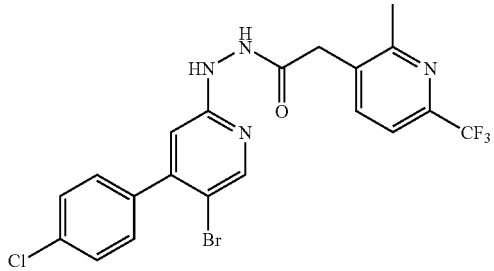

The title compound (160 mg, 97%) as a beige powder was prepared from 5-bromo-4-(4-chlorophenyl)-2-hydrazinylpyridine (100 mg, 0.33 mmol), 2-(2-methyl-6-(trifluoromethyl)pyridin-3-yl)acetic acid (75 mg, 0.33 mmol), (i-Pr)$_2$EtN (86 mg, 0.66 mmol) and bromotripyrrolidinophosphonium hexafluorophosphate (PyBop, 190 mg, 0.37 mmol) in $CH_3CN$ (2.5 mL) by the procedures analogous to those described for N'-(5-bromo-4-(4-chlorophenyl)pyridin-2-yl)-2-(6-(trifluoromethyl)pyridin-3-yl)acetohydrazide (Example 56C). LC/MS (method B): retention time 1.92 min, $[M+H]^+=499.0$.

57B. Preparation of 6-bromo-7-(4-chlorophenyl)-3-((2-methyl-6-(trifluoromethyl)pyridin-3-yl)methyl)-[1,2,4]triazolo[4,3-a]pyridine

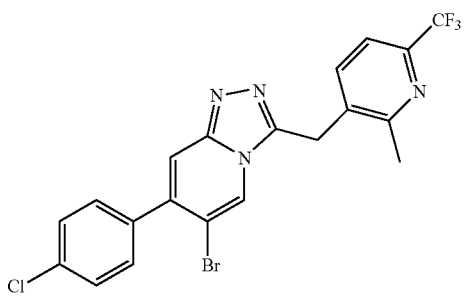

The title compound (61 mg, 60%) as a white powder was prepared from N'-(5-bromo-4-(4-chlorophenyl)pyridin-2-yl)-2-(2-methyl-6-trifluoromethyl)pyridin-3-yl)acetohydrazide (100 mg, 0.20 mmol) in glacial acetic acid (0.6 mL) and (trifluoromethyl)benzene (1.8 mL) by the procedures analogous to those described for 6-bromo-7-(4-chlorophenyl)-3-((6-(trifluoromethyl)pyridin-3-yl)methyl)-[1,2,4]triazolo[4,3-a]pyridine (Example 56D). LC/MS (method B): retention time 1.83 min, $[M+H]^+=481.0$.

57C. Preparation of 7-(4-chlorophenyl)-6-(2,4-dichlorophenyl)-3-((2-methyl-6-(trifluoromethyl) pyridin-3-yl)methyl)-[1,2,4]triazolo[4,3-a]pyridine

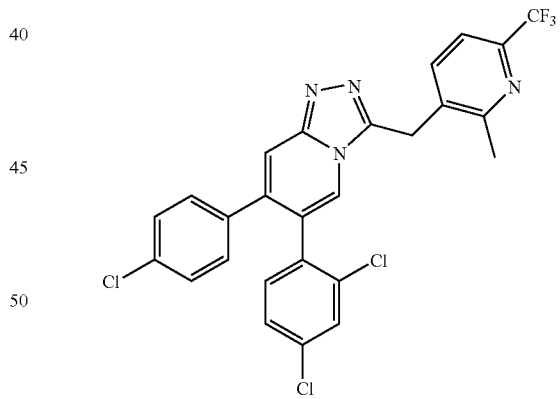

The title compound (5.5 mg, 50%) as a white powder was prepared from 6-bromo-7-(4-chlorophenyl)-3-((2-methyl-6-(trifluoromethyl)pyridin-3-yl)methyl)-[1,2,4]triazolo[4,3-a]pyridine (9.5 mg, 0.020 mmol), 2,4-dichlorophenylboronic acid (7.5 mg, 0.039 mmol, $K_2CO_3$ (8.2 mg, 0.059 mmol) and Pd(PPh$_3$)$_4$ (2.8 mg, 0.002 mmol) in 1,4-dioxane (0.28 mL) and $H_2O$ (0.09 mL) by the procedures analogous to those described for 7-(4-chlorophenyl)-6-(2,4-dichlorophenyl)-3-((6-(trifluoromethylpyridin-3-yl)methyl)-[1,2,4]triazolo[4,3-a]pyridine (Example 56E). LC/MS (method B): retention time=2.04 min, $[M+H]^+=547.2$.

Example 58

Preparation of 7-(4-chlorophenyl)-6-(2-fluorophenyl)-3-((2-ethyl-6-(trifluoromethyl)pyridin-3-yl)methyl)-[1,2,4]triazolo[4,3-a]pyridine

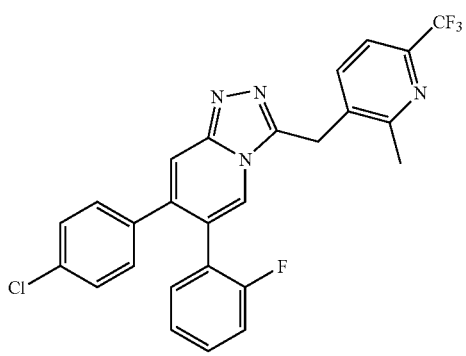

The title compound (5.5 mg, 55%) as a white powder was prepared from 6-bromo-7-(4-chlorophenyl)-3-((2-methyl-6-(trifluoromethylpyridin-3-yl)methyl)-[1,2,4]triazolo[4,3-a]pyridine (9.5 mg, 0.020 mmol), 2-fluorophenylboronic acid (5.5 mg, 0.039 mmol), $K_2CO_3$ (8.2 mg, 0.059 mmol) and $Pd(PPh_3)_4$ (2.8 mg, 0.002 mmol) in 1,4-dioxane (0.28 mL) and $H_2O$ (0.09 mL) by the procedures analogous to those described for 7-(4-chlorophenyl)-6-(2,4-dichlorophenyl)-3-((6-(trifluoromethyl)pyridin-3-yl)methyl)-[1,2,4]triazolo[4,3-a]pyridine (Example 56). LC/MS (method B): retention time=Time: 1.86, $[M+H]^+=497.3$.

Example 59

Preparation of 7-(4-chlorophenyl)-6-(2-methoxyphenyl)-3-((2-methyl-6-(trifluoromethylpyridin-3-yl)methyl)-[1,2,4]triazolo[4,3-a]pyridine

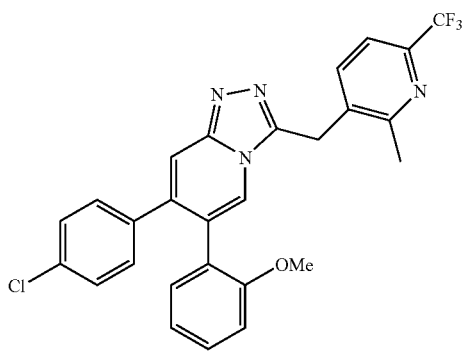

The title compound (7.7 mg, 75%) as a white powder was prepared from 6-bromo-7-(4-chlorophenyl)-3-((2-methyl-6-(trifluoromethyl)pyridin-3-yl)methyl)-[1,2,4]triazolo[4,3-a]pyridine (9.5 mg, 0.020 mmol), 2-methoxyphenylboronic acid (6.0 mg, 0.039 mmol), $K_2CO_3$ (8.2 mg, 0.059 mmol) and $Pd(PPh_3)_4$ (2.8 mg, 0.002 mmol) in 1,4-dioxane (0.28 mL) and $H_2O$ (0.09 mL) by the procedures analogous to those described for 7-(4-chlorophenyl)-6-(2,4-dichlorophenyl)-3-((6-(trifluoromethyl)pyridin-3-yl)methyl)-[1,2,4]triazolo[4,3-a]pyridine (Example 56E). LC/MS (method B): retention time=1.87 min, $[M+H]^+=509.3$.

Example 60

Preparation of 7-(4-chlorophenyl)-6-(2-chloro-4-methylphenyl)-3-((2-methyl-6-(trifluoromethyl)pyridin-3-yl)methyl)-[1,2,4]triazolo[4,3-a]pyridine

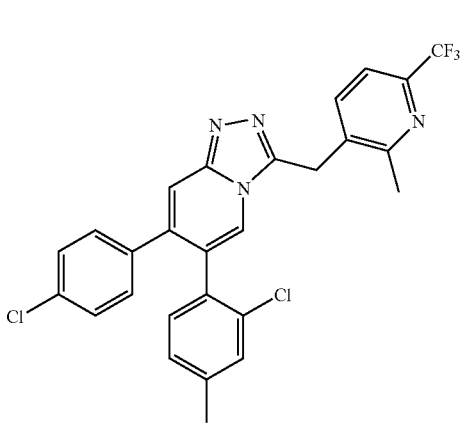

The title compound (6.5 mg, 60%) as a white powder was prepared from 6-bromo-7-(4-chlorophenyl)-3-((2-methyl-6-(trifluoromethyl)pyridin-3-yl)methyl)-[1,2,4]triazolo[4,3-a]pyridine (9.5 mg, 0.020 mmol), 2-chloro-4-methylphenylboronic acid (6.7 mg, 0.039 mmol), $K_2CO_3$ (8.2 mg, 0.059 mmol) and $Pd(PPh_3)_4$ (2.8 mg, 0.002 mmol) in 1,4-dioxane (0.28 mL) and $1H_2O$ (0.09 mL) by the procedures analogous to those described for 7-(4-chlorophenyl)-6-(2,4-dichlorophenyl)-3-((6-(trifluoromethyl)pyridin-3-yl)methyl)-[1,2,4]triazolo[4,3-a]pyridine (Example 56E). LC/MS (method B): retention time 2.01 min, $[M+H]^+=527.3$.

Example 61

Preparation of 7-(4-chlorophenyl)-3-((2-methyl-6-(trifluoromethyl)pyridin-3-yl)methyl)-6-o-tolyl-[1,2,4]triazolo[4,3-a]pyridine

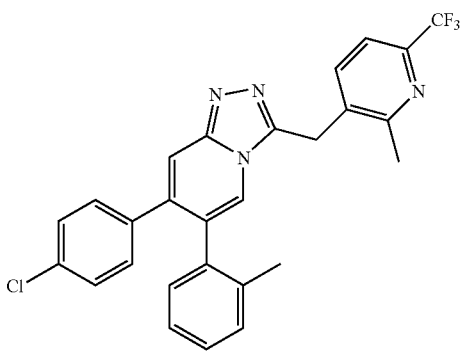

The title compound (6.3 mg, 65%) as a white powder was prepared from 6-bromo-7-(4-chlorophenyl)-3-((2-methyl-6-(trifluoromethyl)pyridin-3-yl)methyl)-[1,2,4]triazolo[4,3-a]pyridine (9.5 mg, 0.020 mmol), 2-methylphenylboronic acid (5.4 mg, 0.039 mmol), $K_2CO_3$ (8.2 mg, 0.059 mmol) and $Pd(PPh_3)_4$ (2.8 mg, 0.002 mmol) in 1,4-dioxane (0.28 mL)

and H₂O (0.09 mL) by the procedures analogous to those described for 7-(4-chlorophenyl)-6-(2,4-dichlorophenyl)-3-((6-(trifluoromethyl)pyridin-3-yl)methyl)[1,2,4]triazolo[4,3-a]pyridine (Example 56E). LC/MS (method B): retention time=1.97 min, [M+H]⁺=543.3.

Example 62

Preparation of 7-(4-chlorophenyl)-6-(2,4-dimethylphenyl)-3-((2-methyl-6-(trifluoromethyl 3 pyridin-3-yl)methyl)-[1,2,4]triazolo[4,3-a]pyridine

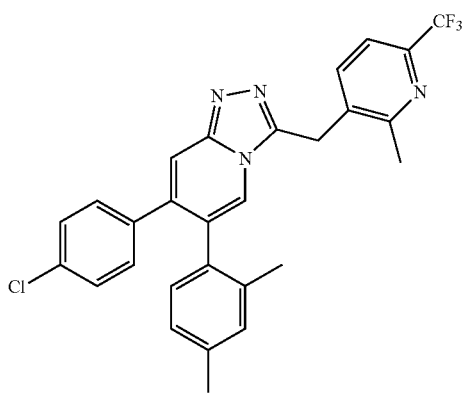

The title compound (6.5 mg, 65%) as a white powder was prepared from 6-bromo-7-(4-chlorophenyl)-3-((2-methyl-6-(trifluoromethyl)pyridin-3-yl)methyl)-[1,2,4]triazolo[4,3-a]pyridine (9.5 mg, 0.020 mmol), 2,4-dimethylphenylboronic acid (5.9 mg, 0.039 mmol), K₂CO₃ (8.2 mg, 0.059 mmol) and Pd(PPh₃)₄ (2.8 mg, 0.002 mmol) in 1,4-dioxane (0.28 mL) and H₂O (0.09 mL) by the procedures analogous to those described for 7-(4-chlorophenyl)-6-(2,4-dichlorophenyl)-3-((6-(trifluoromethyl)pyridin-3-yl)methyl)-[1,2,4]triazolo[4,3-a]pyridine (Example 56E). LC/MS (method B): retention time 2.00 min, [M+H]⁺=507.3.

Example 63

Preparation of 6-(2-chloro-4-methoxyphenyl)-7-(4-chlorophenyl)-3-((2-methyl-6-(trifluoromethylpyridin-3-yl)methyl)-[1,2,4]triazolo[4,3-a]pyridine

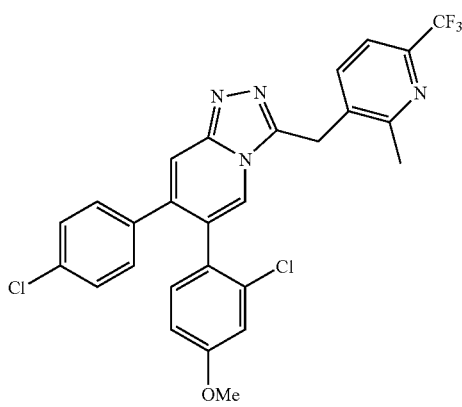

The title compound (7.5 mg, 70%) as a white powder was prepared from 6-bromo-7-(4-chlorophenyl)-3-((2-methyl-6-(trifluoromethyl)pyridin-3-yl)methyl)-[1,2,4]triazolo[4,3-a]pyridine (9.5 mg, 0.020 mmol), 2-chloro-4-methoxyphenylboronic acid (7.3 mg, 0.039 mmol), K₂CO₃ (8.2 mg, 0.059 mmol and Pd(PPh₃)₄ (2.8 mg, 0.002 mmol) in 1,4-dioxane (0.28 mL) and H₂O (0.09 mL) by the procedures analogous to those described for 7-(4-chlorophenyl)-6-(2,4-dichlorophenyl)-3-((6-(trifluoromethyl)pyridin-3-yl)methyl)-[1,2,4]triazolo[4,3-a]pyridine (Example 56E). LC/MS (method B): retention time 1.97 min [M+H]⁺=543.3.

Example 64

Preparation of 6-(2-chlorophenyl)-7-(4-chlorophenyl)-3-(2,2,2-trifluoroethoxy)-[1,2,4]triazolo[4,3-a]pyridine

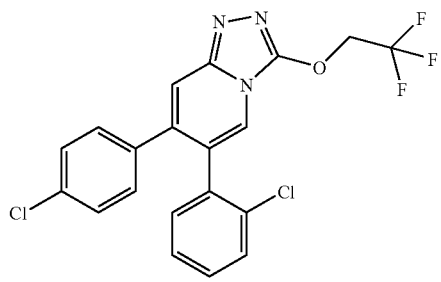

64A. Preparation of 6-(2-chlorophenyl)-7-(4-chlorophenyl)-[1,2,4]triazolo[4,3-a]pyridin-3(2H)-one

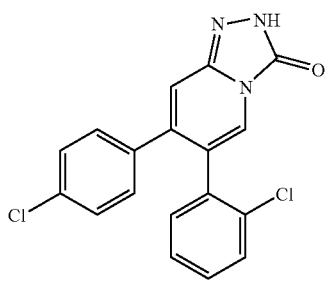

The title compound (190 mg, 88% yield) as a yellow foam was prepared from 5-(2-chlorophenyl)-4-(4-chlorophenyl)-2-hydrazinylpyridine (200 mg, 0.61 mmol) in a manner analogous to that in which 6-(2-chlorophenyl)-7-(4-chlorophenyl)-[1,2,4]triazolo[4,3-b]pyridazin-3(2H)-one (Example 1G) was prepared. HPLC/MS: retention time=3.83 min, [M+H]⁺=356.1.

64B. Preparation of 3-chloro-6-(2-chlorophenyl)-7-(4-chlorophenyl)-[1,2,4]triazolo[4,3-b]pyridine

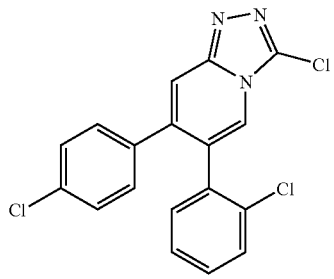

The title compound (100 mg, 56% yield) as a white solid was prepared from 6-(2-chlorophenyl)-7-(4-chlorophenyl)-[1,2,4]triazolo[4,3-a]pyridin-3(2H)-one (170 mg, 0.48 mmol) in a manner analogous to that in which 3-chloro-6-(2-chlorophenyl)-7-(4-chlorophenyl)-[1,2,4]triazolo[4,3-b]pyridazine (Example 1H) was prepared. HPLC/MS: retention time=3.87 min, [M+H]$^+$=374.0.

64C. Preparation of 6-(2-chlorophenyl)-7-(4-chlorophenyl)-3-(2,2,2-trifluoroethoxy)-[1,2,4]triazolo[4,3-a]pyridine

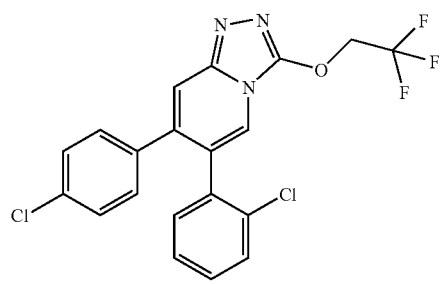

The title compound (21 mg, 48% yield) as a white powder was prepared from 3-chloro-6-(2-chlorophenyl)-7-(4-chlorophenyl)-[1,2,4]triazolo[4,3-b]pyridine (38 mg, 0.1 mmol), 2,2,2-trifluoroethanol (72 µL, 1.0 mmol), 2-tert-butylimino-2-diethylamino-1,3-dimethyl-perhydro-1,3,2-diazaphosphorine (144 µL, 0.5 mmol) and anhydrous THF (0.5 mL) in a manner analogous to that in which 6-(2-chlorophenyl)-7-(4-chlorophenyl)-3-(2,2,2-trifluoroethoxy)-[1,2,4]triazolo[4,3-a]pyridazine (Example 6) was prepared. HPLC/MS: retention time=3.86 min, [M+H]$^+$=438.1.

Biological Evaluation

Cannabinoid Receptor Binding Assay

Radioligand binding studies were conducted in membranes prepared from Chinese Hamster Ovary (CHO) cells that over-express recombinant human CB-1 (CHO-CB-1 cells). Total assay volume for the binding studies was 100 µl. 5 µg of membranes were brought up to a final volume of 95 µl with Binding Buffer (25 mM HEPES, 150 mM NaCl, 2.5 mM CaCl$_2$, 1 mM MgCl$_2$, 0.25% BSA). The diluted membranes were preincubated with a compound or DMSO vehicle. The binding reaction was initiated by the addition of 2 nM final $^3$H—CP-55,940 (120 Ci/mmol) and proceeded for 2.5 hours at room temperature. The binding reaction was terminated by transferring the reaction to GF/B 96 well plates (presoaked with 0.3% polyethylenimine) using a Packard Cell Harvester. The filter was washed with 0.25×PBS, 30 µl MicroScint was added per well, and the bound radiolabel was quantitated by scintillation counting on a Packard TopCount Scintillation Counter. The CB-2 radioligand binding assay was conducted identically except that the membranes from CHO-CB-2 cells were used.

For a compound to be considered a CB-1 antagonist, the compound must possess a CD-1 receptor binding affinity Ki less than 13000 nM. As determined by the assay described above, the CB-1 receptor binding $K_i$ values of working Examples 1-63 fall within the range of 0.01 nM to 10000 nM.

Cannabinoid Receptor Functional Activity Assay

Functional CB-1 inverse agonist activity of test compounds was determined in CHO-CB-1 cells using a cAMP accumulation assay. CHO-CB-1 cells were grown in 96 well plates to near confluence. On the day of the functional assay, growth medium was aspirated and 100 of Assay Buffer (PBS plus 25 mM HEPES/0.1 mM 3-isobutyl-1-methylxanthine/0.1% BSA) was added. Compounds were added to the Assay buffer diluted 1:100 from 100% DMSO and allowed to pre-incubate for 10 minutes prior to addition of 5 uM forskolin. The mixture was allowed to proceed for 15 minutes at room temperature and was terminated by the addition of 0.1 N HCl. The total intracellular cAMP concentration was quantitated using the Amersham cAMP SPA kit.

Utilities and Combinations

Utilities

The compounds of the present invention are cannabinoid receptor modulators, and include compounds which are, for example, selective agonists, partial agonists, inverse agonists, antagonists or partial antagonists of the cannabinoid receptor. Accordingly, the compounds of the present invention may be useful for the treatment or prevention of diseases and disorders associated with G-protein coupled cannabinoid receptor activity. Preferably, compounds of the present invention possess activity as antagonists or inverse agonists of the CB-1 receptor, and may be used in the treatment of diseases or disorders associated with the activity of the CB-1 receptor.

Accordingly, the compounds of the present invention can be administered to mammals, preferably humans, for the treatment of a variety of conditions and disorders, including, but not limited to metabolic and eating disorders as well as conditions associated with metabolic disorders, (e.g., obesity, diabetes, arteriosclerosis, hypertension, polycystic ovary disease, cardiovascular disease, osteoarthritis, dermatological disorders, hypertension, insulin resistance, hypercholesterolemia, hypertriglyceridemia, cholelithiasis and sleep disorders, hyperlipidemic conditions, bulimia nervosa and compulsive eating disorders) or psychiatric disorders, such as substance abuse, depression, anxiety, mania and schizophrenia. These compounds could also be used for the improvement of cognitive function (e.g., the treatment of dementia, including Alzheimer's disease, short term memory loss and attention deficit disorders); neurodegenerative disorders (e.g., Parkinson's Disease, cerebral apoplexy and craniocerebral trauma) and hypotension (e.g., hemorrhagic and endotoxin-induced hypotension). These compounds could also be used for treatment of catabolism in connection with pulmonary dysfunction and ventilator dependency; treatment of cardiac dysfunction (e.g., associated with valvular disease, myocardial infarction, cardiac hypertrophy or congestive heart failure); and improvement of the overall pulmonary function; transplant rejection; rheumatoid arthritis; multiple sclerosis; inflammatory bowel disease; lupus; graft vs. host disease; T-cell mediated hypersensitivity disease; psoriasis; asthma; Hashimoto's thyroiditis; Guillain-Barre syndrome; cancer; contact dermatitis; allergic rhinitis; and ischemic or reperfusion injury.

Compounds useful in the treatment of appetitive or motivational disorders regulate desires to consume sugars, carbohydrates, alcohol or drugs and more generally to regulate the consumption of ingredients with hedonic value. In the present description and in the claims, appetitive disorders are understood as meaning: disorders associated with a substance and especially abuse of a substance and/or dependency on a substance, disorders of eating behaviors, especially those liable to cause excess weight, irrespective of its origin, for example: bulimia nervosa, craving for sugars. The present invention therefore further relates to the use of a CB-1 receptor antagonist or inverse agonist for the treatment of bulimia and obesity, including obesity associated with type II diabetes (non-insulin-dependent diabetes), or more generally any disease resulting in the patient becoming overweight. Obesity, as described herein, is defined by a body mass index ($kg/m^2$) of at least 26. It may be due to any cause, whether genetic or environmental, including overeating and bulemia, polycycstic ovary disease, craniopharyngeoma, Prader-Willi Syndrome, Frohlich's Syndrome, Type II diabetes, growth hormone deficiency, Turner's Syndrome and other pathological states characterized by reduced metabolic activity or reduced energy expenditure. As used with reference to the utilities described herein, the term "treating" or "treatment" encompasses prevention, partial alleviation, or cure of the disease or disorder. Further, treatment of obesity is expected to prevent progression of medical covariants of obesity, such as arteriosclerosis, Type II diabetes, polycystic ovary disease, cardiovascular disease, osteoarthritis, dermatological disorders, hypertension, insulin resistance, hypercholesterolemia, hypertriglyceridemia, cholelithiasis and sleep disorders.

Compounds in the present invention may also be useful in treating substance abuse disorders, including substance dependence or abuse without physiological dependence. Substances of abuse include alcohol, amphetamines (or amphetamine-like substances), caffeine, cannabis, cocaine, hallucinogens, inhalants, nicotine, opioids, phencyclidine (or phencyclidine-like compounds), sedative-hypnotics or benzodiazepines, and other (or unknown) substances and combinations of the above. The terms "substance abuse disorders" also includes drug or alcohol withdrawal syndromes and substance-induced anxiety or mood disorder with onset during withdrawal.

Compounds in the present invention may be useful in treating memory impairment and cognitive disorders. The condition of memory impairment is manifested by impairment of the ability to learn new information and/or the inability to recall previously learned information. Memory impairment is a primary symptom of dementia and can also be a symptom associated with such diseases as Alzheimer's disease, schizophrenia, Parkinson's disease, Huntington's disease, Pick's disease, Creutzfeld-Jakob disease, HIV, cardiovascular disease, and head trauma as well as age-related cognitive decline. Dementias are diseases that include memory loss and additional intellectual impairment separate from memory. Cannabinoid receptor modulators may also be useful in treating cognitive impairments related to attentional deficits, such as attention deficit disorder.

Compounds in the present invention may also be useful in treating diseases associated with dysfunction of brain dopaminergic systems, such as Parkinson's Disease and substance abuse disorders. Parkinsons's Disease is a neurogenerative movement disorder characterized by bradykinesia and tremor.

As modulators of the cannabinoid receptor, the compounds of the present invention are further useful for the treatment and prevention of respiratory diseases and disorders. Respiratory diseases for which cannabinoid receptor modulators are useful include, but are not limited to, chronic pulmonary obstructive disorder, emphysema, asthma, and bronchitis. In addition, cannabinoid receptor modulators block the activation of lung epithelial cells by moieties such as allergic agents, inflammatory cytokines or smoke, thereby limiting release of mucin, cytokines, and chemokines, or selectively inhibiting lung epithelial cell activation.

Moreover, the compounds employed in the present invention may stimulate inhibitory pathways in cells, particularly in leukocytes, lung epithelial cells, or both, and are thus useful in treating such diseases. "Leukocyte activation" is defined herein as any or all of cell proliferation, cytokine production, adhesion protein expression, and production of inflammatory mediators. "Epithelial cell activation" is defined herein as the production of any or all of mucins, cytokines, chemokines, and adhesion protein expression.

Use of the compounds of the present invention for treating leukocyte activation-associated disorders is exemplified by, but is not limited to, treating a range of disorders such as: transplant (such as organ transplant, acute transplant, xenotransplant or heterograft or homograft (such as is employed in burn treatment)) rejection; protection from ischemic or reperfusion injury such as ischemic or reperfusion injury incurred during organ transplantation, myocardial infarction, stroke or other causes; transplantation tolerance induction; arthritis (such as rheumatoid arthritis, psoriatic arthritis or osteoarthritis); multiple sclerosis; respiratory and pulmonary diseases including but not limited to chronic obstructive pulmonary disease (COPD), emphysema, bronchitis, and acute respiratory distress syndrome (ARDS); inflammatory bowel disease, including ulcerative colitis and Crohn's disease; lupus (systemic lupus erythematosis); graft vs. host disease; T-cell mediated hypersensitivity diseases, including contact hypersensitivity, delayed-type hypersensitivity, and gluten-sensitive enteropathy (Celiac disease); psoriasis; contact dermatitis (including that due to poison ivy); Hashimoto's thyroiditis; Sjogren's syndrome; Autoimmune Hyperthyroidism, such as Graves' Disease; Addison's disease (autoimmune disease of the adrenal glands); Autoimmune polyglandular disease (also known as autoimmune polyglandular syndrome); autoimmune alopecia; pernicious anemia; vitiligo; autoimmune hypopituatarism; Guillain-Barre syndrome; other autoimmune diseases; glomerulonephritis; serum sickness; uticaria; allergic diseases such as respiratory allergies (asthma, hayfever, allergic rhinitis) or skin allergies; scleracierma; mycosis fungoides; acute inflammatory and respiratory responses (such as acute respiratory distress syndrome and ishchemia/reperfusion injury); dermatomyositis; alopecia areata; chronic actinic dermatitis; eczema; Behcet's disease; Pustulosis palmoplanteris; Pyoderma gangrenum; Sezary's syndrome; atopic dermatitis; systemic schlerosis; and morphea. The term "leukocyte activation-associated" or "leukocyte-activation mediated" disease as used herein includes each of the above referenced diseases or disorders. In a particular embodiment, the compounds of the present invention are useful for treating the aforementioned exemplary disorders irrespective of their etiology. The combined activity of the present compounds towards monocytes, macrophages, T-cells, etc. may be useful in treating any of the above-mentioned disorders.

Cannabinoid receptors are important in the regulation of Fc gamma receptor responses of monocytes and macrophages. Compounds of the present invention inhibit the Fc gamma dependent production of TNF alpha in human monocytes/macrophages. The ability to inhibit Fc gamma receptor dependent monocyte and macrophage responses results in additional anti-inflammatory activity for the present compounds. This activity is especially of value, for example, in treating inflammatory diseases such as arthritis or inflammatory bowel disease. In particular, the present compounds are useful for treating autoimmune glomerulonephritis and other instances of glomerulonephritis induced by deposition of immune complexes in the kidney that trigger Fc gamma receptor responses leading to kidney damage.

Cannabinoid receptors are expressed on lung epithelial cells. These cells are responsible for the secretion of mucins and inflammatory cytokines/chemokines in the lung and are thus intricately involved in the generation and progression of respiratory diseases. Cannabinoid receptor modulators regulate both the spontaneous and the stimulated production of both mucins and cytokines. Thus, such compounds are useful in treating respiratory and pulmonary diseases including, COPD, ARDS, and bronchitis.

Further, cannabinoid receptors may be expressed on gut epithelial cells and hence regulate cytokine and mucin production and may be of clinical use in treating inflammatory diseases related to the gut. Cannabinoid receptors are also expressed on lymphocytes, a subset of leukocytes. Thus, cannabinoid receptor modulators will inhibit B and T-cell activation, proliferation and differentiation. Thus, such compounds will be useful in treating autoimmune diseases that involve either antibody or cell mediated responses such as multiple sclerosis and lupus.

In addition, cannabinoid receptors regulate the Fc epsilon receptor and chemokine induced degranulation of mast cells and basophils. These play important roles in asthma, allergic rhinitis, and other allergic disease. Fc epsilon receptors are stimulated by IgE-antigen complexes. Compounds of the present invention inhibit the Fc epsilon induced degranulation responses, including the basophil cell line, RBL. The ability to inhibit Fc epsilon receptor dependent mast cell and basophil responses results in additional anti-inflammatory and anti-allergic activity for the present compounds. In particular, the present compounds are useful for treating asthma, allergic rhinitis, and other instances of allergic disease.

Combinations

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other suitable therapeutic agents useful in the treatment of the aforementioned disorders including: anti-obesity agents; anti-diabetic agents, appetite suppressants; cholesterol/lipid-lowering agents, HDL-raising agents, cognition enhancing agents, agents used to treat neurodegeneration, agents used to treat respiratory conditions, agents used to treat bowel disorders, anti-inflammatory agents; anti-anxiety agents; anti-depressants; anti-hypertensive agents; cardiac glycosides; and anti-tumor agents.

Such other therapeutic agent(s) may be administered prior to, simultaneously with, or following the administration of the cannabinoid receptor modulators in accordance with the invention.

Examples of suitable anti-obesity agents for use in combination with the compounds of the present invention include melanocortin receptor (MC4R) agonists, melanin-concentrating hormone receptor (MCHR) antagonists, growth hormone secretagogue receptor (GHSR) antagonists, galanin receptor modulators, orexin antagonists, CCK agonists, GLP-1 agonists, and other Pre-proglucagon-derived peptides; NPY1 or NPY5 antagonist, NPY2 and NPY4 modulators, corticotropin releasing factor agonists, histamine receptor-3 (H3) modulators, aP2 inhibitors, PPAR gamma modulators, PPAR delta modulators, acetyl-CoA carboxylase (ACC) inhibitors, 11-β-HSD-1 inhibitors, adinopectin receptor modulators; beta 3 adrenergic agonists, such as AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, a thyroid receptor beta modulator, such as a thyroid receptor ligand as disclosed in WO 97/21993 (U. Cal SF), WO 99/00353 (KaroBio) and WO 00/039077 (KaroBio), a lipase inhibitor, such as orlistat or ATL-962 (Alizyme), serotonin receptor agonists, (e.g., BVT-933 (Biovitrum)), monoamine reuptake inhibitors or releasing agents, such as fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine or mazindol, anorectic agents such as topiramate (Johnson & Johnson), CNTF (ciliary neurotrophic factor)/Axokine® (Regeneron), BDNF (brain-derived neurotrophic factor), leptin and leptin receptor modulators, or cannabinoid-1 receptor antagonists, such as SR-141716 (Sanofi) or SLV-319 (Solvay).

Examples of suitable anti-diabetic agents for use in combination with the compounds of the present invention include: insulin secretagogues or insulin sensitizers, which may include biguanides, sulfonyl ureas, glucosidase inhibitors, aldose reductase inhibitors, PPAR γ agonists such as thiazolidinediones, PPAR α agonists (such as fibric acid derivatives), PPAR δ antagonists or agonists, PPAR α/γ dual agonists, 11-β-HSD-1 inhibitors, dipeptidyl peptidase IV (DP4) inhibitors, SGLT2 inhibitors, glycogen phosphorylase inhibitors, and/or meglitinides, as well as insulin, and/or glucagon-like peptide-1 (GLP-1), GLP-1 agonist, and/or a PTP-1B inhibitor (protein tyrosine phosphatase-1B inhibitor).

The antidiabetic agent may be an oral antihyperglycemic agent preferably a biguanide such as metformin or phenformin or salts thereof, preferably metformin HCl. Where the antidiabetic agent is a biguanide, the compounds of the present invention will be employed in a weight ratio to biguanide within the range from about 0.001:1 to about 10:1, preferably from about 0.01:1 to about 5:1.

The antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the beta-cells, with glyburide and glipizide being preferred, which may be administered in the same or in separate oral dosage forms. The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of the present invention may be employed in combination with a PPAR γ agonist such as a thiazolidinedione oral anti-diabetic agent or other insulin sensitizers (which has an insulin sensitivity effect in NIDDM patients) such as rosiglitazone (SKB), pioglitazone (Takeda), Mitsubishi's MCC-555 (disclosed in U.S. Pat. No. 5,594,016), Glaxo-Wellcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), N,N-2344 (Dr. Reddy/NN), or YM-440 (Yamanouchi), preferably rosiglitazone and pioglitazone.

The compounds of the present invention may be employed with a PPARα/γ dual agonist such as MK-767/KRP-297 (Merck/Kyorin; as described in, K. Yajima, et. al., *Am. J. Physiol Endocrinol. Metab.*, 284: E1966-E971 (2003)), AZ-242 (tesaglitazar; Astra-Zeneca; as described in B. Ljung, et. al., *J Lipid Res.*, 43, 1855-1863 (2002)); muraglitazar; or the compounds described in U.S. Pat. No. 6,414,002.

The compounds of the present invention may be employed in combination with anti-hyperlipidemia agents, or agents used to treat arteriosclerosis. An example of an hypolipidemic agent would be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, pitavastatin (Nissan/Sankyo's nisvastatin (NK-104) or itavastatin), disclosed in U.S. Pat. No. 5,011,930, Shionogi-Astra/Zeneca rosuvastatin (visastatin (ZD-4522)) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0,142,146 A2, and quinoline and pyridine derivatives disclosed in U.S. Pat. Nos. 5,506,219 and 5,691,322. In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller, et al., *J. Med. Chem.*, 31, 1869-1871 (1998) including isoprenoid (phosphinyl-methyl)phosphonates as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., *Current Pharmaceutical Design*, 2, 1-40 (1996).

In addition, other squalene synthetase inhibitors suitable for use herein include the terpenoid pyrophosphates disclosed by P. Ortiz de Montellano, et al., *J. Med. Chem.*, 20, 243-249 (1977), the farnesyl diphosphate analog A and presqualene pyrophosphate (PSQ-PP) analogs as disclosed by Corey and Volante, *J. Am. Chem. Soc.*, 98, 1291-1293 (1976), phosphinylphosphonates reported by McClard, R. W. et al., *J. Am. Chem. Soc.*, 109, 5544 (1987) and cyclopropanes reported by Capson, T. L., PhD dissertation, June, 1987, Dept. Med. Chem. U of Utah, Abstract, Table of Contents, pp 16, 17, 40-43, 48-51, Summary.

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (SECHOLEX, POLICEXIDE) and cholestagel (Sankyo/Geltex), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinornoto AJ-814 (azulene derivative), melinamide (Sumitomo), Sandoz 58-035, American Cyanamid CL-277,082 and CL-283,546 (disubstituted urea derivatives), nicotinic acid (niacin), acipimox, acifran, neomycin, p-aminosalicylic acid, aspirin, poly(diallylmethylamine) derivatives such as disclosed in U.S. Pat. No. 4,759,923, quaternary amine poly (diallyldimethylammonium chloride) and ionenes such as disclosed in U.S. Pat. No. 4,027,009, and other known serum cholesterol lowering agents.

The other hypolipidemic agent may be an ACAT inhibitor (which also has anti-atherosclerosis activity) such as disclosed in, *Drugs of the Future*, 24, 9-15 (1999), (Avasimibe); "The ACAT inhibitor, C1-1011 is effective in the prevention and regression of aortic fatty streak area in hamsters", Nicolosi et al., *Atherosclerosis (Shannon, Irel)*, 137 (1), 77-85 (1998); "The pharmacological profile of FCE 27677: a novel ACAT inhibitor with potent hypolipidemic activity mediated by selective suppression of the hepatic secretion of ApoB100-containing lipoprotein", Ghiselli, Giancarlo, *Cardiovasc. Drug Rev.*, 16 (1), 16-30 (1998); "RP 73163: a bioavailable alkylsulfinyl-diphenylimidazole ACAT inhibitor", Smith, C., et al., *Bioorg. Med. Chem. Lett.*, 6 (1), 47-50 (1996); "ACAT inhibitors: physiologic mechanisms for hypolipidemic and anti-atherosclerotic activities in experimental animals", Krause et al., Editor(s): Ruffolo, Robert R., Jr.; Hollinger, Mannfred A., *Inflammation: Mediators Pathways*, 173-98 (1995), Publisher: CRC, Boca Raton, Fla.; "ACAT inhibitors: potential anti-atherosclerotic agents", Sliskovic et al., *Curr. Med. Chem.*, 1 (3), 204-25 (1994); "Inhibitors of acyl-CoA: cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)-methyl]ureas with enhanced hypocholesterolemic activity", Stout et al., *Chemtracts: Org. Chem.*, 8 (6), 359-62 (1995), or TS-962 (Taisho Pharmaceutical Co. Ltd), as well as F-1394, CS-505, F-12511, HL-004, K-10085 and YIC-C8-434.

The hypolipidemic agent may be an upregulator of LDL receptor activity such as MD-700 (Taisho Pharmaceutical Co. Ltd) and LY295427 (Eli Lilly). The hypolipidemic agent may be a cholesterol absorption inhibitor preferably Schering-Plough's SCH48461 (ezetimibe) as well as those disclosed in *Atherosclerosis* 115, 45-63 (1995) and *J. Med. Chem.* 41, 973 (1998).

The other lipid agent or lipid-modulating agent may be a cholesteryl transfer protein inhibitor (CETP) such as Pfizer's CP-529,414 as well as those disclosed in WO/0038722 and in EP 818448 (Bayer) and EP 992496, and Pharmacia's SC-744 and SC-795, as well as CETi-1 and JTT-705.

The hypolipidemic agent may be an ileal $Na^+$/bile acid cotransporter inhibitor such as disclosed in Drugs of the Future, 24, 425-430 (1999). The ATP citrate lyase inhibitor which may be employed in the combination of the invention may include, for example, those disclosed in U.S. Pat. No. 5,447,954.

The other lipid agent also includes a phytoestrogen compound such as disclosed in WO 00/30665 including isolated soy bean protein, soy protein concentrate or soy flour as well as an isoflavone such as genistein, daidzein, glycitein or equol, or phytosterols, phytostanol or tocotrienol as disclosed in WO 2000/015201; a beta-lactam cholesterol absorption inhibitor such as disclosed in EP 675714; an HDL upregulator such as an LXR agonist, a PPAR α-agonist and/or an FXR agonist; an LDL catabolism promoter such as disclosed in EP 1022272; a sodium-proton exchange inhibitor such as disclosed in DE 19622222; an LDL-receptor inducer or a steroidal glycoside such as disclosed in U.S. Pat. No. 5,698,527 and GB 2304106; an anti-oxidant such as beta-carotene, ascorbic acid, α-tocopherol or retinol as disclosed in WO 94/15592 as well as Vitamin C and an antihomocysteine agent such as folic acid, a folate, Vitamin B 6, Vitamin B12 and Vitamin E; isoniazid as disclosed in WO 97/35576; a cholesterol absorption inhibitor, an HMG-CoA synthase inhibitor, or a lanosterol demethylase inhibitor as disclosed in WO 97/48701; a PPAR δ agonist for treating dyslipidemia; or a sterol regulating element binding protein-I (SREBP-1) as disclosed in WO 2000/050574, for example, a sphingolipid, such as ceramide, or neutral sphingomyelenase (N-SMase) or fragment thereof. Preferred hypolipidemic agents are pravastatin, lovastatin, simvastatin, atorvastatin, fluvastatin, pitavastatin and rosuvastatin, as well as niacin and/or cholestagel.

The compounds of the present invention may be employed in combination with anti-hypertensive agents. Examples of suitable anti-hypertensive agents for use in combination with the compounds of the present invention include beta adrenergic blockers, calcium channel blockers (L-type and/or T-type; e.g. diltiazem, verapamil, nifedipine, amlodipine and mybefiadil), diuretics (e.g., ehlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetamide, triamtrenene, amiloride, spironolactone), renin inhibitors, ACE inhibitors (e.g., captopril, zofenopril, fosinopril enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043, 265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Cannabinoid receptor modulators could be useful in treating other diseases associated with obesity, including sleep disorders. Therefore, the compounds described in the present invention could be used in combination with therapeutics for treating sleep disorders. Examples of suitable therapies for treatment of sleeping disorders for use in combination with the compounds of the present invention include melatonin analogs, melatonin receptor antagonists, ML 1 B agonists, GABA receptor modulators; NMDA receptor modulators, histamine-3 (H3) receptor modulators, dopamine agonists and orexin receptor modulators.

Cannabinoid receptor modulators may reduce or ameliorate substance abuse or addictive disorders. Therefore, combination of cannabinoid receptor modulators with agents used to treat addictive disorders may reduce the dose requirement or improve the efficacy of current addictive disorder therapeutics. Examples of agents used to treat substance abuse or addictive disorders are: selective serotonin reuptake inhibitors (SSRI), methadone, buprenorphine, nicotine and bupropion.

Cannabinoid receptor modulators may reduce anxiety or depression; therefore, the compounds described in this application may be used in combination with anti-anxiety agents or antidepressants. Examples of suitable anti-anxiety agents for use in combination with the compounds of the present invention include benzodiazepines (e.g., diazepam, lorazepam, oxazepam, alprazolam, chlordiazepoxide, clonazepam, chlorazepate, halazepam and prazepam), 5HT1A receptor agonists (e.g., buspirone, flesinoxan, gepirone and ipsapirone), and corticotropin releasing factor (CRF) antagonists.

Examples of suitable classes of anti-depressants for use in combination with the compounds of the present invention include norepinephrine reuptake inhibitors (tertiary and secondary amine tricyclics), selective serotonin reuptake inhibitors (SSRIs) (fluoxetine, fluvoxamine, paroxetine and sertraline), monoamine oxidase inhibitors (MAOIs) (isocarboxazid, phenelzine, tranylcypromine, selegiline), reversible inhibitors of monoamine oxidase (RIMAs) (moclobemide), serotonin and norepinephrine reuptake inhibitors (SNRIs) (venlafaxine), corticotropin releasing factor (CRF) receptor antagonists, alpha-adrenoreceptor antagonists, and atypical antidepressants (bupropion, lithium, nefazodone, trazodone and viloxazine).

The combination of a conventional antipsychotic drug with a CB-1 receptor antagonist could also enhance symptom reduction in the treatment of psychosis or mania. Further, such a combination could enable rapid symptom reduction, reducing the need for chronic treatment with antipsychotic agents. Such a combination could also reduce the effective antipsychotic dose requirement, resulting in reduced probability of developing the motor dysfunction typical of chronic antipsychotic treatment.

Examples of suitable antipsychotic agents for use in combination with the compounds of the present invention include the phenothiazine (chlorpromazine, mesoridazine, thioridazine, acetophenazine, fluphenazine, perphenazine and trifluoperazine), thioxanthine (chlorprothixene, thiothixene), heterocyclic dibenzazepine (clozapine, olanzapine and aripiprazole), butyrophenone (haloperidol), diphenylbutylpiperidine (pimozide) and indolone (molindolone) classes of antipsychotic agents. Other antipsychotic agents with potential therapeutic value in combination with the compounds in the present invention include loxapine, sulpiride and risperidone.

Combination of the compounds in the present invention with conventional antipsychotic drugs could also provide an enhanced therapeutic effect for the treatment of schizophrenic disorders, as described above for manic disorders. As used here, schizophrenic disorders include paranoid, disorganized, catatonic, undifferentiated and residual schizophrenia, schizophreniform disorder, shcizoaffective disorder, delusional disorder, brief psychotic disorder and psychotic disorder not specified. Examples of suitable anitipsychotic drugs for combination with the compounds in the present invention include the antipsychotics mentioned above, as well as dopamine receptor antagonists, muscarinic receptor agonists, 5HT2A receptor antagonists and 5HT2A/dopamine receptor antagonists or partial agonists (e.g., olanzapine, aripiprazole, risperidone, ziprasidone).

The compounds described in the present invention could be used to enhance the effects of cognition-enhancing agents, such as acetylcholinesterase inhibitors (e.g., tacrine), muscarinic receptor-1 agonists (e.g., milameline), nicotinic agonists, glutamic acid receptor (AMPA and NMDA) modulators, and nootropic agents (e.g., piracetam, levetiracetam). Examples of suitable therapies for treatment of Alzheimer's disease and cognitive disorders for use in combination with the compounds of the present invention include donepezil, tacrine, revastigraine, 5HT6, gamma secretase inhibitors, beta secretase inhibitors, SK channel blockers, Maxi-K blockers, and KCNQs blockers.

The compounds described in the present invention could be used to enhance the effects of agents used in the treatment of Parkinson's Disease. Examples of agents used to treat Parkinson's Disease include: levadopa with or without a COMT inhibitor, antiglutamatergic drugs (amantadine, riluzole), alpha-2 adrenergic antagonists such as idazoxan, opiate antagonists, such as naltrexone, other dopamine agonists or transporter modulators, such as ropinirole, or pramipexole or neurotrophic factors such as glial derived neurotrophic factor (GDNF).

The compounds described in the present invention could be used in combination with suitable anti-inflammatory agents. Examples of suitable anti-inflammatory agents for use in combination with the compounds of the present invention include prednisone, dexamethasone, cyclooxygenase inhibitors (i.e., COX-1 and/or COX-2 inhibitors such as NSAIDs, aspirin, indomethacin, ibuprofen, piroxicam, Naproxen®, Celebrex®, Vioxx®), CTLA4-Ig agonists/antagonists, CD40 ligand antagonists, IMPDH inhibitors, such as mycophenolate (CellCept®), integrin antagonists, alpha-4 beta-7 integrin antagonists, cell adhesion inhibitors, interferon gamma antagonists, ICAM-1, tumor necrosis factor (TNF) antagonists (e.g., intfliximab, OR1384, including TNF-alpha inhibitors, such as tenidap, anti-TNF antibodies or soluble TNF receptor such as etanercept (Enbrel®), rapamycin (sirolimus or Rapamune) and leflunomide (Arava)), prostaglandin synthesis inhibitors, budesonide, clofazimine, CNI-1493, CD4 antagonists (e.g., priliximab), p38 mitogen-activated protein kinase inhibitors, protein tyrosine kinase (PTK) inhibitors, IKK inhibitors, and therapies for the treatment of irritable bowel syndrome (e.g., Zelnorm® and Maxi-K® openers such as those disclosed in U.S. Pat. No. 6,184,231 B1).

Exemplary of such other therapeutic agents which may be used in combination with cannabinoid receptor modulators include the following: cyclosporins (e.g., cyclosporin A), anti-IL-2 receptor (Anti-Tac), anti-CD45RB, anti-CD2, anti-CD3 (OKT-3), anti-CD4, anti-CD80, anti-C86, monoclonal antibody OKT3, agents blocking the interaction between CD40 and gp39, such as antibodies specific for CD40 and/or gp39 (i.e., CD154), fusion proteins constructed from CD40 and gp39 (CD40Ig and CD8gp39), inhibitors, such as nuclear translocation inhibitors, of NF-kappa B function, such as deoxyspergualin (DSG), gold compounds, antiproliferative agents such as methotrexate, FK506 (tacrolimus, Prograf), mycophenolate mofetil, cytotoxic drugs such as azathiprine and cyclophosphamide, anticytokines such as antiIL-4 or IL-4 receptor fusion proteins and PDE 4 inhibitors such as Ariflo, and the PTK inhibitors disclosed in the following U.S. patent applications, incorporated herein by reference in their entirety: Ser. No. 09/097,338, filed Jun. 15, 1998; Ser. No. 09/094,797, filed Jun. 15, 1998; Ser. No. 09/173,413, filed Oct. 15, 1998; and Ser. No. 09/262,525, filed Mar. 4, 1999. See also the following documents and references cited therein and incorporated herein by reference: Hollenbaugh, D., et al., "Cleavable CD40Ig Fusion Proteins and the Binding to Sgp39", *J. Immunol. Methods* (Netherlands), 188 (1), pp. 1-7 (Dec. 15, 1995); Hollenbaugh, D., et al., "The Human T Cell Antigen Gp39, A Member of the TNF Gene Family, Is a Ligand for the CD40 Receptor: Expression of a Soluble Form of Gp39 with B Cell Co-Stimulatory Activity", *EMBO J* (England), 11 (12), pp. 4313-4321 (December 1992); and Moreland, L. W. et al., "Treatment of Rheumatoid Arthritis with a Recombinant Human Tumor Necrosis Factor Receptor (P75)-Fc Fusion Protein," *New England J. of Medicine*, 337 (3), pp. 141-147 (1997).

The above other therapeutic agents, when employed in combination with the compounds of the present invention, may be used, for example, in those amounts indicated in the Physicians' Desk Reference (PDR) or as otherwise determined by one of ordinary skill in the art.

The compounds of formula (I) of the invention can be administered orally or parenterally, such as subcutaneously or intravenously, as well as by nasal application, rectally or sublingually to various mammalian species known to be subject to such maladies, e.g., humans, in an effective amount up to 1 gram, preferably up to 200 mg, more preferably up to 100 mg in a regimen of single, two or four divided daily doses.

The compounds of the formula (I) can be administered for any of the uses described herein by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The compounds of formula I can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use.

Exemplary compositions for nasal aerosol or inhalation administration include solutions in saline which can contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for rectal administration include suppositories which can contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

It will be understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition.

It should be understood that while this invention has been described herein in terms of specific embodiments set forth in detail, such embodiments are presented by way of illustration of the general principles of the invention, and the invention is not necessarily limited thereto. Certain modifications and variations in any given material, process step or chemical formula will be readily apparent to those skilled in the art without departing from the true spirit and scope of the present invention, and all such modifications and variations should be considered within the scope of the claims that follow.

What is claimed is:

1. A compound or a pharmaceutically acceptable salt or a stereoisomer thereof according to Formula I

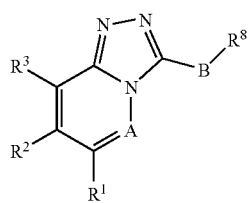

I wherein:
A is $CR^{3a}$;
B is selected from the group consisting of a direct bond, oxygen, sulfur, $NR^6$, $C(O)$, $C(O)O$, $OC(O)$, $OC(O)O$, $C(O)NR^6$, $NR^6C(O)$, $NR^6C(O)O$, $S(O)$, $S(O)_2$, $S(O)NR^6$, $S(O)_2NR^6$, $NR^6S(O)$, $NR^6S(O)_2$, and $NR^6C(O)NR^7$;

$R^1$ and $R^2$ are independently selected from the group consisting of aryl substituted with 1 to 5 $R^4$ and heteroaryl optionally substituted with 1 to 4 $R^4$;

when both $R^1$ and $R^2$ are heteroaryl, then either $R^1$ or $R^2$ is substituted with at least one $R^4$;

$R^3$ and $R^{3a}$ are independently selected from the group consisting of hydrogen, halogen, $CF_3$, $OCHF_2$, $OCF_3$, CN, $NO_2$, $OCH_3$, $SCH_3$, $OR^5$, $SR^5$, $NR^5R^6$, $C(O)H$, $C(O)R^5$, $C(O)NR^5R^6$, $NR^6C(O)R^5$, $C(O)OR^5$, $OC(O)R^5$, $OC(O)OR^5$, $S(O)R^5$, $S(O)_2R^5$, $S(O)NR^5R^6$, $S(O)_2NR^5R^6$, $NR^6S(O)R^5$, $NR^6S(O)_2R^5$, $NR^6C(O)R^5$, $NR^6C(O)OR^5$, $NR^6S(O)_2R^5$, $NR^6C(O)NR^7R^5$, alkyl, alkenyl, alkynyl, cycloalkyl and heterocyclyl, any of which may be optionally substituted with 1 to 6 $R^9$;

$R^4$, at each occurrence, is independently selected from the group consisting of halogen, OH, $CF_3$, $OCHF_2$, $OCF_3$, CN, $NO_2$, $OCH_3$, $SCH_3$, $OR^5$, $SR^5$, $NR^5R^6$, $C(O)H$, $C(O)R^5$, $C(O)NR^5R^6$, $NR^6C(O)R^5$, $C(O)OR^5$, $OC(O)R^5$, $OC(O)OR^5$, $S(O)R^5$, $S(O)_2R^5$, $S(O)NR^5R^6$, $S(O)_2NR^5R^6$, $NR^6S(O)R^5$, $NR^6S(O)_2R^5$, $NR^6C(O)R^5$, $NR^6C(O)OR^5$, $NR^6S(O)_2R^5$, $NR^6C(O)NR^5R^7$, alkyl, alkenyl, alkynyl, cycloalkyl, heterocyclyl, aryl and heteroaryl, any of which may be optionally substituted with 1 to 6 $R^9$;

$R^5$ is selected from the group consisting of $C_{1-4}$ alkyl optionally substituted with 1 to 3 $R^9$, $C_{2-4}$ alkenyl optionally substituted with 1 to 2 $R^9$, $C_{2-4}$ alkynyl optionally substituted with 1 to 2 $R^9$, $C_{3-10}$ cycloalkyl optionally substituted with 1 to 6 $R^{10}$, $C_{3-10}$ heterocyclyl optionally substituted with 1 to 6 $R^{10}$, aryl optionally substituted with 1 to 5 $R^{11}$ and heteroaryl optionally substituted with 1 to 3 $R^{10}$;

$R^6$ and $R^7$ are independently is selected from the group consisting of hydrogen, $C_{1-4}$ alkyl optionally substituted with 1 to 3 $R^9$, $C_{2-4}$ alkenyl optionally substituted with 1 to 2 $R^9$, $C_{2-4}$ alkynyl optionally substituted with 1 to 2 $R^9$, $C_{3-6}$ cycloalkyl optionally substituted with 1 to 3 $R^{10}$, and $C_{3-6}$ heterocyclyl optionally substituted with 1 to 3 $R^{10}$;

alternatively, $R^5$ and $R^6$ join to form a 3 to 7-membered ring optionally substituted with oxygen or $NR^{12}$;

alternatively, $R^5$ and $R^6$ when attached to N may be combined to form a 5 to 10-membered bicyclic heterocyclic ring system containing from 1 to 3 heteroatoms selected from the group consisting of nitrogen, oxygen, and sulfur, wherein said bicyclic heterocyclic ring system is unsaturated or partially saturated, wherein said bicyclic heterocyclic ring system is optionally substituted with 1 to 3 $R^{13}$;

alternatively, $R^6$ and $R^7$ join to form a 5 to 7-membered ring optionally substituted with oxygen or $NR^{12}$;

alternatively, $R^6$ and $R^7$ when attached to N may be combined to form a 9- or 10-membered bicyclic heterocyclic ring system containing from 1 to 3 heteroatoms selected from the group consisting of nitrogen, oxygen, and sulfur, wherein said bicyclic heterocyclic ring system is unsaturated or partially saturated, wherein said bicyclic heterocyclic ring system is optionally substituted with 1 to 3 $R^{13}$;

$R^8$ is selected from the group consisting of alkyl optionally substituted with 1 to 6 $R^9$, alkenyl optionally substituted with 1 to 6 $R^9$, alkynyl optionally substituted with 1 to 6 $R^9$, cycloalkyl optionally substituted with 1 to 6 $R^{10}$, heterocyclyl optionally substituted with 1 to 6 $R^{10}$, aryl optionally substituted with 1 to 5 $R^4$, heteroaryl optionally substituted with 1 to 3 $R^4$;

$R^9$, at each occurrence, is independently selected from the group consisting of halogen, OH, $CF_3$, $OCHF_2$, $OCF_3$, CN, $NO_2$, $OCH_3$, $SCH_3$, $OR^{12}$, $SR^{12}$, $NR^{12}R^{12a}$, C(O)H, $C(O)R^{12}$, $C(O)NR^{12}R^{12a}$, $NR^{12}C(O)R^{12a}$, $C(O)OR^{12}$, $OC(O)R^{12}$, $OC(O)OR^{12}$, $S(O)R^{12}$, $S(O)_2R^{12}$, $S(O)NR^{12}R^{12a}$, $S(O)_2NR^{12}R^{12a}$, $NR^{12}S(O)R^{12a}$, $NR^{12}S(O)_2R^{12a}$, $NR^{12}C(O)R^{12a}$, $NR^{12}C(O)OR^{12a}$, $NR^{12}S(O)_2R^{12a}$, $C_{1-3}$ haloalkyl, $C_{1-4}$ alkoxy, $C_{3-6}$ cycloalkyl optionally substituted with 1 to 3 $R^{10}$, $C_{3-10}$ heterocyclyl optionally substituted with 1 to 3 $R^{10}$, aryl optionally substituted with 1 to 5 $R^{11}$ and heteroaryl optionally substituted with 1 to 3 $R^{10}$;

$R^{10}$, at each occurrence, is independently selected from the group consisting of =O, halogen, OH, $CF_3$, $OCHF_2$, $OCF_3$, CN, $NO_2$, $OCH_3$, $SCH_3$, $OR^{12}$, $SR^{12}$, $NR^{12}R^{12a}$, C(O)H, $C(O)R^{12}$, $C(O)NR^{12}R^{12a}$, $NR^{12}C(O)R^{12a}$, $C(O)OR^{12}$, $OC(O)R^{12}$, $OC(O)OR^{12}$, $S(O)R^{12}$, $S(O)_2R^{12}$, $S(O)NR^{12}R^{12a}$, $S(O)_2NR^{12}R^{12a}$, $NR^{12}S(O)R^{12a}$, $NR^{12}S(O)_2R^{12a}$, $NR^{12}C(O)R^{12a}$, $NR^{12}C(O)OR^{12a}$, $NR^{12}S(O)_2R^{12a}$, $C_{1-4}$ alkyl, $C_{2-6}$ alkenyl, $C_{2-6}$ alkynyl, $C_{1-4}$ alkoxy and $C_{1-4}$ haloalkyl;

$R^{11}$, at each occurrence, is independently selected from the group consisting of halogen, OH, $CF_3$, $OCHF_2$, $OCF_3$, CN, $NO_2$, $OCH_3$, $SCH_3$, $C_{1-4}$ alkyl, $C_{2-6}$ alkenyl, $C_{2-6}$ alkynyl, $C_{1-4}$ alkoxy and $C_{1-4}$ haloalkyl;

$R^{12}$ and $R^{12a}$, at each occurrence, are independently selected from the group consisting of H and $C_{1-4}$ alkyl;

$R^{13}$, at each occurrence, is independently selected from the group consisting of H, OH, halogen, CN, $NO_2$, $CF_3$, $C_{1-4}$ alkyl, $C_{2-4}$ alkenyl, $C_{2-4}$ alkynyl, $C_{1-4}$ haloalkyl and $C_{1-3}$ alkoxy.

2. The compound according to claim 1, wherein $R^3$ and $R^{3a}$ are independently selected from the group consisting of hydrogen, halogen, $CF_3$, $OCHF_2$, $OCF_3$, CN, $OCH_3$, $SCH_3$, $C_{1-4}$ alkyl.

3. The compound according to claim 1, wherein B is selected from the group consisting of a direct bond, oxygen, sulfur, $NR^6$, C(O), $C(O)NR^6$.

4. The compound according to claim 1, wherein $R^8$ is selected from the group consisting of $C_{1-6}$ alkyl optionally substituted with 1 to 4 $R^9$, $C_{2-6}$ alkenyl optionally substituted with 1 to 4 $R^9$, $C_{2-6}$ alkynyl optionally substituted with 1 to 4 $R^9$, $C_{3-8}$ cycloalkyl optionally substituted with 1 to 4 $R^{10}$, 3-6 membered heterocyclyl optionally substituted with 1 to 3 $R^{10}$, aryl optionally substituted with 1 to 3 $R^4$, 5-10 membered heteroaryl optionally substituted with 1 to 3 $R^4$.

5. The compound according to claim 1, wherein
$R^4$, at each occurrence, is independently selected from the group consisting of halogen OH, $CF_3$, $OCHF_2$, $OCF_3$, CN, $NO_2$, $OCH_3$, $SCH_3$, $OR^5$, $SR^5$, $NR^5R^6$, $S(O)R^5$, $S(O)_2R^5$, $S(O)_2NR^5R^6$, $C_{1-4}$ alkyl, $C_{3-6}$ cycloalkyl, 3-6 membered heterocyclyl, any of which may be optionally substituted with 1 to 6 $R^9$;

$R^5$ and $R^6$ are independently selected from the group consisting of methyl, ethyl, n-propyl, propyl and cyclopropyl;

alternatively, $R^5$ and $R^6$ join to form a 3-6-membered ring optionally substituted with oxygen or $NR^{12}$;

$R^9$, at each occurrence, is independently selected from the group consisting of halogen, OH, $CF_3$, $OCHF_2$, $OCF_3$, CN, $OCH_3$ and $N(CH_3)_2$;

$R^{12}$ and $R^{12a}$, at each occurrence, are independently selected from the group consisting of H, methyl and ethyl.

6. The compound according to claim 1, wherein
$R^8$ is selected from the group consisting of $C_{1-4}$ alkyl optionally substituted with 1 to 4 $R^9$, $C_{3-8}$ cycloalkyl optionally substituted with 1 to 4 $R^{10}$; 3-6 membered heterocyclyl substituted with 0 to 3 $R^{10}$, aryl optionally substituted with 1 to 3 $R^4$, 5-10 membered heteroaryl optionally substituted with 1 to 3 $R^4$;

$R^4$, at each occurrence, is independently selected from the group consisting of halogen OH, $CF_3$, $OCHF_2$, $OCF_3$, CN, $NO_2$, $OCH_3$, $SCH_3$, $N(CH_3)_2$, methyl, ethyl, n-propyl, i-propyl and cyclopropyl;

$R^{10}$, at each occurrence, is independently selected from the group consisting of =O, halogen, OH, $CF_3$, $OCHF_2$, $OCF_3$, CN, $NO_2$, $OCH_3$, $SCH_3$, methyl, ethyl, n-propyl, i-propyl and cyclopropyl, $NR^{12}R^{12a}$, $C(O)NR^{12}R^{12a}$, $C(O)OR^{12}$.

7. The compound according to claim 1, wherein $R^3$ and $R^{3a}$ are independently selected from the group consisting of hydrogen and methyl.

8. The compound according to claim 1, wherein $R^1$ is selected from the group consisting of 2-halo-phenyl, 2-($C_{1-3}$)alkyl-phenyl, 2-($C_{1-3}$)alkoxy-phenyl, 2-$CF_3$-phenyl, 2-CN-phenyl, 2-halo-4-pyridyl, 2-($C_{1-3}$) alkyl-4-pyridyl, 2-($C_{1-3}$) alkoxy-4-pyridyl, 2-$CF_3$-4-pyridyl, 2-CN-4-pyridyl, 2-halo-4-halophenyl, 2-($C_{1-3}$)alkyl-4-halo-phenyl, 2-($C_{1-3}$)alkoxy-4-halo-phenyl, 2-$CF_3$-4-halo-phenyl, 2-CN-4-halo-phenyl, 2-halo-4-($C_{1-3}$)alkyl-phenyl, 2-($C_{1-3}$)alkyl-4-($C_{1-3}$)alkyl-phenyl, 2-($C_{1-3}$)alkoxy-4-($C_{1-3}$)alkyl-phenyl, 2-$CF_3$-4-($C_{1-3}$)alkyl-phenyl, 2-CN-4-($C_{1-3}$)alkyl-phenyl, 2-halo-4-($C_{1-3}$)alkyl-phenyl, 2-($C_{1-3}$)alkyl-4-($C_{1-3}$) alkoxy-phenyl, 2-($C_{1-3}$)alkoxy-4-($C_{1-3}$) alkoxy-phenyl, 2-$CF_3$-4-($C_{1-3}$)alkoxy-phenyl, 2-CN-4-($C_{1-3}$)alkoxy-phenyl, 2-halo-4-$CF_3$-phenyl, 2-($C_{1-3}$)alkyl-4-$CF_3$-phenyl, 2-($C_{1-3}$)alkoxy-4-$CF_3$-phenyl, 2-halo-4-CN-phenyl, 2-($C_{1-3}$)alkyl-4-CN-phenyl and 2-($C_{1-3}$)alkoxy-4-CN-phenyl.

9. The compounds according to claim 1, wherein the compounds are selected from the group consisting of:

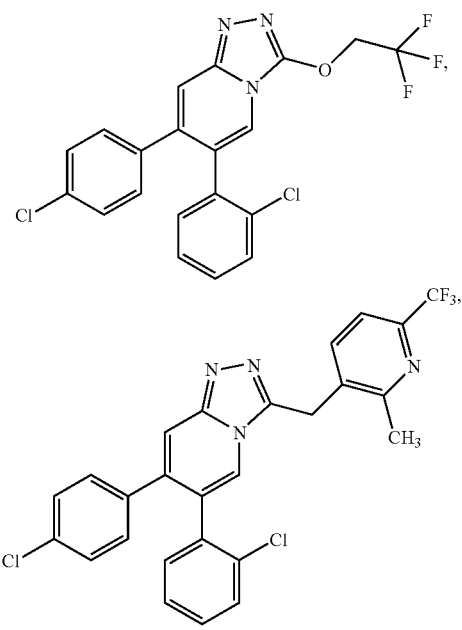

-continued
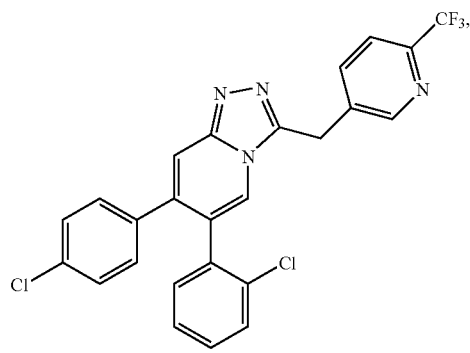
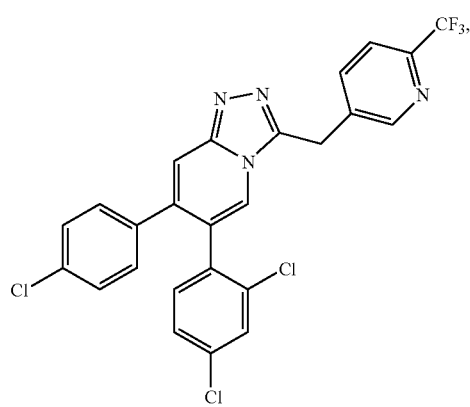
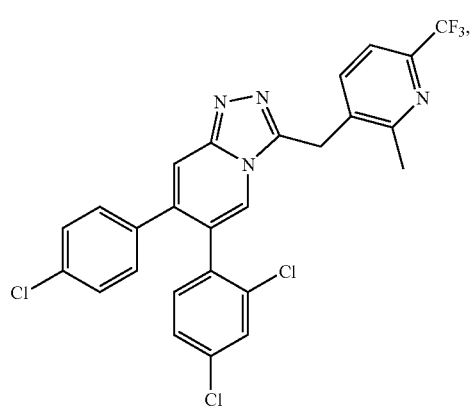
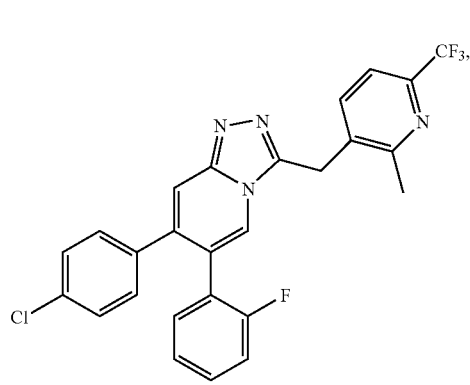
-continued
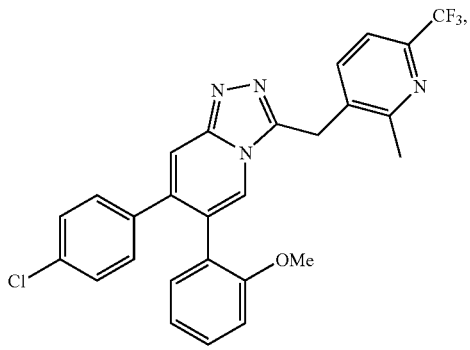
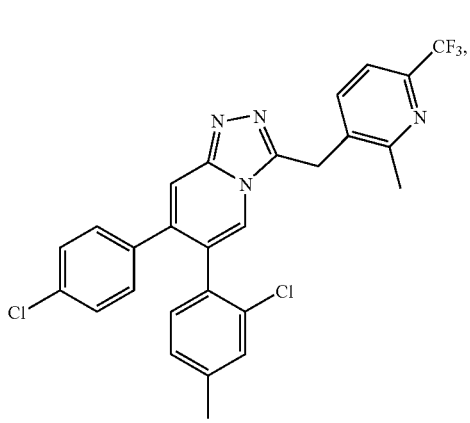
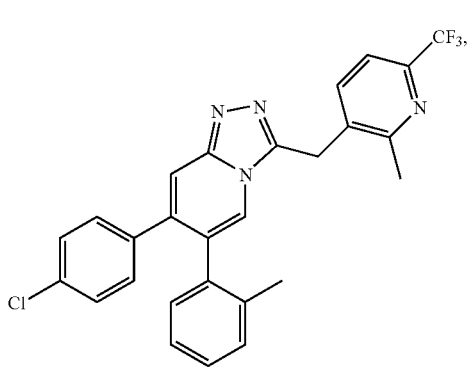
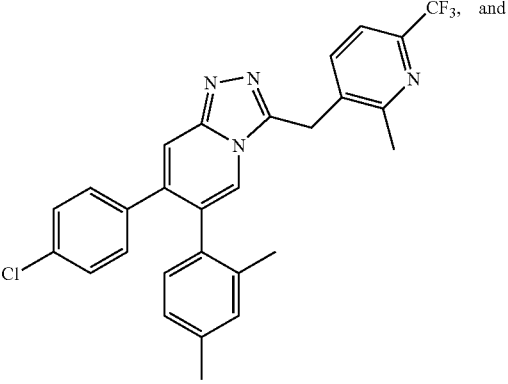

-continued
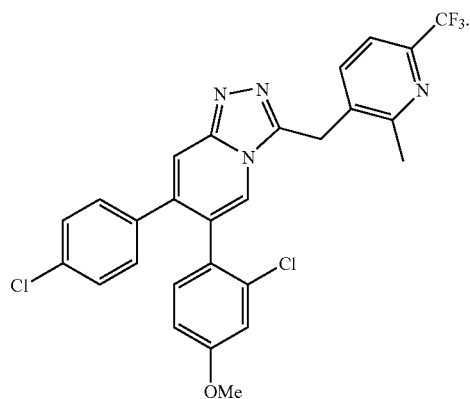
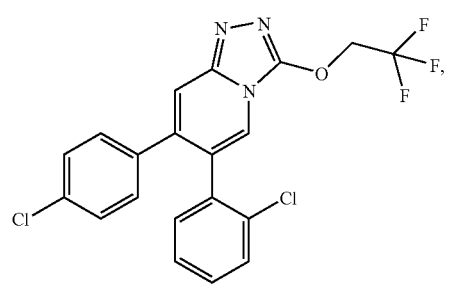
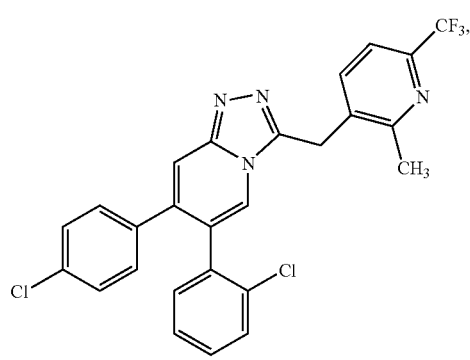
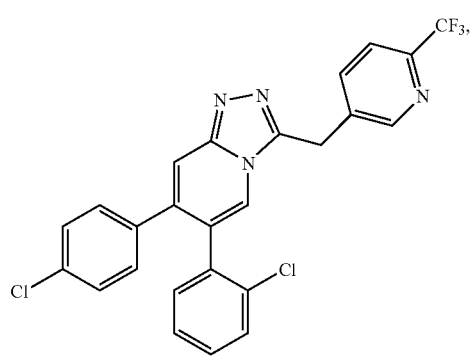
-continued
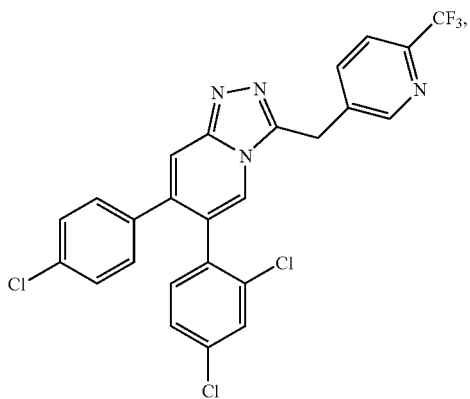
10. The compounds according to claim 1, wherein the compounds are selected from the group consisting of:
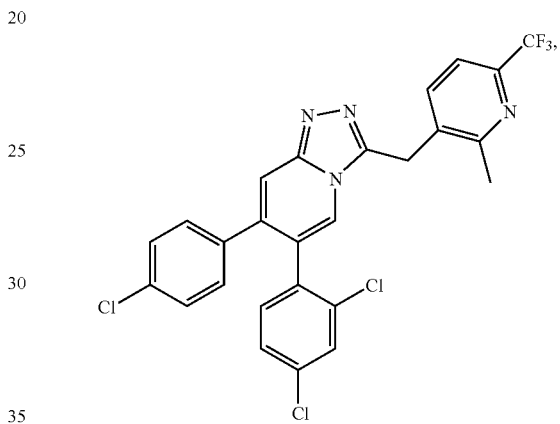
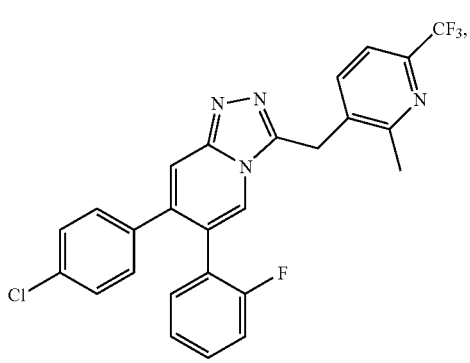
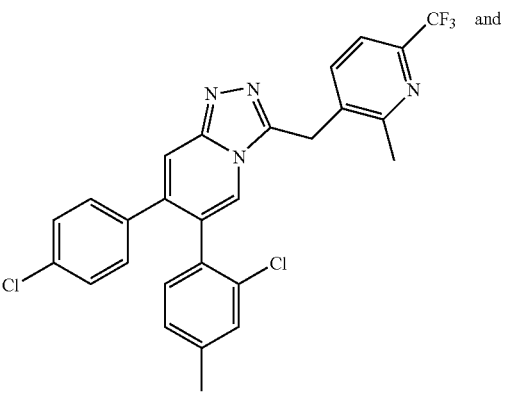

-continued

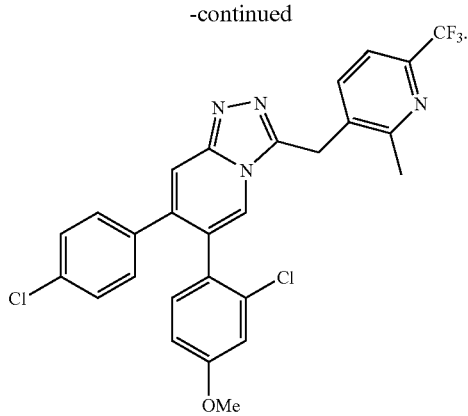

11. A pharmaceutical composition, comprising: at least one compound according to claim 1; and at least one pharmaceutically acceptable carrier or diluent.

12. The pharmaceutical composition according to claim 11 further comprising: at least one additional therapeutic agent selected from the group consisting of: anti-obesity agents, appetite suppressants, anti-diabetic agents, anti-hyperlipidemia agents, hypolipidemic agents, hypocholesterolemic agents, cholesterol-lowering agents, lipid-lowering agents, HDL-raising agent, and anti-hypertensive agents.

13. The pharmaceutical combination according to claim 12 wherein the additional therapeutic agent may be administered prior to, simultaneously with, or following the administration of the pharmaceutical composition of claim 11.

14. A method for treating obesity, comprising: administering a therapeutically effective amount of at least one compound according to claim 1 to a patient in need.

15. A method for smoking cessation, comprising: administering a therapeutically effective amount of at least one compound according to claim 1 to a patient in need.

* * * * *

UNITED STATES PATENT AND TRADEMARK OFFICE
CERTIFICATE OF CORRECTION

PATENT NO. : 7,858,639 B2
APPLICATION NO. : 12/609436
DATED : December 28, 2010
INVENTOR(S) : Sun et al.

Page 1 of 1

It is certified that error appears in the above-identified patent and that said Letters Patent is hereby corrected as shown below:

Column 74, line 36, Claim 1, after "independently", delete "is".

Column 75, line 45, Claim 4, delete "$R^{10}$," and insert -- $R^{10}$; --.

Column 75, line 58, Claim 5, delete "propyl" and insert -- i-propyl --.

Signed and Sealed this
Twenty-fourth Day of May, 2011

David J. Kappos
*Director of the United States Patent and Trademark Office*